United States Patent
Yamanaka et al.

(10) Patent No.: US 9,506,039 B2
(45) Date of Patent: Nov. 29, 2016

(54) EFFICIENT METHOD FOR ESTABLISHING INDUCED PLURIPOTENT STEM CELLS

(75) Inventors: Shinya Yamanaka, Kyoto (JP); Kazutoshi Takahashi, Kyoto (JP); Koji Tanabe, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 13/991,341

(22) PCT Filed: Dec. 2, 2011

(86) PCT No.: PCT/JP2011/077992
§ 371 (c)(1),
(2), (4) Date: Jun. 3, 2013

(87) PCT Pub. No.: WO2012/074117
PCT Pub. Date: Jun. 7, 2012

(65) Prior Publication Data
US 2013/0267030 A1 Oct. 10, 2013

Related U.S. Application Data

(60) Provisional application No. 61/419,320, filed on Dec. 3, 2010.

(51) Int. Cl.
| | | |
|---|---|---|
| *C12N 5/00* | (2006.01) | |
| *C12N 5/02* | (2006.01) | |
| *C12N 5/074* | (2010.01) | |
| *C12N 15/85* | (2006.01) | |

(52) U.S. Cl.
CPC ............ *C12N 5/0696* (2013.01); *C12N 15/85* (2013.01); *C12N 2501/115* (2013.01); *C12N 2501/415* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2501/998* (2013.01); *C12N 2506/1307* (2013.01); *C12N 2510/00* (2013.01)

(58) Field of Classification Search
CPC .................................................. C12N 5/0696
See application file for complete search history.

(56) References Cited

U.S. PATENT DOCUMENTS

| | | |
|---|---|---|
| 2009/0047263 A1 | 2/2009 | Yamanaka et al. |
| 2009/0068742 A1 | 3/2009 | Yamanaka |
| 2009/0093090 A1 | 4/2009 | Ewe et al. |
| 2009/0227032 A1 | 9/2009 | Yamanaka et al. |
| 2010/0093090 A1 | 4/2010 | Deng et al. |
| 2010/0216236 A1 | 8/2010 | Yamanaka |
| 2011/0117653 A1 | 5/2011 | Enoki et al. |

FOREIGN PATENT DOCUMENTS

| | | |
|---|---|---|
| CA | 2 731 007 A1 | 1/2010 |
| EP | 1 970 446 A1 | 9/2008 |
| EP | 2 253 700 A1 | 11/2010 |
| WO | WO 2007/069666 A1 | 6/2007 |
| WO | WO 2008/124133 A1 | 10/2008 |
| WO | WO 2009/133971 A1 | 11/2009 |
| WO | WO 2009/157593 A1 | 12/2009 |
| WO | WO 2010/004989 A1 | 1/2010 |
| WO | WO 2010/098419 A1 | 9/2010 |

OTHER PUBLICATIONS

Stadtfield , 2008, Cell, 2:230-240.*
Buganim, 2012,Cell, 150:1209-1222.*
NIH (Stem Cells: Scientific Progress and Future Research Directions, Department of Health and Human Services, Chapter 1, pp. 1-4, Jun. 2001.*
Thomson et al. (PNAS, 92:7844-7848 (Aug. 1995)).*
Djuric and Ellis, 202, Stem Cell Research and Therapy, 2010,1:3, pp. 1-6.*
Marson et al., *Cell Stem Cell*, 3(2): 132-135 (2008).
Nakagawa et al., *Nature Biotechnology*, 26: 101-106 (2008).
Noguchi et al., *The FASEB Journal*, 21(10): 2273-2284 (2007).
Okita et al., *Nature*, 448: 313-317 (2007).
Rebollo et al., *Blood*, 94(9): 2971-2980 (1999).
Takahashi et al., *Cell*, 126: 663-676 (2006).
Takahashi et al., *Cell*, 131: 861-872 (2007).
Takahashi et al., *The Journal of Biological Chemistry*, 280(38): 32768-32774 (2005).
Takahashi et al., *Nature*, 423: 541-545 (2003) [abstract only].
Yamnik et al., *Res. FEBS Letters*, 584(1): 124-128 (2010).
Yu et al., *Science*, 318: 1917-1920 (2007).
Zhao et al., *Cell Stem Cell*, 3(5): 475-479 (2008).
Japanese Patent Office, International Search Report in International Patent Application No. PCT/JP2011/077992 (Mar. 6, 2012).
Kondo et al., "Focal Transplantation of Human iPSC-Derived Glial-Rich Neural Progenitors Improves Lifespan of ALS Mice," *Stem Cell Reports*, 3(2): 242-249 (Aug. 12, 2014).
European Patent Office, Extended European Search Report in European Patent Application No. 11845474.3 (Dec. 18, 2014).
Mikkelsen et al., "Dissecting direct reprogramming through integrative genomic analysis," *Nature*, 454: 49-55 and methods and supplementary information [doi:10.1038/nature07056] (Jul. 3, 2008).

(Continued)

*Primary Examiner* — Valarie Bertoglio
(74) *Attorney, Agent, or Firm* — Leydig, Voit & Mayer, Ltd.

(57) ABSTRACT

The invention provides a method of improving the efficiency of establishment of induced pluripotent stem cells by increasing, in a nuclear reprogramming step of somatic cell, the level of activated form of one or more proteins selected from the group consisting of Ras family members, PI3 kinase, RalGEF, Raf, AKT family members, Rheb, TCL1 and S6K. The invention also provides a method of producing induced pluripotent stem cells by contacting a somatic cell with a nuclear reprogramming substance and one or more of such proteins and nucleic acids that encode such proteins. The invention further provides an induced pluripotent stem cell that has an exogenous nucleic acid encoding such a protein, as well as agents for use in the aforesaid methods.

14 Claims, 10 Drawing Sheets

(56) References Cited

OTHER PUBLICATIONS

Wernig et al., "In vitro reprogramming of fibroblasts into a pluripotent ES-cell-like state," *Nature*, 448: 318-324 and methods and supplementary information [doi:10.1038/nature05944] (Jul. 19, 2007).
Altomare et al., *Oncogene*, 24: 7455-7464 (2005).
Cajanek et al., *Journal of Cellular Biochemistry*, 111: 1077-1079 (2010).
Holz et al., *Cell*, 123: 569-580 (2005).
Hong et al., *J. Biol. Chem.*, 283(34): 23129-23138 (2008).
Howlett et al., *PLoS Genetics*, 4(11): e1000277 (2008) [available on the internet at http://dx.doi.org/10.1371/journal.pgen.1000277].
Kim et al., *Blood*, 105(4): 1717-1723 (2005).
Lim et al., *Cancer Cell*, 8: 381-392 (2005).
Liu et al., *Anticancer Research*, 24: 2697-2704 (2004).
Long et al., *Current Biology*, 15: 702-713 (2005).
Matsubara et al., *Oncogene*, 18: 1303-1312 (1999).
Mitin et al., *Oncogene*, 20: 1276-1286 (2001).
Oinuma et al., *J. Biol. Chem.*, 282(1): 303-318 (2007).
Qiu et al., *Reproduction*, 128: 355-363 (2004).
Rokutanda et al., *Developmental Biology*, 328: 78-93 (2009).
Sato et al., *Methods in Enzymology*, 438: 307-320 (2008).
Zhu et al., *Cell Stem Cell*, 7: 651-655 (2010) [available on the internet at http://dx.doi.org/10.1016/j.stem.2010.11.015].

* cited by examiner

SEQUENCE LISTING

<160> NUMBER OF SEQ ID NOS: 49

<210> SEQ ID NO 1
<211> LENGTH: 570
<212> TYPE: DNA
<213> ORGANISM: Mus musculus
<220> FEATURE:
<221> NAME/KEY: CDS
<222> LOCATION: (1)..(570)

<400> SEQUENCE: 1

```
atg aca gaa tac aag ctt gtg gtg gtg ggc gct gga ggc gtg gga aag      48
Met Thr Glu Tyr Lys Leu Val Val Val Gly Ala Gly Gly Val Gly Lys
1               5                  10                  15 agt gcc ctg acc atc cag ctg atc cag aac cac ttt gtg gac gag tat      96
Ser Ala Leu Thr Ile Gln Leu Ile Gln Asn His Phe Val Asp Glu Tyr
            20                  25                  30 gat ccc act ata gag gac tcc tac cgg aaa cag gtg gtc att gat ggg     144
Asp Pro Thr Ile Glu Asp Ser Tyr Arg Lys Gln Val Val Ile Asp Gly
        35                  40                  45 gag aca tgt cta ctg gac atc tta gac aca gca ggt caa gaa gag tat     192
Glu Thr Cys Leu Leu Asp Ile Leu Asp Thr Ala Gly Gln Glu Glu Tyr
    50                  55                  60 agt gcc atg cgg gac cag tac atg cgc aca ggg gag ggc ttc ctc tgt     240
Ser Ala Met Arg Asp Gln Tyr Met Arg Thr Gly Glu Gly Phe Leu Cys
65                  70                  75                  80 gta ttt gcc atc aac aac acc aag tcc ttc gag gac atc cat cag tac     288
Val Phe Ala Ile Asn Asn Thr Lys Ser Phe Glu Asp Ile His Gln Tyr
                85                  90                  95 agg gag cag atc aag cgg gtg aaa gat tca gat gat gtg cca atg gtg     336
Arg Glu Gln Ile Lys Arg Val Lys Asp Ser Asp Asp Val Pro Met Val
            100                 105                 110 ctg gtg ggc aac aag tgt gac ctg gct gct cgc act gtt gag tct cgg     384
Leu Val Gly Asn Lys Cys Asp Leu Ala Ala Arg Thr Val Glu Ser Arg
        115                 120                 125 cag gcc cag gac ctt gct cgc agc tat ggc atc ccc tac att gaa aca     432
Gln Ala Gln Asp Leu Ala Arg Ser Tyr Gly Ile Pro Tyr Ile Glu Thr
    130                 135                 140 tca gcc aag acc cgg cag ggc gtg gag gat gcc ttc tat aca cta gtc     480
Ser Ala Lys Thr Arg Gln Gly Val Glu Asp Ala Phe Tyr Thr Leu Val
145                 150                 155                 160 cgt gag att cgg cag cat aaa ttg cgg aaa ctg aac cca ccc gat gag     528
Arg Glu Ile Arg Gln His Lys Leu Arg Lys Leu Asn Pro Pro Asp Glu
                165                 170                 175 agt ggt cct ggc tgc atg agc tgc aaa tgt gtg ctg tcc tga             570
Ser Gly Pro Gly Cys Met Ser Cys Lys Cys Val Leu Ser
            180                 185
```

<210> SEQ ID NO 2

```
<211> LENGTH: 189
<212> TYPE: PRT
<213> ORGANISM: Mus musculus

<400> SEQUENCE: 2

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 3
<211> LENGTH: 570
<212> TYPE: DNA
<213> ORGANISM: Homo sapiens
<220> FEATURE:
<221> NAME/KEY: CDS
<222> LOCATION: (1)..(570)

<400> SEQUENCE: 3 atg acg gaa tat aag ctg gtg gtg gtg ggc gcc ggc ggt gtg ggc aag        48
Met Thr Glu Tyr Lys Leu Val Val Val Gly Ala Gly Gly Val Gly Lys
1               5                   10                  15 agt gcg ctg acc atc cag ctg atc cag aac cat ttt gtg gac gaa tac        96
Ser Ala Leu Thr Ile Gln Leu Ile Gln Asn His Phe Val Asp Glu Tyr
            20                  25                  30 gac ccc act ata gag gat tcc tac cgg aag cag gtg gtc att gat ggg       144
Asp Pro Thr Ile Glu Asp Ser Tyr Arg Lys Gln Val Val Ile Asp Gly
        35                  40                  45 gag acg tgc ctg ttg gac atc ctg gat acc gcc ggc cag gag gag tac       192
Glu Thr Cys Leu Leu Asp Ile Leu Asp Thr Ala Gly Gln Glu Glu Tyr
50                  55                  60 agc gcc atg cgg gac cag tac atg cgc acc ggg gag ggc ttc ctg tgt       240
Ser Ala Met Arg Asp Gln Tyr Met Arg Thr Gly Glu Gly Phe Leu Cys
65                  70                  75                  80 gtg ttt gcc atc aac aac acc aag tct ttt gag gac atc cac cag tac       288
Val Phe Ala Ile Asn Asn Thr Lys Ser Phe Glu Asp Ile His Gln Tyr
                85                  90                  95 agg gag cag atc aaa cgg gtg aag gac tcg gat gac gtg ccc atg gtg       336
Arg Glu Gln Ile Lys Arg Val Lys Asp Ser Asp Asp Val Pro Met Val
```

```
ctg gtg ggg aac aag tgt gac ctg gct gca cgc act gtg gaa tct cgg      384
Leu Val Gly Asn Lys Cys Asp Leu Ala Ala Arg Thr Val Glu Ser Arg
        115                 120                 125 cag gct cag gac ctc gcc cga agc tac ggc atc ccc tac atc gag acc      432
Gln Ala Gln Asp Leu Ala Arg Ser Tyr Gly Ile Pro Tyr Ile Glu Thr
    130                 135                 140 tcg gcc aag acc cgg cag gga gtg gag gat gcc ttc tac acg ttg gtg      480
Ser Ala Lys Thr Arg Gln Gly Val Glu Asp Ala Phe Tyr Thr Leu Val
145                 150                 155                 160 cgt gag atc cgg cag cac aag ctg cgg aag ctg aac cct cct gat gag      528
Arg Glu Ile Arg Gln His Lys Leu Arg Lys Leu Asn Pro Pro Asp Glu
                165                 170                 175 agt ggc ccc ggc tgc atg agc tgc aag tgt gtg ctc tcc tga              570
Ser Gly Pro Gly Cys Met Ser Cys Lys Cys Val Leu Ser
                180                 185
```

<210> SEQ ID NO 4
<211> LENGTH: 189
<212> TYPE: PRT
<213> ORGANISM: Homo sapiens

<400> SEQUENCE: 4

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

<210> SEQ ID NO 5
<211> LENGTH: 567
<212> TYPE: DNA
<213> ORGANISM: Mus musculus
<220> FEATURE:
<221> NAME/KEY: CDS
<222> LOCATION: (1)..(567)

<400> SEQUENCE: 5

```
atg act gag tat aaa ctt gtg gtg gtt gga gct ggt ggc gta ggc aag      48
Met Thr Glu Tyr Lys Leu Val Val Val Gly Ala Gly Gly Val Gly Lys
```

```
               1               5                   10                  15
agc gcc ttg acg ata cag cta att cag aat cac ttt gtg gat gag tat        96
Ser Ala Leu Thr Ile Gln Leu Ile Gln Asn His Phe Val Asp Glu Tyr
                20                  25                  30 gac cct acg ata gag gac tcc tac agg aaa caa gta gta att gat gga       144
Asp Pro Thr Ile Glu Asp Ser Tyr Arg Lys Gln Val Val Ile Asp Gly
                35                  40                  45 gaa acc tgt ctc ttg gat att ctc gac aca gca ggt caa gag gag tac       192
Glu Thr Cys Leu Leu Asp Ile Leu Asp Thr Ala Gly Gln Glu Glu Tyr
    50                  55                  60 agt gca atg agg gac cag tac atg aga act ggg gag ggc ttt ctt tgt       240
Ser Ala Met Arg Asp Gln Tyr Met Arg Thr Gly Glu Gly Phe Leu Cys
65                  70                  75                  80 gta ttt gcc ata aat aat act aaa tca ttt gaa gat att cac cat tat       288
Val Phe Ala Ile Asn Asn Thr Lys Ser Phe Glu Asp Ile His His Tyr
                85                  90                  95 aga gaa caa att aaa aga gta aag gac tct gaa gat gtg cct atg gtc       336
Arg Glu Gln Ile Lys Arg Val Lys Asp Ser Glu Asp Val Pro Met Val
                100                 105                 110 ctg gta ggg aat aag tgt gat ttg cct tct aga aca gta gac acg aaa       384
Leu Val Gly Asn Lys Cys Asp Leu Pro Ser Arg Thr Val Asp Thr Lys
                115                 120                 125 cag gct cag gag tta gca agg agt tac ggg att ccg ttc att gag acc       432
Gln Ala Gln Glu Leu Ala Arg Ser Tyr Gly Ile Pro Phe Ile Glu Thr
        130                 135                 140 tca gca aag aca aga cag ggt gtt gac gat gcc ttc tat aca tta gtc       480
Ser Ala Lys Thr Arg Gln Gly Val Asp Asp Ala Phe Tyr Thr Leu Val
145                 150                 155                 160 cga gaa att cga aaa cat aaa gaa aag atg agc aaa gat ggg aag aag       528
Arg Glu Ile Arg Lys His Lys Glu Lys Met Ser Lys Asp Gly Lys Lys
                165                 170                 175 aag aag aag aag tca agg aca agg tgt aca gtt atg tga               567
Lys Lys Lys Lys Ser Arg Thr Arg Cys Thr Val Met
                180                 185
```

<210> SEQ ID NO 6
<211> LENGTH: 188
<212> TYPE: PRT
<213> ORGANISM: Mus musculus

<400> SEQUENCE: 6

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
                35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Glu Leu Ala Arg Ser Tyr Gly Ile Pro Phe Ile Glu Thr
```

```
                          130                 135                 140
Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Arg Thr Arg Cys Thr Val Met
            180                 185

<210> SEQ ID NO 7
<211> LENGTH: 570
<212> TYPE: DNA
<213> ORGANISM: Homo sapiens
<220> FEATURE:
<221> NAME/KEY: CDS
<222> LOCATION: (1)..(570)

<400> SEQUENCE: 7 atg act gaa tat aaa ctt gtg gta gtt gga gct ggt ggc gta ggc aag      48
Met Thr Glu Tyr Lys Leu Val Val Val Gly Ala Gly Gly Val Gly Lys
1               5                   10                  15 agt gcc ttg acg ata cag cta att cag aat cat ttt gtg gac gaa tat      96
Ser Ala Leu Thr Ile Gln Leu Ile Gln Asn His Phe Val Asp Glu Tyr
                20                  25                  30 gat cca aca ata gag gat tcc tac agg aag caa gta gta att gat gga     144
Asp Pro Thr Ile Glu Asp Ser Tyr Arg Lys Gln Val Val Ile Asp Gly
            35                  40                  45 gaa acc tgt ctc ttg gat att ctc gac aca gca ggt caa gag gag tac     192
Glu Thr Cys Leu Leu Asp Ile Leu Asp Thr Ala Gly Gln Glu Glu Tyr
        50                  55                  60 agt gca atg agg gac cag tac atg agg act ggg gag ggc ttt ctt tgt     240
Ser Ala Met Arg Asp Gln Tyr Met Arg Thr Gly Glu Gly Phe Leu Cys
65                  70                  75                  80 gta ttt gcc ata aat aat act aaa tca ttt gaa gat att cac cat tat     288
Val Phe Ala Ile Asn Asn Thr Lys Ser Phe Glu Asp Ile His His Tyr
                85                  90                  95 aga gaa caa att aaa aga gtt aag gac tct gaa gat gta cct atg gtc     336
Arg Glu Gln Ile Lys Arg Val Lys Asp Ser Glu Asp Val Pro Met Val
            100                 105                 110 cta gta gga aat aaa tgt gat ttg cct tct aga aca gta gac aca aaa     384
Leu Val Gly Asn Lys Cys Asp Leu Pro Ser Arg Thr Val Asp Thr Lys
        115                 120                 125 cag gct cag gac tta gca aga agt tat gga att cct ttt att gaa aca     432
Gln Ala Gln Asp Leu Ala Arg Ser Tyr Gly Ile Pro Phe Ile Glu Thr
    130                 135                 140 tca gca aag aca aga cag aga gtg gag gat gct ttt tat aca ttg gtg     480
Ser Ala Lys Thr Arg Gln Arg Val Glu Asp Ala Phe Tyr Thr Leu Val
145                 150                 155                 160 agg gag atc cga caa tac aga ttg aaa aaa atc agc aaa gaa gaa aag     528
Arg Glu Ile Arg Gln Tyr Arg Leu Lys Lys Ile Ser Lys Glu Glu Lys
                165                 170                 175 act cct ggc tgt gtg aaa att aaa aaa tgc att ata atg taa              570
Thr Pro Gly Cys Val Lys Ile Lys Lys Cys Ile Ile Met
            180                 185

<210> SEQ ID NO 8
<211> LENGTH: 189
<212> TYPE: PRT
<213> ORGANISM: Homo sapiens

<400> SEQUENCE: 8

Met Thr Glu Tyr Lys Leu Val Val Val Gly Ala Gly Gly Val Gly Lys
```

```
  1               5                  10                 15
Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
            50                  55                  60

Ser Ala Met Arg Asp Gln Tyr Met Arg Thr Gly Glu Gly Phe Leu Cys
 65                 70                  75                  80

Val Phe Ala Ile Asn Asn Thr Lys Ser Phe Glu Asp Ile His His Tyr
                    85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
            130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 9
<211> LENGTH: 570
<212> TYPE: DNA
<213> ORGANISM: Mus musculus
<220> FEATURE:
<221> NAME/KEY: CDS
<222> LOCATION: (1)..(570)

<400> SEQUENCE: 9 atg act gag tac aaa ctg gtg gtg gtt gga gca ggt ggt gtt ggg aaa      48
Met Thr Glu Tyr Lys Leu Val Val Val Gly Ala Gly Gly Val Gly Lys
 1               5                  10                  15 agc gcc ttg acg atc cag cta atc cag aac cac ttt gtg gat gaa tat      96
Ser Ala Leu Thr Ile Gln Leu Ile Gln Asn His Phe Val Asp Glu Tyr
            20                  25                  30 gat ccc acc ata gag gat tct tac cga aag caa gtg gtg att gat ggt     144
Asp Pro Thr Ile Glu Asp Ser Tyr Arg Lys Gln Val Val Ile Asp Gly
            35                  40                  45 gag acc tgc ctg ctg gac ata ctg gac aca gct gga caa gag gag tac     192
Glu Thr Cys Leu Leu Asp Ile Leu Asp Thr Ala Gly Gln Glu Glu Tyr
            50                  55                  60 agt gcc atg aga gac cag tac atg agg aca ggc gaa ggg ttc ctc tgt     240
Ser Ala Met Arg Asp Gln Tyr Met Arg Thr Gly Glu Gly Phe Leu Cys
 65                 70                  75                  80 gta ttt gcc atc aat aat agc aaa tca ttt gca gat att aac ctc tac     288
Val Phe Ala Ile Asn Asn Ser Lys Ser Phe Ala Asp Ile Asn Leu Tyr
                    85                  90                  95 agg gag caa att aag cgt gtg aaa gat tct gat gat gtc ccc atg gtg     336
Arg Glu Gln Ile Lys Arg Val Lys Asp Ser Asp Asp Val Pro Met Val
                100                 105                 110 ctg gta ggc aac aag tgt gac ttg cca aca agg aca gtt gac aca aag     384
Leu Val Gly Asn Lys Cys Asp Leu Pro Thr Arg Thr Val Asp Thr Lys
                115                 120                 125 caa gcc cac gaa ctg gcc aag agt tac gga att cca ttc att gag acc     432
Gln Ala His Glu Leu Ala Lys Ser Tyr Gly Ile Pro Phe Ile Glu Thr
```

```

Gln Ala His Glu Leu Ala Lys Ser Tyr Gly Ile Pro Phe Ile Glu Thr
    130                 135                 140 tca gcc aag acc cga cag ggt gtg gag gat gcc ttt tac aca ctg gta    480
Ser Ala Lys Thr Arg Gln Gly Val Glu Asp Ala Phe Tyr Thr Leu Val
145                 150                 155                 160 agg gag ata cgc cag tac cga atg aaa aag ctc aac agc agt gac gat    528
Arg Glu Ile Arg Gln Tyr Arg Met Lys Lys Leu Asn Ser Ser Asp Asp
                165                 170                 175 ggc act caa ggt tgt atg ggg ctg ccc tgt gtg ctg atg tag            570
Gly Thr Gln Gly Cys Met Gly Leu Pro Cys Val Leu Met
                180                 185
```

<210> SEQ ID NO 10
<211> LENGTH: 189
<212> TYPE: PRT
<213> ORGANISM: Mus musculus

<400> SEQUENCE: 10

```
Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Tyr
 50                 55                  60

Ser Ala Met Arg Asp Gln Tyr Met Arg Thr Gly Glu Gly Phe Leu Cys
 65                 70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Leu Met
                180                 185
```

<210> SEQ ID NO 11
<211> LENGTH: 570
<212> TYPE: DNA
<213> ORGANISM: Homo sapiens
<220> FEATURE:
<221> NAME/KEY: CDS
<222> LOCATION: (1)..(570)

<400> SEQUENCE: 11

```
atg act gag tac aaa ctg gtg gtg gtt gga gca ggt ggt gtt ggg aaa     48
Met Thr Glu Tyr Lys Leu Val Val Val Gly Ala Gly Gly Val Gly Lys
1               5                   10                  15 agc gca ctg aca atc cag cta atc cag aac cac ttt gta gat gaa tat     96
Ser Ala Leu Thr Ile Gln Leu Ile Gln Asn His Phe Val Asp Glu Tyr
                20                  25                  30 gat ccc acc ata gag gat tct tac aga aaa caa gtg gtt ata gat ggt    144
```

```
Asp Pro Thr Ile Glu Asp Ser Tyr Arg Lys Gln Val Val Ile Asp Gly
             35                  40                  45 gaa acc tgt ttg ttg gac ata ctg gat aca gct gga caa gaa gag tac     192
Glu Thr Cys Leu Leu Asp Ile Leu Asp Thr Ala Gly Gln Glu Glu Tyr
 50                  55                  60 agt gcc atg aga gac caa tac atg agg aca ggc gaa ggc ttc ctc tgt     240
Ser Ala Met Arg Asp Gln Tyr Met Arg Thr Gly Glu Gly Phe Leu Cys
 65                  70                  75                  80 gta ttt gcc atc aat aat agc aag tca ttt gcg gat att aac ctc tac     288
Val Phe Ala Ile Asn Asn Ser Lys Ser Phe Ala Asp Ile Asn Leu Tyr
                 85                  90                  95 agg gag cag att aag cga gta aaa gac tcg gat gat gta cct atg gtg     336
Arg Glu Gln Ile Lys Arg Val Lys Asp Ser Asp Asp Val Pro Met Val
            100                 105                 110 cta gtg gga aac aag tgt gat ttg cca aca agg aca gtt gat aca aaa     384
Leu Val Gly Asn Lys Cys Asp Leu Pro Thr Arg Thr Val Asp Thr Lys
            115                 120                 125 caa gcc cac gaa ctg gcc aag agt tac ggg att cca ttc att gaa acc     432
Gln Ala His Glu Leu Ala Lys Ser Tyr Gly Ile Pro Phe Ile Glu Thr
        130                 135                 140 tca gcc aag acc aga cag ggt gtt gaa gat gct ttt tac aca ctg gta     480
Ser Ala Lys Thr Arg Gln Gly Val Glu Asp Ala Phe Tyr Thr Leu Val
145                 150                 155                 160 aga gaa ata cgc cag tac cga atg aaa aaa ctc aac agc agt gat gat     528
Arg Glu Ile Arg Gln Tyr Arg Met Lys Lys Leu Asn Ser Ser Asp Asp
                165                 170                 175 ggg act cag ggt tgt atg gga ttg cca tgt gtg gtg atg taa             570
Gly Thr Gln Gly Cys Met Gly Leu Pro Cys Val Val Met
            180                 185

<210> SEQ ID NO 12
<211> LENGTH: 189
<212> TYPE: PRT
<213> ORGANISM: Homo sapiens

<400> SEQUENCE: 12

Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Ser Lys Ser Phe Ala Asp Ile Asn Leu Tyr
                 85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175
```

Gly Thr Gln Gly Cys Met Gly Leu Pro Cys Val Val Met
            180                 185

<210> SEQ ID NO 13
<211> LENGTH: 684
<212> TYPE: DNA
<213> ORGANISM: Mus musculus
<220> FEATURE:
<221> NAME/KEY: CDS
<222> LOCATION: (1)..(684)

<400> SEQUENCE: 13

| | | |
|---|---|---|
| atg gct ttg cct aca aag tct agc atc ttg gac ctg agc tcc ggc acc<br>Met Ala Leu Pro Thr Lys Ser Ser Ile Leu Asp Leu Ser Ser Gly Thr<br>1               5                   10                  15 | | 48 |
| cca tgc acc aga tct cca gag gaa agt cac gag gct tgg gca cag tgc<br>Pro Cys Thr Arg Ser Pro Glu Glu Ser His Glu Ala Trp Ala Gln Cys<br>            20                  25                  30 | | 96 |
| aaa gat gct ggc agg cag cta ccc gag tac aag gca gtg gtg gtg ggt<br>Lys Asp Ala Gly Arg Gln Leu Pro Glu Tyr Lys Ala Val Val Val Gly<br>        35                  40                  45 | | 144 |
| gca agt ggt gtt ggt aaa agt gct ctc acc atc cag atg act cac caa<br>Ala Ser Gly Val Gly Lys Ser Ala Leu Thr Ile Gln Met Thr His Gln<br>    50                  55                  60 | | 192 |
| tgc ttc gtg aaa gac cat gac ccc act atc caa gat tcc tac tgg aag<br>Cys Phe Val Lys Asp His Asp Pro Thr Ile Gln Asp Ser Tyr Trp Lys<br>65                  70                  75                  80 | | 240 |
| gaa gtg gcc agg gac aac gga ggc tac att cta aat gtt ctg gat aca<br>Glu Val Ala Arg Asp Asn Gly Gly Tyr Ile Leu Asn Val Leu Asp Thr<br>                85                  90                  95 | | 288 |
| tct ggg cag gat att cac cgg gct ctg cgt gac cag tgc ttg gca tct<br>Ser Gly Gln Asp Ile His Arg Ala Leu Arg Asp Gln Cys Leu Ala Ser<br>            100                 105                 110 | | 336 |
| ggt gat ggt gtg ctg ggc gtc ttt gct ctt gac gac ccc tcg tct ctg<br>Gly Asp Gly Val Leu Gly Val Phe Ala Leu Asp Asp Pro Ser Ser Leu<br>        115                 120                 125 | | 384 |
| gac cag ttg cag cag ata tgg tcc acc tgg acc cct cac cac aag cag<br>Asp Gln Leu Gln Gln Ile Trp Ser Thr Trp Thr Pro His His Lys Gln<br>    130                 135                 140 | | 432 |
| cct ctg gta cta gtg ggc aac aag tgt gac ctg gtg acc act gct gga<br>Pro Leu Val Leu Val Gly Asn Lys Cys Asp Leu Val Thr Thr Ala Gly<br>145                 150                 155                 160 | | 480 |
| gat gct cat gct gcc gca gcc ctc ctt gct cac aag ttg ggg gcc ccc<br>Asp Ala His Ala Ala Ala Leu Leu Ala His Lys Leu Gly Ala Pro<br>                165                 170                 175 | | 528 |
| ttg gtg aag acc tca gcc aag acg cgg caa ggt gtg gag gaa gcc ttt<br>Leu Val Lys Thr Ser Ala Lys Thr Arg Gln Gly Val Glu Glu Ala Phe<br>            180                 185                 190 | | 576 |
| gcc ctg ctt gtc cat gag att cag agg gcc cag gag gct gtg gcc gaa<br>Ala Leu Leu Val His Glu Ile Gln Arg Ala Gln Glu Ala Val Ala Glu<br>        195                 200                 205 | | 624 |
| tca agc aag aag acc cga cac cag aaa gcc gtg tgt agc tgt ggc tgc<br>Ser Ser Lys Lys Thr Arg His Gln Lys Ala Val Cys Ser Cys Gly Cys<br>    210                 215                 220 | | 672 |
| tct gta gcc tga<br>Ser Val Ala<br>225 | | 684 |

<210> SEQ ID NO 14
<211> LENGTH: 227
<212> TYPE: PRT

<213> ORGANISM: Mus musculus

<400> SEQUENCE: 14

```
Met Ala Leu Pro Thr Lys Ser Ser Ile Leu Asp Leu Ser Ser Gly Thr
1               5                   10                  15

Pro Cys Thr Arg Ser Pro Glu Glu Ser His Glu Ala Trp Ala Gln Cys
            20                  25                  30

Lys Asp Ala Gly Arg Gln Leu Pro Glu Tyr Lys Ala Val Val Val Gly
        35                  40                  45

Ala Ser Gly Val Gly Lys Ser Ala Leu Thr Ile Gln Met Thr His Gln
    50                  55                  60

Cys Phe Val Lys Asp His Asp Pro Thr Ile Gln Asp Ser Tyr Trp Lys
65                  70                  75                  80

Glu Val Ala Arg Asp Asn Gly Gly Tyr Ile Leu Asn Val Leu Asp Thr
                85                  90                  95

Ser Gly Gln Asp Ile His Arg Ala Leu Arg Asp Gln Cys Leu Ala Ser
            100                 105                 110

Gly Asp Gly Val Leu Gly Val Phe Ala Leu Asp Asp Pro Ser Ser Leu
        115                 120                 125

Asp Gln Leu Gln Gln Ile Trp Ser Thr Trp Pro His His Lys Gln
    130                 135                 140

Pro Leu Val Leu Val Gly Asn Lys Cys Asp Leu Val Thr Thr Ala Gly
145                 150                 155                 160

Asp Ala His Ala Ala Ala Leu Leu Ala His Lys Leu Gly Ala Pro
                165                 170                 175

Leu Val Lys Thr Ser Ala Lys Thr Arg Gln Gly Val Glu Glu Ala Phe
        180                 185                 190

Ala Leu Leu Val His Glu Ile Gln Arg Ala Gln Glu Ala Val Ala Glu
    195                 200                 205

Ser Ser Lys Lys Thr Arg His Gln Lys Ala Val Cys Ser Cys Gly Cys
    210                 215                 220

Ser Val Ala
225
```

<210> SEQ ID NO 15
<211> LENGTH: 702
<212> TYPE: DNA
<213> ORGANISM: Homo sapiens
<220> FEATURE:
<221> NAME/KEY: CDS
<222> LOCATION: (1)..(702)

<400> SEQUENCE: 15

```
atg gag ctg cca aca aag cct ggc acc ttc gac ctg ggc ctg gcc aca    48
Met Glu Leu Pro Thr Lys Pro Gly Thr Phe Asp Leu Gly Leu Ala Thr
1               5                   10                  15 tgg agc cct tcc ttc cag ggg gaa acc cac cgg gct cag gca cgc cgc    96
Trp Ser Pro Ser Phe Gln Gly Glu Thr His Arg Ala Gln Ala Arg Arg
            20                  25                  30 agg gat gtt ggc agg cag ctg cct gag tac aag gct gtg gtg gtg ggc   144
Arg Asp Val Gly Arg Gln Leu Pro Glu Tyr Lys Ala Val Val Val Gly
        35                  40                  45 gcc agt ggc gtg ggc aag agt gcg ctg acc atc cag ctg aac cac cag   192
Ala Ser Gly Val Gly Lys Ser Ala Leu Thr Ile Gln Leu Asn His Gln
    50                  55                  60 tgc ttc gtg gag gac cac gac ccc acc atc cag gat tcc tac tgg aag   240
Cys Phe Val Glu Asp His Asp Pro Thr Ile Gln Asp Ser Tyr Trp Lys
65                  70                  75                  80
```

```
gag ttg acc ctg gac agt ggg gac tgc att ctg aat gtg ctg gac aca        288
Glu Leu Thr Leu Asp Ser Gly Asp Cys Ile Leu Asn Val Leu Asp Thr
                 85                  90                  95 gca ggg cag gcc atc cat agg gcc ctg cgt gac cag tgc ctg gct gtc        336
Ala Gly Gln Ala Ile His Arg Ala Leu Arg Asp Gln Cys Leu Ala Val
            100                 105                 110 tgt gat ggt gtg ctg ggc gtc ttc gct ctc gat gac ccc tcg tct ctg        384
Cys Asp Gly Val Leu Gly Val Phe Ala Leu Asp Asp Pro Ser Ser Leu
        115                 120                 125 atc cag ctg cag cag ata tgg gcc acc tgg ggc cct cac ccc gcc cag        432
Ile Gln Leu Gln Gln Ile Trp Ala Thr Trp Gly Pro His Pro Ala Gln
    130                 135                 140 ccc ctt gtc ctc gtg ggc aac aag tgt gac ctt gtg acc act gct gga        480
Pro Leu Val Leu Val Gly Asn Lys Cys Asp Leu Val Thr Thr Ala Gly
145                 150                 155                 160 gat gct cat gcc gct gct gca gcc ctc gca cac agc tgg ggg gcc cac        528
Asp Ala His Ala Ala Ala Ala Leu Ala His Ser Trp Gly Ala His
                165                 170                 175 ttc gtg gag acc tcg gcc aaa aca cgg caa ggc gtg gag gag gcc ttt        576
Phe Val Glu Thr Ser Ala Lys Thr Arg Gln Gly Val Glu Glu Ala Phe
            180                 185                 190 tcc ctg ctg gtc cat gag atc cag agg gtc cag gag gcc atg gcg aag        624
Ser Leu Leu Val His Glu Ile Gln Arg Val Gln Glu Ala Met Ala Lys
        195                 200                 205 gag ccc atg gca agg tcc tgt agg gag aag acc cgg cac cag aag gcc        672
Glu Pro Met Ala Arg Ser Cys Arg Glu Lys Thr Arg His Gln Lys Ala
    210                 215                 220 acc tgc cac tgt ggc tgc tct gtg gcc tga                                702
Thr Cys His Cys Gly Cys Ser Val Ala
225                 230
```

<210> SEQ ID NO 16
<211> LENGTH: 233
<212> TYPE: PRT
<213> ORGANISM: Homo sapiens

<400> SEQUENCE: 16

```
Met Glu Leu Pro Thr Lys Pro Gly Thr Phe Asp Leu Gly Leu Ala Thr
1               5                   10                  15

Trp Ser Pro Ser Phe Gln Gly Glu Thr His Arg Ala Gln Ala Arg Arg
            20                  25                  30

Arg Asp Val Gly Arg Gln Leu Pro Glu Tyr Lys Ala Val Val Val Gly
        35                  40                  45

Ala Ser Gly Val Gly Lys Ser Ala Leu Thr Ile Gln Leu Asn His Gln
    50                  55                  60

Cys Phe Val Glu Asp His Asp Pro Thr Ile Gln Asp Ser Tyr Trp Lys
65                  70                  75                  80

Glu Leu Thr Leu Asp Ser Gly Asp Cys Ile Leu Asn Val Leu Asp Thr
                85                  90                  95

Ala Gly Gln Ala Ile His Arg Ala Leu Arg Asp Gln Cys Leu Ala Val
            100                 105                 110

Cys Asp Gly Val Leu Gly Val Phe Ala Leu Asp Asp Pro Ser Ser Leu
        115                 120                 125

Ile Gln Leu Gln Gln Ile Trp Ala Thr Trp Gly Pro His Pro Ala Gln
    130                 135                 140

Pro Leu Val Leu Val Gly Asn Lys Cys Asp Leu Val Thr Thr Ala Gly
145                 150                 155                 160
```

-continued

```
Asp Ala His Ala Ala Ala Ala Leu Ala His Ser Trp Gly Ala His
            165                 170                 175

Phe Val Glu Thr Ser Ala Lys Thr Arg Gln Gly Val Glu Glu Ala Phe
        180                 185                 190

Ser Leu Leu Val His Glu Ile Gln Arg Val Gln Glu Ala Met Ala Lys
    195                 200                 205

Glu Pro Met Ala Arg Ser Cys Arg Glu Lys Thr Arg His Gln Lys Ala
210                 215                 220

Thr Cys His Cys Gly Cys Ser Val Ala
225                 230
```

<210> SEQ ID NO 17
<211> LENGTH: 4
<212> TYPE: PRT
<213> ORGANISM: Artificial Sequence
<220> FEATURE:
<223> OTHER INFORMATION: C-terminal farnesylation signal sequence
<220> FEATURE:
<221> NAME/KEY: MISC_FEATURE
<222> LOCATION: (2)..(2)
<223> OTHER INFORMATION: Aliphatic amino acid
<220> FEATURE:
<221> NAME/KEY: MISC_FEATURE
<222> LOCATION: (3)..(3)
<223> OTHER INFORMATION: Aliphatic amino acid
<220> FEATURE:
<221> NAME/KEY: MISC_FEATURE
<222> LOCATION: (4)..(4)
<223> OTHER INFORMATION: Any amino acid

<400> SEQUENCE: 17

Cys Xaa Xaa Xaa
1

<210> SEQ ID NO 18
<211> LENGTH: 3207
<212> TYPE: DNA
<213> ORGANISM: Mus musculus
<220> FEATURE:
<221> NAME/KEY: CDS
<222> LOCATION: (1)..(3207)

<400> SEQUENCE: 18

```
atg cct cca cga cca tct tcg ggt gaa ctg tgg ggc atc cac ttg atg      48
Met Pro Pro Arg Pro Ser Ser Gly Glu Leu Trp Gly Ile His Leu Met
1               5                   10                  15 ccc cca cga atc cta gtg gaa tgt tta ctc ccc aat gga atg ata gtg      96
Pro Pro Arg Ile Leu Val Glu Cys Leu Leu Pro Asn Gly Met Ile Val
            20                  25                  30 act tta gaa tgc ctc cgt gag gcc aca ctc gtc acc atc aaa cat gaa     144
Thr Leu Glu Cys Leu Arg Glu Ala Thr Leu Val Thr Ile Lys His Glu
        35                  40                  45 ctg ttc aga gag gcc agg aaa tac cct ctc cat cag ctt ctg caa gac     192
Leu Phe Arg Glu Ala Arg Lys Tyr Pro Leu His Gln Leu Leu Gln Asp
    50                  55                  60 gaa act tct tac att ttc gta agt gtc acc caa gaa gca gaa agg gaa     240
Glu Thr Ser Tyr Ile Phe Val Ser Val Thr Gln Glu Ala Glu Arg Glu
65                  70                  75                  80 gaa ttt ttt gat gaa aca aga cga ctt tgt gac ctt cgg ctt ttt caa     288
Glu Phe Phe Asp Glu Thr Arg Arg Leu Cys Asp Leu Arg Leu Phe Gln
                85                  90                  95 ccc ttt tta aaa gtt att gaa cca gta ggc aac cgt gaa gaa aag atc     336
Pro Phe Leu Lys Val Ile Glu Pro Val Gly Asn Arg Glu Glu Lys Ile
            100                 105                 110
```

```
ctc aat cga gaa att ggt ttt gtt att ggc atg cca gtg tgt gaa ttt       384
Leu Asn Arg Glu Ile Gly Phe Val Ile Gly Met Pro Val Cys Glu Phe
        115                 120                 125 gat atg gtt aaa gat cca gaa gtc caa gac ttt cga agg aac att ctg       432
Asp Met Val Lys Asp Pro Glu Val Gln Asp Phe Arg Arg Asn Ile Leu
130                 135                 140 aat gtt tgc aaa gaa gct gtg gac ctg cgg gat ctc aac tcg cct cat       480
Asn Val Cys Lys Glu Ala Val Asp Leu Arg Asp Leu Asn Ser Pro His
145                 150                 155                 160 agc aga gca atg tat gtc tac cct cca aat gtc gag tct tcc cca gaa       528
Ser Arg Ala Met Tyr Val Tyr Pro Pro Asn Val Glu Ser Ser Pro Glu
                165                 170                 175 ctg cca aag cac atc tac aac aag tta gat aaa gga caa atc ata gtg       576
Leu Pro Lys His Ile Tyr Asn Lys Leu Asp Lys Gly Gln Ile Ile Val
            180                 185                 190 gtg att tgg gta ata gtc tct cca aac aac gac aag cag aag tac act       624
Val Ile Trp Val Ile Val Ser Pro Asn Asn Asp Lys Gln Lys Tyr Thr
        195                 200                 205 ctg aag atc aat cat gac tgt gtg cca gag caa gtc att gct gaa gcc       672
Leu Lys Ile Asn His Asp Cys Val Pro Glu Gln Val Ile Ala Glu Ala
210                 215                 220 atc agg aaa aag act cgg agc atg ttg ttg tcc tct gag cag ctg aaa       720
Ile Arg Lys Lys Thr Arg Ser Met Leu Leu Ser Ser Glu Gln Leu Lys
225                 230                 235                 240 ctc tgt gtc tta gaa tat cag ggc aag tat att ctg aaa gtg tgt ggc       768
Leu Cys Val Leu Glu Tyr Gln Gly Lys Tyr Ile Leu Lys Val Cys Gly
                245                 250                 255 tgt gac gaa tac ttc ctg gaa aag tac cct ctg agt cag tac aag tac       816
Cys Asp Glu Tyr Phe Leu Glu Lys Tyr Pro Leu Ser Gln Tyr Lys Tyr
            260                 265                 270 ata aga agc tgt ata atg ctg ggg agg atg ccc aac ttg atg ctg atg       864
Ile Arg Ser Cys Ile Met Leu Gly Arg Met Pro Asn Leu Met Leu Met
        275                 280                 285 gcc aaa gaa agc cta tac tct cag ctg ccg att gat agc ttc acc atg       912
Ala Lys Glu Ser Leu Tyr Ser Gln Leu Pro Ile Asp Ser Phe Thr Met
290                 295                 300 ccg tca tac tcc agg cgc atc tcc aca gcc aca ccc tac atg aat gga       960
Pro Ser Tyr Ser Arg Arg Ile Ser Thr Ala Thr Pro Tyr Met Asn Gly
305                 310                 315                 320 gag aca tct acg aaa tcc ctc tgg gtc ata aat agt gcg ctc aga ata      1008
Glu Thr Ser Thr Lys Ser Leu Trp Val Ile Asn Ser Ala Leu Arg Ile
                325                 330                 335 aaa att ctt tgt gca acc tat gta aat gta aat att cga gac att gat      1056
Lys Ile Leu Cys Ala Thr Tyr Val Asn Val Asn Ile Arg Asp Ile Asp
            340                 345                 350 aag atc tat gtt cga aca ggt atc tac cat gga gga gaa ccc tta tgt      1104
Lys Ile Tyr Val Arg Thr Gly Ile Tyr His Gly Gly Glu Pro Leu Cys
        355                 360                 365 gac aat gtg aac act caa aga gta cct tgt tcc aat cct agg tgg aat      1152
Asp Asn Val Asn Thr Gln Arg Val Pro Cys Ser Asn Pro Arg Trp Asn
370                 375                 380 gaa tgg ctg aat tat gat ata tac att cct gat ctt cct cgt gct gcg      1200
Glu Trp Leu Asn Tyr Asp Ile Tyr Ile Pro Asp Leu Pro Arg Ala Ala
385                 390                 395                 400 cgc ctt tgc ctt tca atc tgc tct gtt aaa ggc cga aag ggt gct aag      1248
Arg Leu Cys Leu Ser Ile Cys Ser Val Lys Gly Arg Lys Gly Ala Lys
                405                 410                 415 gag gag cac tgt ccg ttg gcc tgg gga aac ata aac ttg ttt gat tat      1296
Glu Glu His Cys Pro Leu Ala Trp Gly Asn Ile Asn Leu Phe Asp Tyr
            420                 425                 430
```

```
aca gac acc cta gtg tcc ggg aaa atg gct ttg aat ctc tgg cct gta      1344
Thr Asp Thr Leu Val Ser Gly Lys Met Ala Leu Asn Leu Trp Pro Val
            435                 440                 445 ccg cat ggg tta gaa gat ctg ctg aac cct att ggt gtt act ggg tca      1392
Pro His Gly Leu Glu Asp Leu Leu Asn Pro Ile Gly Val Thr Gly Ser
        450                 455                 460 aat cca aat aaa gaa act cca tgc tta gag ttg gag ttt gat tgg ttc      1440
Asn Pro Asn Lys Glu Thr Pro Cys Leu Glu Leu Glu Phe Asp Trp Phe
465                 470                 475                 480 agc agt gtg gtg aag ttt cca gac atg tct gtg atc gaa gaa cat gcc      1488
Ser Ser Val Val Lys Phe Pro Asp Met Ser Val Ile Glu Glu His Ala
                485                 490                 495 aat tgg tcc gtg tcc cga gaa gct gga ttc agt tac tcc cat aca gga      1536
Asn Trp Ser Val Ser Arg Glu Ala Gly Phe Ser Tyr Ser His Thr Gly
            500                 505                 510 ctg agt aac aga cta gcc aga gac aat gag tta aga gaa aat gac aag      1584
Leu Ser Asn Arg Leu Ala Arg Asp Asn Glu Leu Arg Glu Asn Asp Lys
        515                 520                 525 gaa cag ctc cga gca ctt tgc acc cgg gac cca cta tct gaa atc act      1632
Glu Gln Leu Arg Ala Leu Cys Thr Arg Asp Pro Leu Ser Glu Ile Thr
530                 535                 540 gaa caa gag aaa gac ttc cta tgg agc cac aga cac tac tgc gta act      1680
Glu Gln Glu Lys Asp Phe Leu Trp Ser His Arg His Tyr Cys Val Thr
545                 550                 555                 560 att cct gaa atc cta ccc aaa ttg ctt ctg tct gtc aag tgg aat tcc      1728
Ile Pro Glu Ile Leu Pro Lys Leu Leu Leu Ser Val Lys Trp Asn Ser
                565                 570                 575 aga gac gaa gtg gcc cag atg tac tgc tta gta aaa gat tgg cct cca      1776
Arg Asp Glu Val Ala Gln Met Tyr Cys Leu Val Lys Asp Trp Pro Pro
            580                 585                 590 atc aaa cca gag caa gcc atg gaa ctc ctg gac tgt aac tat cca gat      1824
Ile Lys Pro Glu Gln Ala Met Glu Leu Leu Asp Cys Asn Tyr Pro Asp
        595                 600                 605 cct atg gtt cgg agt ttt gct gtt cgg tgc tta gaa aaa tat tta aca      1872
Pro Met Val Arg Ser Phe Ala Val Arg Cys Leu Glu Lys Tyr Leu Thr
610                 615                 620 gat gac aaa ctt tct cag tac ctc att caa ctt gta cag gtc tta aaa      1920
Asp Asp Lys Leu Ser Gln Tyr Leu Ile Gln Leu Val Gln Val Leu Lys
625                 630                 635                 640 tat gaa cag tat ttg gat aac ctg ctt gtg aga ttt tta ctc aag aaa      1968
Tyr Glu Gln Tyr Leu Asp Asn Leu Leu Val Arg Phe Leu Leu Lys Lys
                645                 650                 655 gca ttg aca aat caa agg att ggc cat ttt ttc ttt tgg cat tta aaa      2016
Ala Leu Thr Asn Gln Arg Ile Gly His Phe Phe Phe Trp His Leu Lys
            660                 665                 670 tct gag atg cac aat aag act gtc agt cag agg ttt ggc ctg cta ttg      2064
Ser Glu Met His Asn Lys Thr Val Ser Gln Arg Phe Gly Leu Leu Leu
        675                 680                 685 gag tcc tac tgc cgt gcc tgt ggg atg tat ctg aag cac ctg aac aga      2112
Glu Ser Tyr Cys Arg Ala Cys Gly Met Tyr Leu Lys His Leu Asn Arg
690                 695                 700 caa gta gag gcc atg gag aag ctc atc aac cta acg gac atc ctt aag      2160
Gln Val Glu Ala Met Glu Lys Leu Ile Asn Leu Thr Asp Ile Leu Lys
705                 710                 715                 720 cag gag aag aag gat gag aca caa aag gta cag atg aag ttt ctg gtt      2208
Gln Glu Lys Lys Asp Glu Thr Gln Lys Val Gln Met Lys Phe Leu Val
                725                 730                 735 gaa cag atg aga cag cca gac ttc atg gat gct ttg cag ggt ttt ctg      2256
Glu Gln Met Arg Gln Pro Asp Phe Met Asp Ala Leu Gln Gly Phe Leu
```

-continued

| | | |
|---|---|---|
| tcc cct ctg aat cct gct cac caa cta gga aac ctc agg ctt gaa gag<br>Ser Pro Leu Asn Pro Ala His Gln Leu Gly Asn Leu Arg Leu Glu Glu<br>755                      760                      765 | 2304 |
| tgt cga att atg tcc tct gca aaa agg cca ctg tgg ttg aat tgg gag<br>Cys Arg Ile Met Ser Ser Ala Lys Arg Pro Leu Trp Leu Asn Trp Glu<br>770                      775                      780 | 2352 |
| aac cca gac atc atg tca gag cta ctg ttt cag aac aat gag atc atc<br>Asn Pro Asp Ile Met Ser Glu Leu Leu Phe Gln Asn Asn Glu Ile Ile<br>785                      790                      795                      800 | 2400 |
| ttt aaa aat ggc gac gac tta cgg caa gat atg tta acc ctt cag atc<br>Phe Lys Asn Gly Asp Asp Leu Arg Gln Asp Met Leu Thr Leu Gln Ile<br>                      805                      810 | 2448 |
| atc cga atc atg gag aac atc tgg caa aac caa ggc ctt gac ctt cgc<br>Ile Arg Ile Met Glu Asn Ile Trp Gln Asn Gln Gly Leu Asp Leu Arg<br>        820                      825                      830 | 2496 |
| atg cta cct tat ggc tgt cta tcc att ggg gac tgt gtg ggt ctc atc<br>Met Leu Pro Tyr Gly Cys Leu Ser Ile Gly Asp Cys Val Gly Leu Ile<br>        835                      840                      845 | 2544 |
| gag gtg gtg aga aac tct cac acc atc atg caa atc cag tgc aaa gga<br>Glu Val Val Arg Asn Ser His Thr Ile Met Gln Ile Gln Cys Lys Gly<br>850                      855                      860 | 2592 |
| ggc ctg aag ggg gcg ctg cag ttc aac agc cac aca ctg cat caa tgg<br>Gly Leu Lys Gly Ala Leu Gln Phe Asn Ser His Thr Leu His Gln Trp<br>865                      870                      875                      880 | 2640 |
| ctc aag gac aag aac aag ggc gag ata tat gat gca gcc att gac ctg<br>Leu Lys Asp Lys Asn Lys Gly Glu Ile Tyr Asp Ala Ala Ile Asp Leu<br>                      885                      890                      895 | 2688 |
| ttc act cgg tcc tgc gct ggg tac tgc gtg gca acc ttt atc ttg gga<br>Phe Thr Arg Ser Cys Ala Gly Tyr Cys Val Ala Thr Phe Ile Leu Gly<br>        900                      905                      910 | 2736 |
| att gga gac cgg cac aac agc aac atc atg gtg aaa gat gac gga cag<br>Ile Gly Asp Arg His Asn Ser Asn Ile Met Val Lys Asp Asp Gly Gln<br>        915                      920                      925 | 2784 |
| ctg ttt cat ata gat ttt ggg cac ttt ttg gat cac aag aag aaa aaa<br>Leu Phe His Ile Asp Phe Gly His Phe Leu Asp His Lys Lys Lys Lys<br>930                      935                      940 | 2832 |
| ttt ggc tat aag cgg gaa cgt gtg cca ttt gtg ttg aca cag gat ttc<br>Phe Gly Tyr Lys Arg Glu Arg Val Pro Phe Val Leu Thr Gln Asp Phe<br>945                      950                      955                      960 | 2880 |
| ttg att gtg att agt aag gga gca caa gag tac acc aag acc aga gag<br>Leu Ile Val Ile Ser Lys Gly Ala Gln Glu Tyr Thr Lys Thr Arg Glu<br>                      965                      970                      975 | 2928 |
| ttt gag agg ttt cag gag atg tgt tac aag gct tac cta gca att cgg<br>Phe Glu Arg Phe Gln Glu Met Cys Tyr Lys Ala Tyr Leu Ala Ile Arg<br>        980                      985                      990 | 2976 |
| cag cat gcc aat ctc ttc atc aac ctt ttt tca atg atg ctt ggc tct<br>Gln His Ala Asn Leu Phe Ile Asn Leu Phe Ser Met Met Leu Gly Ser<br>        995                      1000                    1005 | 3024 |
| gga atg cca gaa cta caa tct ttt gat gac att gca tat atc cga<br>Gly Met Pro Glu Leu Gln Ser Phe Asp Asp Ile Ala Tyr Ile Arg<br>        1010                      1015                    1020 | 3069 |
| aag act cta gcc ttg gac aaa act gag caa gaa gct ttg gaa tat<br>Lys Thr Leu Ala Leu Asp Lys Thr Glu Gln Glu Ala Leu Glu Tyr<br>        1025                      1030                    1035 | 3114 |
| ttc aca aag caa atg aat gat gca cat cat ggt gga tgg acg aca<br>Phe Thr Lys Gln Met Asn Asp Ala His His Gly Gly Trp Thr Thr<br>        1040                      1045                    1050 | 3159 |
| aaa atg gat tgg atc ttc cac acc atc aag cag cat gct ttg aac | 3204 |

Lys Met Asp Trp Ile Phe His Thr Ile Lys Gln His Ala Leu Asn
1055                1060                1065 tga                                                              3207

<210> SEQ ID NO 19
<211> LENGTH: 1068
<212> TYPE: PRT
<213> ORGANISM: Mus musculus

<400> SEQUENCE: 19

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Val Thr Ile Lys His Glu
        35                  40                  45

Leu Phe Arg Glu Ala Arg Lys Tyr Pro Leu His Gln Leu Leu Gln Asp
    50                  55                  60

Glu Thr Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Val Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Ile Asp Ser Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

-continued

Lys Ile Tyr Val Arg Thr Gly Ile Tyr His Gly Gly Glu Pro Leu Cys
         355                 360                 365

Asp Asn Val Asn Thr Gln Arg Val Pro Cys Ser Asn Pro Arg Trp Asn
         370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                 405                 410                 415

Glu Glu His Cys Pro Leu Ala Trp Gly Asn Ile Asn Leu Phe Asp Tyr
         420                 425                 430

Thr Asp Thr Leu Val Ser Gly Lys Met Ala Leu Asn Leu Trp Pro Val
         435                 440                 445

Pro His Gly Leu Glu Asp Leu Leu Asn Pro Ile Gly Val Thr Gly Ser
         450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                 485                 490                 495

Asn Trp Ser Val Ser Arg Glu Ala Gly Phe Ser Tyr Ser His Thr Gly
                 500                 505                 510

Leu Ser Asn Arg Leu Ala Arg Asp Asn Glu Leu Arg Glu Asn Asp Lys
         515                 520                 525

Glu Gln Leu Arg Ala Leu Cys Thr Arg Asp Pro Leu Ser Glu Ile Thr
         530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                 565                 570                 575

Arg Asp Glu Val Ala Gln Met Tyr Cys Leu Val Lys Asp Trp Pro Pro
                 580                 585                 590

Ile Lys Pro Glu Gln Ala Met Glu Leu Leu Asp Cys Asn Tyr Pro Asp
                 595                 600                 605

Pro Met Val Arg Ser Phe Ala Val Arg Cys Leu Glu Lys Tyr Leu Thr
610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                 645                 650                 655

Ala Leu Thr Asn Gln Arg Ile Gly His Phe Phe Phe Trp His Leu Lys
         660                 665                 670

Ser Glu Met His Asn Lys Thr Val Ser Gln Arg Phe Gly Leu Leu Leu
         675                 680                 685

Glu Ser Tyr Cys Arg Ala Cys Gly Met Tyr Leu Lys His Leu Asn Arg
         690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                 725                 730                 735

Glu Gln Met Arg Gln Pro Asp Phe Met Asp Ala Leu Gln Gly Phe Leu
         740                 745                 750

Ser Pro Leu Asn Pro Ala His Gln Leu Gly Asn Leu Arg Leu Glu Glu
         755                 760                 765

Cys Arg Ile Met Ser Ser Ala Lys Arg Pro Leu Trp Leu Asn Trp Glu

```
                770               775               780
Asn Pro Asp Ile Met Ser Glu Leu Leu Phe Gln Asn Asn Glu Ile Ile
785               790               795               800

Phe Lys Asn Gly Asp Asp Leu Arg Gln Asp Met Leu Thr Leu Gln Ile
            805               810               815

Ile Arg Ile Met Glu Asn Ile Trp Gln Asn Gln Gly Leu Asp Leu Arg
            820               825               830

Met Leu Pro Tyr Gly Cys Leu Ser Ile Gly Asp Cys Val Gly Leu Ile
            835               840               845

Glu Val Val Arg Asn Ser His Thr Ile Met Gln Ile Gln Cys Lys Gly
        850               855               860

Gly Leu Lys Gly Ala Leu Gln Phe Asn Ser His Thr Leu His Gln Trp
865               870               875               880

Leu Lys Asp Lys Asn Lys Gly Glu Ile Tyr Asp Ala Ala Ile Asp Leu
            885               890               895

Phe Thr Arg Ser Cys Ala Gly Tyr Cys Val Ala Thr Phe Ile Leu Gly
            900               905               910

Ile Gly Asp Arg His Asn Ser Asn Ile Met Val Lys Asp Asp Gly Gln
            915               920               925

Leu Phe His Ile Asp Phe Gly His Phe Leu Asp His Lys Lys Lys Lys
            930               935               940

Phe Gly Tyr Lys Arg Glu Arg Val Pro Phe Val Leu Thr Gln Asp Phe
945               950               955               960

Leu Ile Val Ile Ser Lys Gly Ala Gln Glu Tyr Thr Lys Thr Arg Glu
            965               970               975

Phe Glu Arg Phe Gln Glu Met Cys Tyr Lys Ala Tyr Leu Ala Ile Arg
            980               985               990

Gln His Ala Asn Leu Phe Ile Asn  Leu Phe Ser Met Met  Leu Gly Ser
            995              1000              1005

Gly Met  Pro Glu Leu Gln Ser  Phe Asp Asp Ile Ala  Tyr Ile Arg
    1010              1015              1020

Lys Thr  Leu Ala Leu Asp Lys  Thr Glu Gln Glu Ala  Leu Glu Tyr
    1025              1030              1035

Phe Thr  Lys Gln Met Asn Asp  Ala His His Gly Gly  Trp Thr Thr
    1040              1045              1050

Lys Met  Asp Trp Ile Phe His  Thr Ile Lys Gln His  Ala Leu Asn
    1055              1060              1065

<210> SEQ ID NO 20
<211> LENGTH: 3207
<212> TYPE: DNA
<213> ORGANISM: Homo sapiens
<220> FEATURE:
<221> NAME/KEY: CDS
<222> LOCATION: (1)..(3207)

<400> SEQUENCE: 20 atg cct cca cga cca tca tca ggt gaa ctg tgg ggc atc cac ttg atg    48
Met Pro Pro Arg Pro Ser Ser Gly Glu Leu Trp Gly Ile His Leu Met
1               5                  10                  15 ccc cca aga atc cta gta gaa tgt tta cta cca aat gga atg ata gtg    96
Pro Pro Arg Ile Leu Val Glu Cys Leu Leu Pro Asn Gly Met Ile Val
            20                  25                  30 act tta gaa tgc ctc cgt gag gct aca tta ata acc ata aag cat gaa   144
Thr Leu Glu Cys Leu Arg Glu Ala Thr Leu Ile Thr Ile Lys His Glu
        35                  40                  45
```

```
cta ttt aaa gaa gca aga aaa tac ccc ctc cat caa ctt ctt caa gat      192
Leu Phe Lys Glu Ala Arg Lys Tyr Pro Leu His Gln Leu Leu Gln Asp
    50              55                  60 gaa tct tct tac att ttc gta agt gtt act caa gaa gca gaa agg gaa      240
Glu Ser Ser Tyr Ile Phe Val Ser Val Thr Gln Glu Ala Glu Arg Glu
65              70                  75                  80 gaa ttt ttt gat gaa aca aga cga ctt tgt gac ctt cgg ctt ttt caa      288
Glu Phe Phe Asp Glu Thr Arg Arg Leu Cys Asp Leu Arg Leu Phe Gln
                    85                  90                  95 ccc ttt tta aaa gta att gaa cca gta ggc aac cgt gaa gaa aag atc      336
Pro Phe Leu Lys Val Ile Glu Pro Val Gly Asn Arg Glu Glu Lys Ile
                100                 105                 110 ctc aat cga gaa att ggt ttt gct atc ggc atg cca gtg tgt gaa ttt      384
Leu Asn Arg Glu Ile Gly Phe Ala Ile Gly Met Pro Val Cys Glu Phe
            115                 120                 125 gat atg gtt aaa gat cca gaa gta cag gac ttc cga aga aat att ctg      432
Asp Met Val Lys Asp Pro Glu Val Gln Asp Phe Arg Arg Asn Ile Leu
        130                 135                 140 aac gtt tgt aaa gaa gct gtg gat ctt agg gac ctc aat tca cct cat      480
Asn Val Cys Lys Glu Ala Val Asp Leu Arg Asp Leu Asn Ser Pro His
145                 150                 155                 160 agt aga gca atg tat gtc tat cct cca aat gta gaa tct tca cca gaa      528
Ser Arg Ala Met Tyr Val Tyr Pro Pro Asn Val Glu Ser Ser Pro Glu
                165                 170                 175 ttg cca aag cac ata tat aat aaa tta gat aaa ggg caa ata ata gtg      576
Leu Pro Lys His Ile Tyr Asn Lys Leu Asp Lys Gly Gln Ile Ile Val
                180                 185                 190 gtg atc tgg gta ata gtt tct cca aat aat gac aag cag aag tat act      624
Val Ile Trp Val Ile Val Ser Pro Asn Asn Asp Lys Gln Lys Tyr Thr
            195                 200                 205 ctg aaa atc aac cat gac tgt gta cca gaa caa gta att gct gaa gca      672
Leu Lys Ile Asn His Asp Cys Val Pro Glu Gln Val Ile Ala Glu Ala
        210                 215                 220 atc agg aaa aaa act cga agt atg ttg cta tcc tct gaa caa cta aaa      720
Ile Arg Lys Lys Thr Arg Ser Met Leu Leu Ser Ser Glu Gln Leu Lys
225                 230                 235                 240 ctc tgt gtt tta gaa tat cag ggc aag tat att tta aaa gtg tgt gga      768
Leu Cys Val Leu Glu Tyr Gln Gly Lys Tyr Ile Leu Lys Val Cys Gly
                245                 250                 255 tgt gat gaa tac ttc cta gaa aaa tat cct ctg agt cag tat aag tat      816
Cys Asp Glu Tyr Phe Leu Glu Lys Tyr Pro Leu Ser Gln Tyr Lys Tyr
                260                 265                 270 ata aga agc tgt ata atg ctt ggg agg atg ccc aat ttg atg ttg atg      864
Ile Arg Ser Cys Ile Met Leu Gly Arg Met Pro Asn Leu Met Leu Met
            275                 280                 285 gct aaa gaa agc ctt tat tct caa ctg cca atg gac tgt ttt aca atg      912
Ala Lys Glu Ser Leu Tyr Ser Gln Leu Pro Met Asp Cys Phe Thr Met
        290                 295                 300 cca tct tat tcc aga cgc att tcc aca gct aca cca tat atg aat gga      960
Pro Ser Tyr Ser Arg Arg Ile Ser Thr Ala Thr Pro Tyr Met Asn Gly
305                 310                 315                 320 gaa aca tct aca aaa tcc ctt tgg gtt ata aat agt gca ctc aga ata     1008
Glu Thr Ser Thr Lys Ser Leu Trp Val Ile Asn Ser Ala Leu Arg Ile
                325                 330                 335 aaa att ctt tgt gca acc tac gtg aat gta aat att cga gac att gat     1056
Lys Ile Leu Cys Ala Thr Tyr Val Asn Val Asn Ile Arg Asp Ile Asp
                340                 345                 350 aag atc tat gtt cga aca ggt atc tac cat gga gga gaa ccc tta tgt     1104
Lys Ile Tyr Val Arg Thr Gly Ile Tyr His Gly Gly Glu Pro Leu Cys
            355                 360                 365
```

| | |
|---|---|
| gac aat gtg aac act caa aga gta cct tgt tcc aat ccc agg tgg aat<br>Asp Asn Val Asn Thr Gln Arg Val Pro Cys Ser Asn Pro Arg Trp Asn<br>370 375 380 | 1152 |
| gaa tgg ctg aat tat gat ata tac att cct gat ctt cct cgt gct gct<br>Glu Trp Leu Asn Tyr Asp Ile Tyr Ile Pro Asp Leu Pro Arg Ala Ala<br>385 390 395 400 | 1200 |
| cga ctt tgc ctt tcc att tgc tct gtt aaa ggc cga aag ggt gct aaa<br>Arg Leu Cys Leu Ser Ile Cys Ser Val Lys Gly Arg Lys Gly Ala Lys<br>405 410 415 | 1248 |
| gag gaa cac tgt cca ttg gca tgg gga aat ata aac ttg ttt gat tac<br>Glu Glu His Cys Pro Leu Ala Trp Gly Asn Ile Asn Leu Phe Asp Tyr<br>420 425 430 | 1296 |
| aca gac act cta gta tct gga aaa atg gct ttg aat ctt tgg cca gta<br>Thr Asp Thr Leu Val Ser Gly Lys Met Ala Leu Asn Leu Trp Pro Val<br>435 440 445 | 1344 |
| cct cat gga tta gaa gat ttg ctg aac cct att ggt gtt act gga tca<br>Pro His Gly Leu Glu Asp Leu Leu Asn Pro Ile Gly Val Thr Gly Ser<br>450 455 460 | 1392 |
| aat cca aat aaa gaa act cca tgc tta gag ttg gag ttt gac tgg ttc<br>Asn Pro Asn Lys Glu Thr Pro Cys Leu Glu Leu Glu Phe Asp Trp Phe<br>465 470 475 480 | 1440 |
| agc agt gtg gta aag ttc cca gat atg tca gtg att gaa gag cat gcc<br>Ser Ser Val Val Lys Phe Pro Asp Met Ser Val Ile Glu Glu His Ala<br>485 490 495 | 1488 |
| aat tgg tct gta tcc cga gaa gca gga ttt agc tat tcc cac gca gga<br>Asn Trp Ser Val Ser Arg Glu Ala Gly Phe Ser Tyr Ser His Ala Gly<br>500 505 510 | 1536 |
| ctg agt aac aga cta gct aga gac aat gaa tta agg gaa aat gac aaa<br>Leu Ser Asn Arg Leu Ala Arg Asp Asn Glu Leu Arg Glu Asn Asp Lys<br>515 520 525 | 1584 |
| gaa cag ctc aaa gca att tct aca cga gat cct ctc tct gaa atc act<br>Glu Gln Leu Lys Ala Ile Ser Thr Arg Asp Pro Leu Ser Glu Ile Thr<br>530 535 540 | 1632 |
| gag cag gag aaa gat ttt cta tgg agt cac aga cac tat tgt gta act<br>Glu Gln Glu Lys Asp Phe Leu Trp Ser His Arg His Tyr Cys Val Thr<br>545 550 555 560 | 1680 |
| atc ccc gaa att cta ccc aaa ttg ctt ctg tct gtt aaa tgg aat tct<br>Ile Pro Glu Ile Leu Pro Lys Leu Leu Leu Ser Val Lys Trp Asn Ser<br>565 570 575 | 1728 |
| aga gat gaa gta gcc cag atg tat tgc ttg gta aaa gat tgg cct cca<br>Arg Asp Glu Val Ala Gln Met Tyr Cys Leu Val Lys Asp Trp Pro Pro<br>580 585 590 | 1776 |
| atc aaa cct gaa cag gct atg gaa ctt ctg gac tgt aat tac cca gat<br>Ile Lys Pro Glu Gln Ala Met Glu Leu Leu Asp Cys Asn Tyr Pro Asp<br>595 600 605 | 1824 |
| cct atg gtt cga ggt ttt gct gtt cgg tgc ttg gaa aaa tat tta aca<br>Pro Met Val Arg Gly Phe Ala Val Arg Cys Leu Glu Lys Tyr Leu Thr<br>610 615 620 | 1872 |
| gat gac aaa ctt tct cag tat tta att cag cta gta cag gtc cta aaa<br>Asp Asp Lys Leu Ser Gln Tyr Leu Ile Gln Leu Val Gln Val Leu Lys<br>625 630 635 640 | 1920 |
| tat gaa caa tat ttg gat aac ttg ctt gtg aga ttt tta ctg aag aaa<br>Tyr Glu Gln Tyr Leu Asp Asn Leu Leu Val Arg Phe Leu Leu Lys Lys<br>645 650 655 | 1968 |
| gca ttg act aat caa agg att ggg cac ttt ttc ttt tgg cat tta aaa<br>Ala Leu Thr Asn Gln Arg Ile Gly His Phe Phe Phe Trp His Leu Lys<br>660 665 670 | 2016 |
| tct gag atg cac aat aaa aca gtt agc cag agg ttt ggc ctg ctt ttg<br>Ser Glu Met His Asn Lys Thr Val Ser Gln Arg Phe Gly Leu Leu Leu | 2064 |

-continued

```
            675                 680                 685
gag tcc tat tgt cgt gca tgt ggg atg tat ttg aag cac ctg aat agg      2112
Glu Ser Tyr Cys Arg Ala Cys Gly Met Tyr Leu Lys His Leu Asn Arg
    690                 695                 700 caa gtc gag gca atg gaa aag ctc att aac tta act gac att ctc aaa      2160
Gln Val Glu Ala Met Glu Lys Leu Ile Asn Leu Thr Asp Ile Leu Lys
705                 710                 715                 720 cag gag aag aag gat gaa aca caa aag gta cag atg aag ttt tta gtt      2208
Gln Glu Lys Lys Asp Glu Thr Gln Lys Val Gln Met Lys Phe Leu Val
            725                 730                 735 gag caa atg agg cga cca gat ttc atg gat gct cta cag ggc ttt ctg      2256
Glu Gln Met Arg Arg Pro Asp Phe Met Asp Ala Leu Gln Gly Phe Leu
                740                 745                 750 tct cct cta aac cct gct cat caa cta gga aac ctc agg ctt gaa gag      2304
Ser Pro Leu Asn Pro Ala His Gln Leu Gly Asn Leu Arg Leu Glu Glu
                    755                 760                 765 tgt cga att atg tcc tct gca aaa agg cca ctg tgg ttg aat tgg gag      2352
Cys Arg Ile Met Ser Ser Ala Lys Arg Pro Leu Trp Leu Asn Trp Glu
770                 775                 780 aac cca gac atc atg tca gag tta ctg ttt cag aac aat gag atc atc      2400
Asn Pro Asp Ile Met Ser Glu Leu Leu Phe Gln Asn Asn Glu Ile Ile
785                 790                 795                 800 ttt aaa aat ggg gat gat tta cgg caa gat atg cta aca ctt caa att      2448
Phe Lys Asn Gly Asp Asp Leu Arg Gln Asp Met Leu Thr Leu Gln Ile
                    805                 810                 815 att cgt att atg gaa aat atc tgg caa aat caa ggt ctt gat ctt cga      2496
Ile Arg Ile Met Glu Asn Ile Trp Gln Asn Gln Gly Leu Asp Leu Arg
                820                 825                 830 atg tta cct tat ggt tgt ctg tca atc ggt gac tgt gtg gga ctt att      2544
Met Leu Pro Tyr Gly Cys Leu Ser Ile Gly Asp Cys Val Gly Leu Ile
                    835                 840                 845 gag gtg gtg cga aat tct cac act att atg caa att cag tgc aaa ggc      2592
Glu Val Val Arg Asn Ser His Thr Ile Met Gln Ile Gln Cys Lys Gly
850                 855                 860 ggc ttg aaa ggt gca ctg cag ttc aac agc cac aca cta cat cag tgg      2640
Gly Leu Lys Gly Ala Leu Gln Phe Asn Ser His Thr Leu His Gln Trp
865                 870                 875                 880 ctc aaa gac aag aac aaa gga gaa ata tat gat gca gcc att gac ctg      2688
Leu Lys Asp Lys Asn Lys Gly Glu Ile Tyr Asp Ala Ala Ile Asp Leu
                    885                 890                 895 ttt aca cgt tca tgt gct gga tac tgt gta gct acc ttc att ttg gga      2736
Phe Thr Arg Ser Cys Ala Gly Tyr Cys Val Ala Thr Phe Ile Leu Gly
                900                 905                 910 att gga gat cgt cac aat agt aac atc atg gtg aaa gac gat gga caa      2784
Ile Gly Asp Arg His Asn Ser Asn Ile Met Val Lys Asp Asp Gly Gln
            915                 920                 925 ctg ttt cat ata gat ttt gga cac ttt ttg gat cac aag aag aaa aaa      2832
Leu Phe His Ile Asp Phe Gly His Phe Leu Asp His Lys Lys Lys Lys
930                 935                 940 ttt ggt tat aaa cga gaa cgt gtg cca ttt gtt ttg aca cag gat ttc      2880
Phe Gly Tyr Lys Arg Glu Arg Val Pro Phe Val Leu Thr Gln Asp Phe
945                 950                 955                 960 tta ata gtg att agt aaa gga gcc caa gaa tgc aca aag aca aga gaa      2928
Leu Ile Val Ile Ser Lys Gly Ala Gln Glu Cys Thr Lys Thr Arg Glu
                    965                 970                 975 ttt gag agg ttt cag gag atg tgt tac aag gct tat cta gct att cga      2976
Phe Glu Arg Phe Gln Glu Met Cys Tyr Lys Ala Tyr Leu Ala Ile Arg
                980                 985                 990 cag cat gcc aat ctc ttc ata aat  ctt ttc tca atg atg  ctt ggc tct     3024
```

-continued

```
                Gln His Ala Asn Leu Phe Ile Asn Leu Phe Ser Met Met Leu Gly Ser
                    995                 1000                1005 gga atg cca gaa cta caa tct ttt gat gac att gca tac att cga       3069
Gly Met Pro Glu Leu Gln Ser Phe Asp Asp Ile Ala Tyr Ile Arg
    1010                1015                1020 aag acc cta gcc tta gat aaa act gag caa gag gct ttg gag tat       3114
Lys Thr Leu Ala Leu Asp Lys Thr Glu Gln Glu Ala Leu Glu Tyr
    1025                1030                1035 ttc atg aaa caa atg aat gat gca cat cat ggt ggc tgg aca aca       3159
Phe Met Lys Gln Met Asn Asp Ala His His Gly Gly Trp Thr Thr
    1040                1045                1050 aaa atg gat tgg atc ttc cac aca att aaa cag cat gca ttg aac       3204
Lys Met Asp Trp Ile Phe His Thr Ile Lys Gln His Ala Leu Asn
    1055                1060                1065 tga                                                               3207

<210> SEQ ID NO 21
<211> LENGTH: 1068
<212> TYPE: PRT
<213> ORGANISM: Homo sapiens

<400> SEQUENCE: 21

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
                260                 265                 270
```

```
Ile Arg Ser Cys Ile Met Leu Gly Arg Met Pro Asn Leu Met Leu Met
            275                 280                 285

Ala Lys Glu Ser Leu Tyr Ser Gln Leu Pro Met Asp Cys Phe Thr Met
        290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
                340                 345                 350

Lys Ile Tyr Val Arg Thr Gly Ile Tyr His Gly Gly Glu Pro Leu Cys
            355                 360                 365

Asp Asn Val Asn Thr Gln Arg Val Pro Cys Ser Asn Pro Arg Trp Asn
370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
            435                 440                 445

Pro His Gly Leu Glu Asp Leu Leu Asn Pro Ile Gly Val Thr Gly Ser
        450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
        530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
                580                 585                 590

Ile Lys Pro Glu Gln Ala Met Glu Leu Leu Asp Cys Asn Tyr Pro Asp
            595                 600                 605

Pro Met Val Arg Gly Phe Ala Val Arg Cys Leu Glu Lys Tyr Leu Thr
        610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
            675                 680                 685
```

```
Glu Ser Tyr Cys Arg Ala Cys Gly Met Tyr Leu Lys His Leu Asn Arg
    690             695                 700
Gln Val Glu Ala Met Lys Leu Ile Asn Leu Thr Asp Ile Leu Lys
705             710                 715                 720
Gln Glu Lys Lys Asp Glu Thr Gln Lys Val Gln Met Lys Phe Leu Val
                725                 730                 735
Glu Gln Met Arg Arg Pro Asp Phe Met Asp Ala Leu Gln Gly Phe Leu
                740                 745                 750
Ser Pro Leu Asn Pro Ala His Gln Leu Gly Asn Leu Arg Leu Glu Glu
            755                 760                 765
Cys Arg Ile Met Ser Ser Ala Lys Arg Pro Leu Trp Leu Asn Trp Glu
770                 775                 780
Asn Pro Asp Ile Met Ser Glu Leu Leu Phe Gln Asn Asn Glu Ile Ile
785                 790                 795                 800
Phe Lys Asn Gly Asp Asp Leu Arg Gln Asp Met Leu Thr Leu Gln Ile
                805                 810                 815
Ile Arg Ile Met Glu Asn Ile Trp Gln Asn Gln Gly Leu Asp Leu Arg
                820                 825                 830
Met Leu Pro Tyr Gly Cys Leu Ser Ile Gly Asp Cys Val Gly Leu Ile
            835                 840                 845
Glu Val Val Arg Asn Ser His Thr Ile Met Gln Ile Gln Cys Lys Gly
850                 855                 860
Gly Leu Lys Gly Ala Leu Gln Phe Asn Ser His Thr Leu His Gln Trp
865                 870                 875                 880
Leu Lys Asp Lys Asn Lys Gly Glu Ile Tyr Asp Ala Ala Ile Asp Leu
                885                 890                 895
Phe Thr Arg Ser Cys Ala Gly Tyr Cys Val Ala Thr Phe Ile Leu Gly
            900                 905                 910
Ile Gly Asp Arg His Asn Ser Asn Ile Met Val Lys Asp Asp Gly Gln
            915                 920                 925
Leu Phe His Ile Asp Phe Gly His Phe Leu Asp His Lys Lys Lys Lys
            930                 935                 940
Phe Gly Tyr Lys Arg Glu Arg Val Pro Phe Val Leu Thr Gln Asp Phe
945                 950                 955                 960
Leu Ile Val Ile Ser Lys Gly Ala Gln Glu Cys Thr Lys Thr Arg Glu
                965                 970                 975
Phe Glu Arg Phe Gln Glu Met Cys Tyr Lys Ala Tyr Leu Ala Ile Arg
                980                 985                 990
Gln His Ala Asn Leu Phe Ile Asn Leu Phe Ser Met Met Leu Gly Ser
            995                 1000                1005
Gly Met Pro Glu Leu Gln Ser Phe Asp Asp Ile Ala Tyr Ile Arg
    1010                1015                1020
Lys Thr Leu Ala Leu Asp Lys Thr Glu Gln Glu Ala Leu Glu Tyr
    1025                1030                1035
Phe Met Lys Gln Met Asn Asp Ala His His Gly Gly Trp Thr Thr
    1040                1045                1050
Lys Met Asp Trp Ile Phe His Thr Ile Lys Gln His Ala Leu Asn
    1055                1060                1065

<210> SEQ ID NO 22
<211> LENGTH: 2559
<212> TYPE: DNA
<213> ORGANISM: Mus musculus
<220> FEATURE:
<221> NAME/KEY: CDS
```

<222> LOCATION: (1)..(2559)

<400> SEQUENCE: 22

| | | | | | | | | | | | | | | | | |
|---|---|---|---|---|---|---|---|---|---|---|---|---|---|---|---|---|
| atg | atg | gta | gat | tgc | cag | agc | tcc | acg | cag | gag | att | ggg | gag | gag | ctg | 48 |
| Met | Met | Val | Asp | Cys | Gln | Ser | Ser | Thr | Gln | Glu | Ile | Gly | Glu | Glu | Leu | |
| 1 | | | | 5 | | | | | 10 | | | | | 15 | | |
| atc | aac | ggg | gtc | atc | tac | tcc | atc | tcc | ctg | cgc | aag | gtc | cag | cta | cac | 96 |
| Ile | Asn | Gly | Val | Ile | Tyr | Ser | Ile | Ser | Leu | Arg | Lys | Val | Gln | Leu | His | |
| | | | 20 | | | | | 25 | | | | | 30 | | | |
| caa | gga | gcc | act | aag | ggc | cag | cgc | tgg | cta | ggg | tgt | gag | aac | gag | tcg | 144 |
| Gln | Gly | Ala | Thr | Lys | Gly | Gln | Arg | Trp | Leu | Gly | Cys | Glu | Asn | Glu | Ser | |
| | | | | 35 | | | | 40 | | | | | 45 | | | |
| gct | ctg | aac | ctc | tat | gag | acc | tgc | aag | gtg | cgc | acg | gtg | aag | gct | ggt | 192 |
| Ala | Leu | Asn | Leu | Tyr | Glu | Thr | Cys | Lys | Val | Arg | Thr | Val | Lys | Ala | Gly | |
| | 50 | | | | | 55 | | | | | 60 | | | | | |
| act | ctg | gag | aag | ctg | gtg | gaa | cac | ctg | gtg | cct | gcc | ttc | cag | ggc | agt | 240 |
| Thr | Leu | Glu | Lys | Leu | Val | Glu | His | Leu | Val | Pro | Ala | Phe | Gln | Gly | Ser | |
| 65 | | | | | 70 | | | | | 75 | | | | | 80 | |
| gac | ctt | tcc | tac | gtc | act | gtc | ttc | ctg | tgc | acc | tac | aga | gcc | ttc | act | 288 |
| Asp | Leu | Ser | Tyr | Val | Thr | Val | Phe | Leu | Cys | Thr | Tyr | Arg | Ala | Phe | Thr | |
| | | | | 85 | | | | | 90 | | | | | 95 | | |
| acc | acc | cag | cag | gtg | cta | gac | ctg | ctg | ttc | aaa | agg | tac | ggt | aga | tgt | 336 |
| Thr | Thr | Gln | Gln | Val | Leu | Asp | Leu | Leu | Phe | Lys | Arg | Tyr | Gly | Arg | Cys | |
| | | | 100 | | | | | 105 | | | | | 110 | | | |
| gac | gcc | ctc | acg | gcc | tcc | tct | aga | tat | ggc | tgc | atc | ctc | ccc | tac | tcc | 384 |
| Asp | Ala | Leu | Thr | Ala | Ser | Ser | Arg | Tyr | Gly | Cys | Ile | Leu | Pro | Tyr | Ser | |
| | | | | 115 | | | | 120 | | | | | 125 | | | |
| agt | gag | gac | ggc | gga | ccg | cag | gac | caa | ctc | aaa | aat | gcc | atc | tcc | tcc | 432 |
| Ser | Glu | Asp | Gly | Gly | Pro | Gln | Asp | Gln | Leu | Lys | Asn | Ala | Ile | Ser | Ser | |
| | 130 | | | | | 135 | | | | | 140 | | | | | |
| atc | ctg | ggc | acc | tgg | ctg | gac | caa | tac | tca | gag | gat | ttc | tgt | caa | cct | 480 |
| Ile | Leu | Gly | Thr | Trp | Leu | Asp | Gln | Tyr | Ser | Glu | Asp | Phe | Cys | Gln | Pro | |
| 145 | | | | | 150 | | | | | 155 | | | | | 160 | |
| ccg | gac | ttt | ccc | tgc | ctc | aag | cag | ctg | gtg | gct | tat | gta | cag | ctc | aac | 528 |
| Pro | Asp | Phe | Pro | Cys | Leu | Lys | Gln | Leu | Val | Ala | Tyr | Val | Gln | Leu | Asn | |
| | | | | 165 | | | | | 170 | | | | | 175 | | |
| atg | cct | ggc | tca | gat | ctg | gag | cgc | cgc | gct | cac | ctt | ctc | ctg | gcc | cag | 576 |
| Met | Pro | Gly | Ser | Asp | Leu | Glu | Arg | Arg | Ala | His | Leu | Leu | Leu | Ala | Gln | |
| | | | 180 | | | | | 185 | | | | | 190 | | | |
| ctg | gag | gac | ctg | gag | ccc | agt | gag | gct | gag | tct | gag | gcc | ctg | tcc | cca | 624 |
| Leu | Glu | Asp | Leu | Glu | Pro | Ser | Glu | Ala | Glu | Ser | Glu | Ala | Leu | Ser | Pro | |
| | | | | 195 | | | | 200 | | | | | 205 | | | |
| gct | cca | gtg | ctg | tct | ctg | aag | cca | gct | tca | cag | cta | gaa | cct | gca | ctg | 672 |
| Ala | Pro | Val | Leu | Ser | Leu | Lys | Pro | Ala | Ser | Gln | Leu | Glu | Pro | Ala | Leu | |
| | 210 | | | | | 215 | | | | | 220 | | | | | |
| ctg | ctg | acg | ccc | agc | caa | gtg | gtg | aca | tca | act | cca | gta | cga | gag | ccc | 720 |
| Leu | Leu | Thr | Pro | Ser | Gln | Val | Val | Thr | Ser | Thr | Pro | Val | Arg | Glu | Pro | |
| 225 | | | | | 230 | | | | | 235 | | | | | 240 | |
| gct | gcg | gcc | cca | gtg | cca | gtg | ctg | gcc | tcc | agc | cca | gtg | gtg | gca | cca | 768 |
| Ala | Ala | Ala | Pro | Val | Pro | Val | Leu | Ala | Ser | Ser | Pro | Val | Val | Ala | Pro | |
| | | | | 245 | | | | | 250 | | | | | 255 | | |
| gct | cct | gag | cta | gaa | cca | gtt | cca | gag | cca | cct | caa | gag | cct | gag | cca | 816 |
| Ala | Pro | Glu | Leu | Glu | Pro | Val | Pro | Glu | Pro | Pro | Gln | Glu | Pro | Glu | Pro | |
| | | | 260 | | | | | 265 | | | | | 270 | | | |
| tcc | cta | gca | ctg | gct | cca | gag | ctg | gag | ccc | gcc | gtc | tca | cag | agc | ctg | 864 |
| Ser | Leu | Ala | Leu | Ala | Pro | Glu | Leu | Glu | Pro | Ala | Val | Ser | Gln | Ser | Leu | |
| | | | | 275 | | | | 280 | | | | | 285 | | | |
| gaa | ctg | gag | tca | gct | cct | gtg | ccc | act | cct | gcc | tta | gag | cct | tcc | tgg | 912 |
| Glu | Leu | Glu | Ser | Ala | Pro | Val | Pro | Thr | Pro | Ala | Leu | Glu | Pro | Ser | Trp | |
| | 290 | | | | | 295 | | | | | 300 | | | | | |

-continued

| | | |
|---|---|---|
| tct ctg cct gaa gcc acg gag aat gga cta acc gag aag cct cac ctt<br>Ser Leu Pro Glu Ala Thr Glu Asn Gly Leu Thr Glu Lys Pro His Leu<br>305                         310                       315                     320 | | 960 |

```
tct ctg cct gaa gcc acg gag aat gga cta acc gag aag cct cac ctt        960
Ser Leu Pro Glu Ala Thr Glu Asn Gly Leu Thr Glu Lys Pro His Leu
305                 310                 315                 320 ctg ctg ttc cct cct gac ttg gtg gct gaa cag ttt act ctg atg gat       1008
Leu Leu Phe Pro Pro Asp Leu Val Ala Glu Gln Phe Thr Leu Met Asp
                325                 330                 335 gca gaa cta ttc aag aaa gtc gtg ccc tac cac tgc ctg ggc tcc atc       1056
Ala Glu Leu Phe Lys Lys Val Val Pro Tyr His Cys Leu Gly Ser Ile
            340                 345                 350 tgg tcc caa cgg gac aag aag ggc aag gag cac ctc gcg cct acc atc       1104
Trp Ser Gln Arg Asp Lys Lys Gly Lys Glu His Leu Ala Pro Thr Ile
        355                 360                 365 cgc gcc act gtc gcc cag ttc aac aac gtg gcc aac tgt gtc att act       1152
Arg Ala Thr Val Ala Gln Phe Asn Asn Val Ala Asn Cys Val Ile Thr
    370                 375                 380 acc tgc ctt ggg gac cag agt atg aag gct ccg gac agg gcc cgg gtg       1200
Thr Cys Leu Gly Asp Gln Ser Met Lys Ala Pro Asp Arg Ala Arg Val
385                 390                 395                 400 gtg gaa cac tgg atc gag gtg gcc agg gag tgc aga gcg ctc aag aat       1248
Val Glu His Trp Ile Glu Val Ala Arg Glu Cys Arg Ala Leu Lys Asn
                405                 410                 415 ttc tcc tcc ctc tac gcc atc ctc tct gct cta cag agc aat gcc atc       1296
Phe Ser Ser Leu Tyr Ala Ile Leu Ser Ala Leu Gln Ser Asn Ala Ile
            420                 425                 430 cac cgc cta aag aag acg tgg gaa gag gtc tcc agg gac agc ttt cga       1344
His Arg Leu Lys Lys Thr Trp Glu Glu Val Ser Arg Asp Ser Phe Arg
        435                 440                 445 gtg ttc cag aaa ctg tcg gag atc ttc tct gat gag aac aac tac tcc       1392
Val Phe Gln Lys Leu Ser Glu Ile Phe Ser Asp Glu Asn Asn Tyr Ser
    450                 455                 460 ctg agc aga gag ctg ctc atc aag gaa gga acc tcc aag ttt gcc aca       1440
Leu Ser Arg Glu Leu Leu Ile Lys Glu Gly Thr Ser Lys Phe Ala Thr
465                 470                 475                 480 ctg gag atg aac cct agg aga gcc cag agg cgg cag aag gag aca gga       1488
Leu Glu Met Asn Pro Arg Arg Ala Gln Arg Arg Gln Lys Glu Thr Gly
                485                 490                 495 gtc atc cag ggc acc gtt ccc tac ctg ggc aca ttc ctc act gac ctg       1536
Val Ile Gln Gly Thr Val Pro Tyr Leu Gly Thr Phe Leu Thr Asp Leu
            500                 505                 510 gtg atg ctg gac act gcc atg aag gac tat ctc tat ggg aga ctg atc       1584
Val Met Leu Asp Thr Ala Met Lys Asp Tyr Leu Tyr Gly Arg Leu Ile
        515                 520                 525 aac ttt gaa aag aga agg aag gag ttc gaa gtc att gcc cag atc aag       1632
Asn Phe Glu Lys Arg Arg Lys Glu Phe Glu Val Ile Ala Gln Ile Lys
    530                 535                 540 ttg cta cag tca gcc tgc aac aac tac agc att gct ccg gaa gaa cac       1680
Leu Leu Gln Ser Ala Cys Asn Asn Tyr Ser Ile Ala Pro Glu Glu His
545                 550                 555                 560 ttt gga aca tgg ttc cga gct atg gag cga ctc agt gag gct gag agc       1728
Phe Gly Thr Trp Phe Arg Ala Met Glu Arg Leu Ser Glu Ala Glu Ser
                565                 570                 575 tac acc ctg tcg tgt gag ctg gag ccc ccg tct gag tcg gcc agc aac       1776
Tyr Thr Leu Ser Cys Glu Leu Glu Pro Pro Ser Glu Ser Ala Ser Asn
            580                 585                 590 acc ctg agg agc aag aaa agc aca gcc att gtc aag cgc tgg agc gac       1824
Thr Leu Arg Ser Lys Lys Ser Thr Ala Ile Val Lys Arg Trp Ser Asp
        595                 600                 605 cgc cag gct ccc agc acg gag ctc agc acc agt agc agt gcc cac tcc       1872
Arg Gln Ala Pro Ser Thr Glu Leu Ser Thr Ser Ser Ser Ala His Ser
```

```
aag tcc tgt gac cag ctt cgg tgc agc cct tac ctc ggc agc ggg gac      1920
Lys Ser Cys Asp Gln Leu Arg Cys Ser Pro Tyr Leu Gly Ser Gly Asp
625                 630                 635                 640 atc acc gac gcg ctc agt gtg cac tca gct ggc tct cca agc tct gat      1968
Ile Thr Asp Ala Leu Ser Val His Ser Ala Gly Ser Ser Ser Ser Asp
                645                 650                 655 gtg gag gag atc aac atg agc ttc gtc cca gag tct cct gat ggc cag      2016
Val Glu Glu Ile Asn Met Ser Phe Val Pro Glu Ser Pro Asp Gly Gln
            660                 665                 670 gaa aag aag ttc tgg gag tca gcc tcc cag tcg tcc cca gag acc tct      2064
Glu Lys Lys Phe Trp Glu Ser Ala Ser Gln Ser Ser Pro Glu Thr Ser
        675                 680                 685 ggc atc agc tcc gcc tcc agc agc acc tcc tct tcg tca gcc tcc acc      2112
Gly Ile Ser Ser Ala Ser Ser Ser Thr Ser Ser Ser Ser Ala Ser Thr
    690                 695                 700 acg ccc gtg tct acc acg cgc acc cac aag cgc tcc gtc tca ggg gtc      2160
Thr Pro Val Ser Thr Thr Arg Thr His Lys Arg Ser Val Ser Gly Val
705                 710                 715                 720 tgc agc tac agc tcc tca ctg cct ctc tac aac cag cag gtg ggc gac      2208
Cys Ser Tyr Ser Ser Ser Leu Pro Leu Tyr Asn Gln Gln Val Gly Asp
                725                 730                 735 tgc tgc atc atc agg gtc agc ctg gat gtg gac aac ggc aac atg tac      2256
Cys Cys Ile Ile Arg Val Ser Leu Asp Val Asp Asn Gly Asn Met Tyr
            740                 745                 750 aag agc atc ctg gtg acc agc cag gat aag gct ccg act gtc atc cga      2304
Lys Ser Ile Leu Val Thr Ser Gln Asp Lys Ala Pro Thr Val Ile Arg
        755                 760                 765 aaa gcc atg gac aaa cac aac cta gat gag gac gag ccg gag gat tat      2352
Lys Ala Met Asp Lys His Asn Leu Asp Glu Asp Glu Pro Glu Asp Tyr
    770                 775                 780 gag ctg gtg cag atc atc tca gag gat cac aag ctg aag att cca gaa      2400
Glu Leu Val Gln Ile Ile Ser Glu Asp His Lys Leu Lys Ile Pro Glu
785                 790                 795                 800 aac gcc aat gtg ttc tat gcc atg aac tct acc gcc aac tat gac ttc      2448
Asn Ala Asn Val Phe Tyr Ala Met Asn Ser Thr Ala Asn Tyr Asp Phe
                805                 810                 815 atc cta aag aag cgg acc ttc act aag ggg gct aaa gtc aag cat gga      2496
Ile Leu Lys Lys Arg Thr Phe Thr Lys Gly Ala Lys Val Lys His Gly
            820                 825                 830 gcc agc tcc acc ctc cct cgt atg aag cag aag gga ctc agg att gcc      2544
Ala Ser Ser Thr Leu Pro Arg Met Lys Gln Lys Gly Leu Arg Ile Ala
        835                 840                 845 aaa ggc atc ttc taa                                                  2559
Lys Gly Ile Phe
    850

<210> SEQ ID NO 23
<211> LENGTH: 852
<212> TYPE: PRT
<213> ORGANISM: Mus musculus

<400> SEQUENCE: 23

Met Met Val Asp Cys Gln Ser Ser Thr Gln Glu Ile Gly Glu Leu
1               5                   10                  15

Ile Asn Gly Val Ile Tyr Ser Ile Ser Leu Arg Lys Val Gln Leu His
                20                  25                  30

Gln Gly Ala Thr Lys Gly Gln Arg Trp Leu Gly Cys Glu Asn Glu Ser
            35                  40                  45
```

-continued

```
Ala Leu Asn Leu Tyr Glu Thr Cys Lys Val Arg Thr Val Lys Ala Gly
     50                  55                  60

Thr Leu Glu Lys Leu Val Glu His Leu Val Pro Ala Phe Gln Gly Ser
 65                  70                  75                  80

Asp Leu Ser Tyr Val Thr Val Phe Leu Cys Thr Tyr Arg Ala Phe Thr
                 85                  90                  95

Thr Thr Gln Gln Val Leu Asp Leu Leu Phe Lys Arg Tyr Gly Arg Cys
            100                 105                 110

Asp Ala Leu Thr Ala Ser Ser Arg Tyr Gly Cys Ile Leu Pro Tyr Ser
        115                 120                 125

Ser Glu Asp Gly Gly Pro Gln Asp Gln Leu Lys Asn Ala Ile Ser Ser
130                 135                 140

Ile Leu Gly Thr Trp Leu Asp Gln Tyr Ser Glu Asp Phe Cys Gln Pro
145                 150                 155                 160

Pro Asp Phe Pro Cys Leu Lys Gln Leu Val Ala Tyr Val Gln Leu Asn
                165                 170                 175

Met Pro Gly Ser Asp Leu Glu Arg Arg Ala His Leu Leu Leu Ala Gln
            180                 185                 190

Leu Glu Asp Leu Glu Pro Ser Glu Ala Glu Ser Glu Ala Leu Ser Pro
        195                 200                 205

Ala Pro Val Leu Ser Leu Lys Pro Ala Ser Gln Leu Glu Pro Ala Leu
    210                 215                 220

Leu Leu Thr Pro Ser Gln Val Val Thr Ser Thr Pro Val Arg Glu Pro
225                 230                 235                 240

Ala Ala Ala Pro Val Pro Val Leu Ala Ser Ser Pro Val Val Ala Pro
                245                 250                 255

Ala Pro Glu Leu Glu Pro Val Pro Glu Pro Gln Glu Pro Glu Pro
            260                 265                 270

Ser Leu Ala Leu Ala Pro Glu Leu Glu Pro Ala Val Ser Gln Ser Leu
        275                 280                 285

Glu Leu Glu Ser Ala Pro Val Pro Thr Pro Ala Leu Gly Pro Ser Trp
290                 295                 300

Ser Leu Pro Glu Ala Thr Glu Asn Gly Leu Thr Glu Lys Pro His Leu
305                 310                 315                 320

Leu Leu Phe Pro Pro Asp Leu Val Ala Glu Gln Phe Thr Leu Met Asp
                325                 330                 335

Ala Glu Leu Phe Lys Lys Val Val Pro Tyr His Cys Leu Gly Ser Ile
            340                 345                 350

Trp Ser Gln Arg Asp Lys Lys Gly Lys Glu His Leu Ala Pro Thr Ile
        355                 360                 365

Arg Ala Thr Val Ala Gln Phe Asn Asn Val Ala Asn Cys Val Ile Thr
    370                 375                 380

Thr Cys Leu Gly Asp Gln Ser Met Lys Ala Pro Asp Arg Ala Arg Val
385                 390                 395                 400

Val Glu His Trp Ile Glu Val Ala Arg Glu Cys Arg Ala Leu Lys Asn
                405                 410                 415

Phe Ser Ser Leu Tyr Ala Ile Leu Ser Ala Leu Gln Ser Asn Ala Ile
            420                 425                 430

His Arg Leu Lys Lys Thr Trp Glu Val Ser Arg Asp Ser Phe Arg
        435                 440                 445

Val Phe Gln Lys Leu Ser Glu Ile Phe Ser Asp Glu Asn Asn Tyr Ser
    450                 455                 460

Leu Ser Arg Glu Leu Leu Ile Lys Glu Gly Thr Ser Lys Phe Ala Thr
```

-continued

```
               465                 470                 475                 480
Leu Glu Met Asn Pro Arg Arg Ala Gln Arg Arg Gln Lys Glu Thr Gly
                    485                 490                 495

Val Ile Gln Gly Thr Val Pro Tyr Leu Gly Thr Phe Leu Thr Asp Leu
                500                 505                 510

Val Met Leu Asp Thr Ala Met Lys Asp Tyr Leu Tyr Gly Arg Leu Ile
            515                 520                 525

Asn Phe Glu Lys Arg Arg Lys Glu Phe Glu Val Ile Ala Gln Ile Lys
        530                 535                 540

Leu Leu Gln Ser Ala Cys Asn Asn Tyr Ser Ile Ala Pro Glu Glu His
545                 550                 555                 560

Phe Gly Thr Trp Phe Arg Ala Met Glu Arg Leu Ser Glu Ala Glu Ser
                565                 570                 575

Tyr Thr Leu Ser Cys Glu Leu Glu Pro Pro Ser Glu Ser Ala Ser Asn
                580                 585                 590

Thr Leu Arg Ser Lys Lys Ser Thr Ala Ile Val Lys Arg Trp Ser Asp
            595                 600                 605

Arg Gln Ala Pro Ser Thr Glu Leu Ser Thr Ser Ser Ala His Ser
        610                 615                 620

Lys Ser Cys Asp Gln Leu Arg Cys Ser Pro Tyr Leu Gly Ser Gly Asp
625                 630                 635                 640

Ile Thr Asp Ala Leu Ser Val His Ser Ala Gly Ser Ser Ser Ser Asp
                645                 650                 655

Val Glu Glu Ile Asn Met Ser Phe Val Pro Glu Ser Pro Asp Gly Gln
                660                 665                 670

Glu Lys Lys Phe Trp Glu Ser Ala Ser Gln Ser Ser Pro Glu Thr Ser
            675                 680                 685

Gly Ile Ser Ser Ala Ser Ser Ser Thr Ser Ser Ser Ala Ser Thr
        690                 695                 700

Thr Pro Val Ser Thr Arg Thr His Lys Arg Ser Val Ser Gly Val
705                 710                 715                 720

Cys Ser Tyr Ser Ser Leu Pro Leu Tyr Asn Gln Gln Val Gly Asp
                725                 730                 735

Cys Cys Ile Ile Arg Val Ser Leu Asp Val Asp Asn Gly Asn Met Tyr
                740                 745                 750

Lys Ser Ile Leu Val Thr Ser Gln Asp Lys Ala Pro Thr Val Ile Arg
            755                 760                 765

Lys Ala Met Asp Lys His Asn Leu Asp Glu Asp Glu Pro Glu Asp Tyr
        770                 775                 780

Glu Leu Val Gln Ile Ile Ser Glu Asp His Lys Leu Lys Ile Pro Glu
785                 790                 795                 800

Asn Ala Asn Val Phe Tyr Ala Met Asn Ser Thr Ala Asn Tyr Asp Phe
                805                 810                 815

Ile Leu Lys Lys Arg Thr Phe Thr Lys Gly Ala Lys Val Lys His Gly
                820                 825                 830

Ala Ser Ser Thr Leu Pro Arg Met Lys Gln Lys Gly Leu Arg Ile Ala
            835                 840                 845

Lys Gly Ile Phe
        850

<210> SEQ ID NO 24
<211> LENGTH: 2745
<212> TYPE: DNA
<213> ORGANISM: Homo sapiens
```

```
<220> FEATURE:
<221> NAME/KEY: CDS
<222> LOCATION: (1)..(2745)

<400> SEQUENCE: 24 atg gtg cag cgc atg tgg gcc gag gcg gcc ggg cct gct ggc ggc gcc      48
Met Val Gln Arg Met Trp Ala Glu Ala Ala Gly Pro Ala Gly Gly Ala
1               5                   10                  15 gag ccg ctg ttt ccg ggc tcc cgg cgg agc cgc agc gtg tgg gac gcc      96
Glu Pro Leu Phe Pro Gly Ser Arg Arg Ser Arg Ser Val Trp Asp Ala
            20                  25                  30 gtg cgc ctg gag gtg ggc gtc ccc gac agc tgc ccg gtg gtg ctg cac     144
Val Arg Leu Glu Val Gly Val Pro Asp Ser Cys Pro Val Val Leu His
        35                  40                  45 agc ttc acg cag cta gac ccc gac ctg ccg cgc ccg gag agc tcc acg     192
Ser Phe Thr Gln Leu Asp Pro Asp Leu Pro Arg Pro Glu Ser Ser Thr
    50                  55                  60 cag gag atc ggt gag gag ctg atc aac gga gtc atc tac tcc atc tcc     240
Gln Glu Ile Gly Glu Glu Leu Ile Asn Gly Val Ile Tyr Ser Ile Ser
65                  70                  75                  80 ctg cgc aag gtg cag ctg cac cac gga ggc aac aag ggg cag cgc tgg     288
Leu Arg Lys Val Gln Leu His His Gly Gly Asn Lys Gly Gln Arg Trp
                85                  90                  95 ctc ggg tat gag aat gag tcg gcc ctg aac ctt tat gag act tgc aag     336
Leu Gly Tyr Glu Asn Glu Ser Ala Leu Asn Leu Tyr Glu Thr Cys Lys
            100                 105                 110 gtg cgg acc gtg aag gct ggc acg ctg gag aag ctg gtg gag cac ctg     384
Val Arg Thr Val Lys Ala Gly Thr Leu Glu Lys Leu Val Glu His Leu
        115                 120                 125 gtg cca gcc ttc cag ggc agc gac ctc tcc tac gtc acc atc ttc ctg     432
Val Pro Ala Phe Gln Gly Ser Asp Leu Ser Tyr Val Thr Ile Phe Leu
    130                 135                 140 tgt acc tat aga gcc ttc acc acc acc caa cag gtc ctg gac ctg ctg     480
Cys Thr Tyr Arg Ala Phe Thr Thr Thr Gln Gln Val Leu Asp Leu Leu
145                 150                 155                 160 ttc aaa agg tac ggt aga tgt gac gcc ctc acg gcc tcc tct aga tac     528
Phe Lys Arg Tyr Gly Arg Cys Asp Ala Leu Thr Ala Ser Ser Arg Tyr
                165                 170                 175 ggc tgc atc ctc ccc tat tcc gac gag gat ggt gga ccc cag gac caa     576
Gly Cys Ile Leu Pro Tyr Ser Asp Glu Asp Gly Gly Pro Gln Asp Gln
            180                 185                 190 ctt aaa aat gcc atc tcc tcc atc ctg ggc acc tgg ctg gac cag tac     624
Leu Lys Asn Ala Ile Ser Ser Ile Leu Gly Thr Trp Leu Asp Gln Tyr
        195                 200                 205 tcg gag gat ttc tgt caa cct ccg gac ttt ccc tgc ctc aag cag ctg     672
Ser Glu Asp Phe Cys Gln Pro Pro Asp Phe Pro Cys Leu Lys Gln Leu
    210                 215                 220 gtg gcc tac gtg cag ctc aac atg cca ggc tca gac ctg gag cgc cgt     720
Val Ala Tyr Val Gln Leu Asn Met Pro Gly Ser Asp Leu Glu Arg Arg
225                 230                 235                 240 gcc cac ctt ctc ctg gcc cag ctg gag cac tcg gaa ccc att gag gca     768
Ala His Leu Leu Leu Ala Gln Leu Glu His Ser Glu Pro Ile Glu Ala
                245                 250                 255 gag cct gag gct ctg tca cca gtg cca gct cta aaa cca act cca gag     816
Glu Pro Glu Ala Leu Ser Pro Val Pro Ala Leu Lys Pro Thr Pro Glu
            260                 265                 270 ctc gag cta gct cta aca cca gct cga gca ccc agc cca gtg ccg gct     864
Leu Glu Leu Ala Leu Thr Pro Ala Arg Ala Pro Ser Pro Val Pro Ala
        275                 280                 285 cca gcc ccg gag cca gag cca gct cca aca cca gct cca ggt tca gag     912
```

```
Pro Ala Pro Glu Pro Glu Pro Ala Pro Thr Pro Ala Pro Gly Ser Glu
    290                 295                 300 cta gaa gta gct cca gca cca gct ccg gag ctc cag cag gct cca gag      960
Leu Glu Val Ala Pro Ala Pro Ala Pro Glu Leu Gln Gln Ala Pro Glu
305                 310                 315                 320 cca gct gtg gga cta gaa tcg gct cca gcg cca gct ctg gaa cta gag     1008
Pro Ala Val Gly Leu Glu Ser Ala Pro Ala Pro Ala Leu Glu Leu Glu
            325                 330                 335 cca gct cca gaa cag gat cca gct ccc tca caa act cta gag ctg gag     1056
Pro Ala Pro Glu Gln Asp Pro Ala Pro Ser Gln Thr Leu Glu Leu Glu
                340                 345                 350 cca gct cca gca cca gtt cca tca tta cag cct tcc tgg cct tca cct     1104
Pro Ala Pro Ala Pro Val Pro Ser Leu Gln Pro Ser Trp Pro Ser Pro
                    355                 360                 365 gtg gtt gca gag aac ggg ctg agt gag gag aag cct cac ctc ttg gtg     1152
Val Val Ala Glu Asn Gly Leu Ser Glu Glu Lys Pro His Leu Leu Val
370                 375                 380 ttc cct cca gat ctg gtg gca gag cag ttt aca ctg atg gat gcg gaa     1200
Phe Pro Pro Asp Leu Val Ala Glu Gln Phe Thr Leu Met Asp Ala Glu
385                 390                 395                 400 ctg ttc aag aag gtg gtg ccc tac cac tgc ctg ggc tcc atc tgg tcc     1248
Leu Phe Lys Lys Val Val Pro Tyr His Cys Leu Gly Ser Ile Trp Ser
            405                 410                 415 cag cgg gac aag aag ggc aag gag cac ctg gcg ccc acc atc cgc gcc     1296
Gln Arg Asp Lys Lys Gly Lys Glu His Leu Ala Pro Thr Ile Arg Ala
                420                 425                 430 act gtc acc cag ttc aac agt gtg gcc aac tgt gtc atc acc acc tgc     1344
Thr Val Thr Gln Phe Asn Ser Val Ala Asn Cys Val Ile Thr Thr Cys
                    435                 440                 445 ctc ggg aac cga agc acg aaa gcc cca gac agg gcc agg gtg gtg gag     1392
Leu Gly Asn Arg Ser Thr Lys Ala Pro Asp Arg Ala Arg Val Val Glu
450                 455                 460 cac tgg atc gag gtg gcc agg gag tgc cgg atc ctc aag aac ttc tcg     1440
His Trp Ile Glu Val Ala Arg Glu Cys Arg Ile Leu Lys Asn Phe Ser
465                 470                 475                 480 tca ctg tat gcc atc ctc tct gcc ctg cag agc aac tcc atc cac cgt     1488
Ser Leu Tyr Ala Ile Leu Ser Ala Leu Gln Ser Asn Ser Ile His Arg
            485                 490                 495 ctg aag aag acg tgg gaa gac gtt tcc agg gac agt ttc cgg atc ttt     1536
Leu Lys Lys Thr Trp Glu Asp Val Ser Arg Asp Ser Phe Arg Ile Phe
                500                 505                 510 cag aag ctg tca gag atc ttc tca gat gag aac aac tac tca ttg agc     1584
Gln Lys Leu Ser Glu Ile Phe Ser Asp Glu Asn Asn Tyr Ser Leu Ser
                    515                 520                 525 cgg gag ctg ctc atc aag gag ggc acc tcc aag ttt gcc acc ctg gag     1632
Arg Glu Leu Leu Ile Lys Glu Gly Thr Ser Lys Phe Ala Thr Leu Glu
530                 535                 540 atg aac ccc aag aga gcc cag aaa cgg ccg aag gag acg ggc atc atc     1680
Met Asn Pro Lys Arg Ala Gln Lys Arg Pro Lys Glu Thr Gly Ile Ile
545                 550                 555                 560 cag ggc acc gtt ccc tac ctg ggc acg ttc ctc acc gac ctg gtg atg     1728
Gln Gly Thr Val Pro Tyr Leu Gly Thr Phe Leu Thr Asp Leu Val Met
            565                 570                 575 ctg gac act gcc atg aag gac tat ctg tat ggc aga ctc atc aac ttt     1776
Leu Asp Thr Ala Met Lys Asp Tyr Leu Tyr Gly Arg Leu Ile Asn Phe
                580                 585                 590 gag aag agg agg aag gag ttc gag gtg atc gcc cag atc aag ctg ctg     1824
Glu Lys Arg Arg Lys Glu Phe Glu Val Ile Ala Gln Ile Lys Leu Leu
                    595                 600                 605
```

-continued

| | | |
|---|---|---|
| cag tcg gcc tgc aac aac tac agc atc gcg cca gat gag caa ttt ggg<br>Gln Ser Ala Cys Asn Asn Tyr Ser Ile Ala Pro Asp Glu Gln Phe Gly<br>610                          615                      620 | | 1872 |
| gcc tgg ttc cgg gcc gtg gag cgg ctc agc gag act gag agc tac aac<br>Ala Trp Phe Arg Ala Val Glu Arg Leu Ser Glu Thr Glu Ser Tyr Asn<br>625                          630                      635                      640 | | 1920 |
| ctg tcg tgc gag ctg gag ccc cca tcc gag tca gcc agc aac acc ctc<br>Leu Ser Cys Glu Leu Glu Pro Pro Ser Glu Ser Ala Ser Asn Thr Leu<br>                       645                      650                      655 | | 1968 |
| agg acc aag aag aac aca gcc att gtc aag cgc tgg agc gac cgc cag<br>Arg Thr Lys Lys Asn Thr Ala Ile Val Lys Arg Trp Ser Asp Arg Gln<br>           660                      665                      670 | | 2016 |
| gcc ccc agc act gag ctc agt acc agt ggc agc tcc cac tcc aag tcc<br>Ala Pro Ser Thr Glu Leu Ser Thr Ser Gly Ser Ser His Ser Lys Ser<br>675                          680                      685 | | 2064 |
| tgt gac cag ctc agg tgt ggc ccc tac ctc agc agc ggg gac atc gct<br>Cys Asp Gln Leu Arg Cys Gly Pro Tyr Leu Ser Ser Gly Asp Ile Ala<br>     690                      695                      700 | | 2112 |
| gac gcg ctc agc gtg cac tcg gcc ggc tcc tct agc tcc gac gtg gag<br>Asp Ala Leu Ser Val His Ser Ala Gly Ser Ser Ser Ser Asp Val Glu<br>705                          710                      715                      720 | | 2160 |
| gag atc aac atc agc ttc gtc ccg gag tct cct gat ggc cag gaa aag<br>Glu Ile Asn Ile Ser Phe Val Pro Glu Ser Pro Asp Gly Gln Glu Lys<br>                       725                      730                      735 | | 2208 |
| aag ttc tgg gaa tca gcc tca cag tca tcc ccg gag acc tcc ggc atc<br>Lys Phe Trp Glu Ser Ala Ser Gln Ser Ser Pro Glu Thr Ser Gly Ile<br>           740                      745                      750 | | 2256 |
| agc tca gcc tcc agc agc acc tcg tcc tca gcc tcc acc acg ccc<br>Ser Ser Ala Ser Ser Ser Thr Ser Ser Ser Ala Ser Thr Thr Pro<br>755                          760                      765 | | 2304 |
| gtg gct gcc aca cgc acc cac aag cgc tct gtc tca ggg ctc tgc aac<br>Val Ala Ala Thr Arg Thr His Lys Arg Ser Val Ser Gly Leu Cys Asn<br>           770                      775                      780 | | 2352 |
| tcc agc tcc gcg ctg ccg ctc tac aac cag cag gtg ggc gac tgc tgt<br>Ser Ser Ser Ala Leu Pro Leu Tyr Asn Gln Gln Val Gly Asp Cys Cys<br>785                          790                      795                      800 | | 2400 |
| atc atc cgc gtc agc ctg gac gtg gac aat ggc aac atg tac aag agc<br>Ile Ile Arg Val Ser Leu Asp Val Asp Asn Gly Asn Met Tyr Lys Ser<br>                       805                      810                      815 | | 2448 |
| atc ctg gtg acc agc caa gat aag gct ccg gct gta atc cgc aag gcc<br>Ile Leu Val Thr Ser Gln Asp Lys Ala Pro Ala Val Ile Arg Lys Ala<br>           820                      825                      830 | | 2496 |
| atg gac aaa cac aac ctg gag gag gag gag ccg gag gac tat gag ctg<br>Met Asp Lys His Asn Leu Glu Glu Glu Glu Pro Glu Asp Tyr Glu Leu<br>                       835                      840                      845 | | 2544 |
| ctg cag att ctc tca gat gac cgg aag ctg aag atc cct gaa aac gcc<br>Leu Gln Ile Leu Ser Asp Asp Arg Lys Leu Lys Ile Pro Glu Asn Ala<br>850                          855                      860 | | 2592 |
| aac gtc ttc tat gcc atg aac tct acc gcc aac tat gac ttt gtc ctc<br>Asn Val Phe Tyr Ala Met Asn Ser Thr Ala Asn Tyr Asp Phe Val Leu<br>865                          870                      875                      880 | | 2640 |
| aag aag cgg acc ttc acc aag gga gtg aag gtc aag cac gga gcc agc<br>Lys Lys Arg Thr Phe Thr Lys Gly Val Lys Val Lys His Gly Ala Ser<br>                       885                      890                      895 | | 2688 |
| tcc acc ctc cct cgc atg aag cag aaa gga ctc aag att gcc aag ggc<br>Ser Thr Leu Pro Arg Met Lys Gln Lys Gly Leu Lys Ile Ala Lys Gly<br>           900                      905                      910 | | 2736 |
| atc ttc tga<br>Ile Phe | | 2745 |

<210> SEQ ID NO 25
<211> LENGTH: 914
<212> TYPE: PRT
<213> ORGANISM: Homo sapiens

<400> SEQUENCE: 25

```
Met Val Gln Arg Met Trp Ala Glu Ala Ala Gly Pro Ala Gly Gly Ala
1               5                   10                  15

Glu Pro Leu Phe Pro Gly Ser Arg Arg Ser Arg Ser Val Trp Asp Ala
            20                  25                  30

Val Arg Leu Glu Val Gly Val Pro Asp Ser Cys Pro Val Val Leu His
        35                  40                  45

Ser Phe Thr Gln Leu Asp Pro Asp Leu Pro Arg Pro Glu Ser Ser Thr
    50                  55                  60

Gln Glu Ile Gly Glu Glu Leu Ile Asn Gly Val Ile Tyr Ser Ile Ser
65                  70                  75                  80

Leu Arg Lys Val Gln Leu His His Gly Gly Asn Lys Gly Gln Arg Trp
                85                  90                  95

Leu Gly Tyr Glu Asn Glu Ser Ala Leu Asn Leu Tyr Glu Thr Cys Lys
            100                 105                 110

Val Arg Thr Val Lys Ala Gly Thr Leu Glu Lys Leu Val Glu His Leu
        115                 120                 125

Val Pro Ala Phe Gln Gly Ser Asp Leu Ser Tyr Val Thr Ile Phe Leu
    130                 135                 140

Cys Thr Tyr Arg Ala Phe Thr Thr Thr Gln Gln Val Leu Asp Leu Leu
145                 150                 155                 160

Phe Lys Arg Tyr Gly Arg Cys Asp Ala Leu Thr Ala Ser Ser Arg Tyr
                165                 170                 175

Gly Cys Ile Leu Pro Tyr Ser Asp Glu Asp Gly Gly Pro Gln Asp Gln
            180                 185                 190

Leu Lys Asn Ala Ile Ser Ser Ile Leu Gly Thr Trp Leu Asp Gln Tyr
        195                 200                 205

Ser Glu Asp Phe Cys Gln Pro Pro Asp Phe Pro Cys Leu Lys Gln Leu
    210                 215                 220

Val Ala Tyr Val Gln Leu Asn Met Pro Gly Ser Asp Leu Glu Arg Arg
225                 230                 235                 240

Ala His Leu Leu Leu Ala Gln Leu Glu His Ser Glu Pro Ile Glu Ala
                245                 250                 255

Glu Pro Glu Ala Leu Ser Pro Val Pro Ala Leu Lys Pro Thr Pro Glu
            260                 265                 270

Leu Glu Leu Ala Leu Thr Pro Ala Arg Ala Pro Ser Pro Val Pro Ala
        275                 280                 285

Pro Ala Pro Glu Pro Glu Pro Ala Pro Thr Pro Ala Pro Gly Ser Glu
    290                 295                 300

Leu Glu Val Ala Pro Ala Pro Ala Pro Glu Leu Gln Gln Ala Pro Glu
305                 310                 315                 320

Pro Ala Val Gly Leu Glu Ser Ala Pro Ala Leu Glu Leu Glu
                325                 330                 335

Pro Ala Pro Glu Gln Asp Pro Ala Pro Ser Gln Thr Leu Glu Leu Glu
            340                 345                 350

Pro Ala Pro Ala Pro Val Pro Ser Leu Gln Pro Ser Trp Pro Ser Pro
        355                 360                 365

Val Val Ala Glu Asn Gly Leu Ser Glu Glu Lys Pro His Leu Leu Val
    370                 375                 380
```

-continued

```
Phe Pro Pro Asp Leu Val Ala Glu Gln Phe Thr Leu Met Asp Ala Glu
385                 390                 395                 400

Leu Phe Lys Lys Val Val Pro Tyr His Cys Leu Gly Ser Ile Trp Ser
                405                 410                 415

Gln Arg Asp Lys Lys Gly Lys Glu His Leu Ala Pro Thr Ile Arg Ala
            420                 425                 430

Thr Val Thr Gln Phe Asn Ser Val Ala Asn Cys Val Ile Thr Thr Cys
            435                 440                 445

Leu Gly Asn Arg Ser Thr Lys Ala Pro Asp Arg Ala Arg Val Val Glu
        450                 455                 460

His Trp Ile Glu Val Ala Arg Glu Cys Arg Ile Leu Lys Asn Phe Ser
465                 470                 475                 480

Ser Leu Tyr Ala Ile Leu Ser Ala Leu Gln Ser Asn Ser Ile His Arg
                485                 490                 495

Leu Lys Lys Thr Trp Glu Asp Val Ser Arg Asp Ser Phe Arg Ile Phe
            500                 505                 510

Gln Lys Leu Ser Glu Ile Phe Ser Asp Glu Asn Asn Tyr Ser Leu Ser
        515                 520                 525

Arg Glu Leu Leu Ile Lys Glu Gly Thr Ser Lys Phe Ala Thr Leu Glu
530                 535                 540

Met Asn Pro Lys Arg Ala Gln Lys Arg Pro Lys Glu Thr Gly Ile Ile
545                 550                 555                 560

Gln Gly Thr Val Pro Tyr Leu Gly Thr Phe Leu Thr Asp Leu Val Met
            565                 570                 575

Leu Asp Thr Ala Met Lys Asp Tyr Leu Tyr Gly Arg Leu Ile Asn Phe
        580                 585                 590

Glu Lys Arg Arg Lys Glu Phe Glu Val Ile Ala Gln Ile Lys Leu Leu
    595                 600                 605

Gln Ser Ala Cys Asn Asn Tyr Ser Ile Ala Pro Asp Glu Gln Phe Gly
610                 615                 620

Ala Trp Phe Arg Ala Val Glu Arg Leu Ser Glu Thr Glu Ser Tyr Asn
625                 630                 635                 640

Leu Ser Cys Glu Leu Glu Pro Pro Ser Glu Ser Ala Ser Asn Thr Leu
            645                 650                 655

Arg Thr Lys Lys Asn Thr Ala Ile Val Lys Arg Trp Ser Asp Arg Gln
        660                 665                 670

Ala Pro Ser Thr Glu Leu Ser Thr Ser Gly Ser Ser His Ser Lys Ser
    675                 680                 685

Cys Asp Gln Leu Arg Cys Gly Pro Tyr Leu Ser Ser Gly Asp Ile Ala
690                 695                 700

Asp Ala Leu Ser Val His Ser Ala Gly Ser Ser Ser Asp Val Glu
705                 710                 715                 720

Glu Ile Asn Ile Ser Phe Val Pro Glu Ser Pro Asp Gly Gln Glu Lys
            725                 730                 735

Lys Phe Trp Glu Ser Ala Ser Gln Ser Ser Pro Glu Thr Ser Gly Ile
        740                 745                 750

Ser Ser Ala Ser Ser Ser Thr Ser Ser Ser Ala Ser Thr Thr Pro
    755                 760                 765

Val Ala Ala Thr Arg Thr His Lys Arg Ser Val Ser Gly Leu Cys Asn
770                 775                 780

Ser Ser Ser Ala Leu Pro Leu Tyr Asn Gln Gln Val Gly Asp Cys Cys
785                 790                 795                 800
```

```
Ile Ile Arg Val Ser Leu Asp Val Asp Asn Gly Asn Met Tyr Lys Ser
                805                 810                 815

Ile Leu Val Thr Ser Gln Asp Lys Ala Pro Ala Val Ile Arg Lys Ala
            820                 825                 830

Met Asp Lys His Asn Leu Glu Glu Glu Pro Glu Asp Tyr Glu Leu
        835                 840                 845

Leu Gln Ile Leu Ser Asp Arg Lys Leu Lys Ile Pro Glu Asn Ala
    850                 855                 860

Asn Val Phe Tyr Ala Met Asn Ser Thr Ala Asn Tyr Asp Phe Val Leu
865                 870                 875                 880

Lys Lys Arg Thr Phe Thr Lys Gly Val Lys Val Lys His Gly Ala Ser
                885                 890                 895

Ser Thr Leu Pro Arg Met Lys Gln Lys Gly Leu Lys Ile Ala Lys Gly
                900                 905                 910

Ile Phe

<210> SEQ ID NO 26
<211> LENGTH: 1947
<212> TYPE: DNA
<213> ORGANISM: Mus musculus
<220> FEATURE:
<221> NAME/KEY: CDS
<222> LOCATION: (1)..(1947)

<400> SEQUENCE: 26 atg gag cac ata cag gga gct tgg aag acg atc agc aat ggc ttt gga        48
Met Glu His Ile Gln Gly Ala Trp Lys Thr Ile Ser Asn Gly Phe Gly
1               5                   10                  15 ctc aaa gat gcg gtg ttt gat ggc tcc agc tgc atc tcc cct acc att       96
Leu Lys Asp Ala Val Phe Asp Gly Ser Ser Cys Ile Ser Pro Thr Ile
            20                  25                  30 gtt cag cag ttt ggc tat cag cgc cgg gcc tca gat gat ggc aag ctc      144
Val Gln Gln Phe Gly Tyr Gln Arg Arg Ala Ser Asp Asp Gly Lys Leu
        35                  40                  45 acg gat tct tct aag aca agc aat act atc cgg gtt ttc ttg ccg aat      192
Thr Asp Ser Ser Lys Thr Ser Asn Thr Ile Arg Val Phe Leu Pro Asn
    50                  55                  60 aag caa agg act gtg gtc aat gtg cgg aat gga atg agc tta cat gac      240
Lys Gln Arg Thr Val Val Asn Val Arg Asn Gly Met Ser Leu His Asp
65                  70                  75                  80 tgc ctt atg aaa gct ctg aag gtg aga ggc ctg cag cca gag tgc tgt      288
Cys Leu Met Lys Ala Leu Lys Val Arg Gly Leu Gln Pro Glu Cys Cys
                85                  90                  95 gca gtg ttc aga ctt ctc cag gaa cac aaa ggt aag aaa gca cgc tta      336
Ala Val Phe Arg Leu Leu Gln Glu His Lys Gly Lys Lys Ala Arg Leu
            100                 105                 110 gat tgg aac acc gat gcc gcc tct ctg att gga gaa gaa ctg caa gtg      384
Asp Trp Asn Thr Asp Ala Ala Ser Leu Ile Gly Glu Glu Leu Gln Val
        115                 120                 125 gat ttt ttg gat cat gtt cca ctc aca act cac aac ttt gct cgg aaa      432
Asp Phe Leu Asp His Val Pro Leu Thr Thr His Asn Phe Ala Arg Lys
    130                 135                 140 acg ttc ctg aag ctt gca ttc tgt gac atc tgt cag aag ttc ctg cta      480
Thr Phe Leu Lys Leu Ala Phe Cys Asp Ile Cys Gln Lys Phe Leu Leu
145                 150                 155                 160 aat gga ttt cga tgt cag act tgt ggc tac aag ttt cat gag cac tgt      528
Asn Gly Phe Arg Cys Gln Thr Cys Gly Tyr Lys Phe His Glu His Cys
                165                 170                 175 agc acc aaa gta cct act atg tgt gtg gac tgg agt aat atc aga cag      576
```

-continued

```
Ser Thr Lys Val Pro Thr Met Cys Val Asp Trp Ser Asn Ile Arg Gln
            180                 185                 190 ctc ttg ctg ttt cca aat tcc act gtt ggt gac agt gga gtc cca gca      624
Leu Leu Leu Phe Pro Asn Ser Thr Val Gly Asp Ser Gly Val Pro Ala
        195                 200                 205 cca cct tct ttc cca atg cgt cgg atg cga gaa tct gtt tcc cgg atg      672
Pro Pro Ser Phe Pro Met Arg Arg Met Arg Glu Ser Val Ser Arg Met
210                 215                 220 cct gct agt tcc cag cac aga tac tct aca ccc cat gcc ttc act ttc      720
Pro Ala Ser Ser Gln His Arg Tyr Ser Thr Pro His Ala Phe Thr Phe
225                 230                 235                 240 aac acc tcc agc cct tcc tca gaa ggt tcc ctg tcc cag agg cag agg      768
Asn Thr Ser Ser Pro Ser Ser Glu Gly Ser Leu Ser Gln Arg Gln Arg
            245                 250                 255 tca acg tcc act ccc aat gtc cac atg gtc agc acc acc ctg cat gtg      816
Ser Thr Ser Thr Pro Asn Val His Met Val Ser Thr Thr Leu His Val
        260                 265                 270 gac agc agg atg att gag gat gca att cga agt cac agt gaa tca gcc      864
Asp Ser Arg Met Ile Glu Asp Ala Ile Arg Ser His Ser Glu Ser Ala
    275                 280                 285 tca cct tca gcc ctg tcc agc agc cca aac aac ctg agt cca aca ggc      912
Ser Pro Ser Ala Leu Ser Ser Ser Pro Asn Asn Leu Ser Pro Thr Gly
290                 295                 300 tgg tca cag ccc aaa acc cct gtg cca gca caa aga gag cgg gca cca      960
Trp Ser Gln Pro Lys Thr Pro Val Pro Ala Gln Arg Glu Arg Ala Pro
305                 310                 315                 320 gga tct ggg acc cag gaa aaa aac aaa att agg cct cgt ggg cag aga     1008
Gly Ser Gly Thr Gln Glu Lys Asn Lys Ile Arg Pro Arg Gly Gln Arg
            325                 330                 335 gac tcg agt tat tac tgg gaa ata gaa gcc agt gag gtg atg ctg tct     1056
Asp Ser Ser Tyr Tyr Trp Glu Ile Glu Ala Ser Glu Val Met Leu Ser
        340                 345                 350 act cgg atc ggg tca ggt tcc ttt ggc act gtg tac aag ggc aag tgg     1104
Thr Arg Ile Gly Ser Gly Ser Phe Gly Thr Val Tyr Lys Gly Lys Trp
    355                 360                 365 cat gga gat gtt gca gta aag atc cta aag gtg gtt gac cca act cca     1152
His Gly Asp Val Ala Val Lys Ile Leu Lys Val Val Asp Pro Thr Pro
370                 375                 380 gag caa ctt cag gcc ttc agg aac gag gtg gct gtt ttg cgc aaa aca     1200
Glu Gln Leu Gln Ala Phe Arg Asn Glu Val Ala Val Leu Arg Lys Thr
385                 390                 395                 400 cgg cat gtt aac atc ctg ctg ttc atg ggg tac atg aca aag gac aac     1248
Arg His Val Asn Ile Leu Leu Phe Met Gly Tyr Met Thr Lys Asp Asn
            405                 410                 415 ctg gcg att gtg act cag tgg tgt gaa ggc agc agt ctc tac aaa cac     1296
Leu Ala Ile Val Thr Gln Trp Cys Glu Gly Ser Ser Leu Tyr Lys His
        420                 425                 430 ctg cat gtc cag gag acc aaa ttc cag atg ttc cag cta att gac att     1344
Leu His Val Gln Glu Thr Lys Phe Gln Met Phe Gln Leu Ile Asp Ile
    435                 440                 445 gcc cga cag aca gct cag gga atg gac tat ttg cat gca aag aac atc     1392
Ala Arg Gln Thr Ala Gln Gly Met Asp Tyr Leu His Ala Lys Asn Ile
450                 455                 460 atc cac aga gac atg aaa tcc aac aat ata ttt ctc cat gaa ggc ctc     1440
Ile His Arg Asp Met Lys Ser Asn Asn Ile Phe Leu His Glu Gly Leu
465                 470                 475                 480 acg gtg aaa att gga gat ttt ggt ttg gca aca gtg aag tca cgc tgg     1488
Thr Val Lys Ile Gly Asp Phe Gly Leu Ala Thr Val Lys Ser Arg Trp
            485                 490                 495
```

```
agt ggt tct cag cag gtt gaa cag ccc act ggc tct gtg ctg tgg atg    1536
Ser Gly Ser Gln Gln Val Glu Gln Pro Thr Gly Ser Val Leu Trp Met
            500                 505                 510 gcc cca gaa gta atc cgg atg cag gat gac aac ccg ttc agc ttc cag    1584
Ala Pro Glu Val Ile Arg Met Gln Asp Asp Asn Pro Phe Ser Phe Gln
        515                 520                 525 tcc gac gtg tac tcg tac ggc atc gtg ctg tac gag ctg atg gct ggg    1632
Ser Asp Val Tyr Ser Tyr Gly Ile Val Leu Tyr Glu Leu Met Ala Gly
    530                 535                 540 gag ctt ccc tac gcc cac atc aac aac cga gac cag atc atc ttc atg    1680
Glu Leu Pro Tyr Ala His Ile Asn Asn Arg Asp Gln Ile Ile Phe Met
545                 550                 555                 560 gta ggc cgt ggg tat gca tcc cct gat ctc agc agg ctc tac aag aac    1728
Val Gly Arg Gly Tyr Ala Ser Pro Asp Leu Ser Arg Leu Tyr Lys Asn
                565                 570                 575 tgc ccc aag gca atg aag agg ttg gtg gct gac tgt gtg aag aaa gtc    1776
Cys Pro Lys Ala Met Lys Arg Leu Val Ala Asp Cys Val Lys Lys Val
            580                 585                 590 aaa gaa gag aga cct ttg ttt ccc cag atc ctg tct tcc atc gag ctg    1824
Lys Glu Glu Arg Pro Leu Phe Pro Gln Ile Leu Ser Ser Ile Glu Leu
        595                 600                 605 ctt cag cac tct ctg ccg aaa atc aac agg agc gcc tct gag cct tcc    1872
Leu Gln His Ser Leu Pro Lys Ile Asn Arg Ser Ala Ser Glu Pro Ser
    610                 615                 620 ctg cat cgg gca gct cac act gag gac atc aat gct tgc acg ctg act    1920
Leu His Arg Ala Ala His Thr Glu Asp Ile Asn Ala Cys Thr Leu Thr
625                 630                 635                 640 aca tcc cca agg cta cca gtc ttc tag                                1947
Thr Ser Pro Arg Leu Pro Val Phe
                645

<210> SEQ ID NO 27
<211> LENGTH: 648
<212> TYPE: PRT
<213> ORGANISM: Mus musculus

<400> SEQUENCE: 27

Met Glu His Ile Gln Gly Ala Trp Lys Thr Ile Ser Asn Gly Phe Gly
1               5                   10                  15

Leu Lys Asp Ala Val Phe Asp Gly Ser Ser Cys Ile Ser Pro Thr Ile
            20                  25                  30

Val Gln Gln Phe Gly Tyr Gln Arg Arg Ala Ser Asp Gly Lys Leu
        35                  40                  45

Thr Asp Ser Ser Lys Thr Ser Asn Thr Ile Arg Val Phe Leu Pro Asn
    50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu Gln Glu His Lys Gly Lys Lys Ala Arg Leu
            100                 105                 110

Asp Trp Asn Thr Asp Ala Ala Ser Leu Ile Gly Glu Glu Leu Gln Val
        115                 120                 125

Asp Phe Leu Asp His Val Pro Leu Thr Thr His Asn Phe Ala Arg Lys
    130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
```

-continued

```
                165                 170                 175
Ser Thr Lys Val Pro Thr Met Cys Val Asp Trp Ser Asn Ile Arg Gln
            180                 185                 190

Leu Leu Leu Phe Pro Asn Ser Thr Val Gly Asp Ser Gly Val Pro Ala
        195                 200                 205

Pro Pro Ser Phe Pro Met Arg Arg Met Arg Glu Ser Val Ser Arg Met
    210                 215                 220

Pro Ala Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
            245                 250                 255

Ser Thr Ser Thr Pro Asn Val His Met Val Ser Thr Thr Leu His Val
        260                 265                 270

Asp Ser Arg Met Ile Glu Asp Ala Ile Arg Ser His Ser Glu Ser Ala
    275                 280                 285

Ser Pro Ser Ala Leu Ser Ser Pro Asn Asn Leu Ser Pro Thr Gly
        290                 295                 300

Trp Ser Gln Pro Lys Thr Pro Val Pro Ala Gln Arg Glu Arg Ala Pro
305                 310                 315                 320

Gly Ser Gly Thr Gln Glu Lys Asn Lys Ile Arg Pro Arg Gly Gln Arg
            325                 330                 335

Asp Ser Ser Tyr Tyr Trp Glu Ile Glu Ala Ser Glu Val Met Leu Ser
        340                 345                 350

Thr Arg Ile Gly Ser Gly Ser Phe Gly Thr Val Tyr Lys Gly Lys Trp
    355                 360                 365

His Gly Asp Val Ala Val Lys Ile Leu Lys Val Val Asp Pro Thr Pro
370                 375                 380

Glu Gln Leu Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
            405                 410                 415

Leu Ala Ile Val Thr Gln Trp Cys Glu Gly Ser Ser Leu Tyr Lys His
        420                 425                 430

Leu His Val Gln Glu Thr Lys Phe Gln Met Phe Gln Leu Ile Asp Ile
    435                 440                 445

Ala Arg Gln Thr Ala Gln Gly Met Asp Tyr Leu His Ala Lys Asn Ile
    450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
            485                 490                 495

Ser Gly Ser Gln Gln Val Glu Gln Pro Thr Gly Ser Val Leu Trp Met
        500                 505                 510

Ala Pro Glu Val Ile Arg Met Gln Asp Asn Pro Phe Ser Phe Gln
    515                 520                 525

Ser Asp Val Tyr Ser Tyr Gly Ile Val Leu Tyr Glu Leu Met Ala Gly
    530                 535                 540

Glu Leu Pro Tyr Ala His Ile Asn Asn Arg Asp Gln Ile Ile Phe Met
545                 550                 555                 560

Val Gly Arg Gly Tyr Ala Ser Pro Asp Leu Ser Arg Leu Tyr Lys Asn
            565                 570                 575

Cys Pro Lys Ala Met Lys Arg Leu Val Ala Asp Cys Val Lys Lys Val
        580                 585                 590
```

```
Lys Glu Glu Arg Pro Leu Phe Pro Gln Ile Leu Ser Ser Ile Glu Leu
            595                 600                 605

Leu Gln His Ser Leu Pro Lys Ile Asn Arg Ser Ala Ser Glu Pro Ser
610                 615                 620

Leu His Arg Ala Ala His Thr Glu Asp Ile Asn Ala Cys Thr Leu Thr
625                 630                 635                 640

Thr Ser Pro Arg Leu Pro Val Phe
                645

<210> SEQ ID NO 28
<211> LENGTH: 1947
<212> TYPE: DNA
<213> ORGANISM: Homo sapiens
<220> FEATURE:
<221> NAME/KEY: CDS
<222> LOCATION: (1)..(1947)

<400> SEQUENCE: 28 atg gag cac ata cag gga gct tgg aag acg atc agc aat ggt ttt gga      48
Met Glu His Ile Gln Gly Ala Trp Lys Thr Ile Ser Asn Gly Phe Gly
1               5                   10                  15 ttc aaa gat gcc gtg ttt gat ggc tcc agc tgc atc tct cct aca ata      96
Phe Lys Asp Ala Val Phe Asp Gly Ser Ser Cys Ile Ser Pro Thr Ile
                20                  25                  30 gtt cag cag ttt ggc tat cag cgc cgg gca tca gat gat ggc aaa ctc     144
Val Gln Gln Phe Gly Tyr Gln Arg Arg Ala Ser Asp Asp Gly Lys Leu
            35                  40                  45 aca gat cct tct aag aca agc aac act atc cgt gtt ttc ttg ccg aac     192
Thr Asp Pro Ser Lys Thr Ser Asn Thr Ile Arg Val Phe Leu Pro Asn
        50                  55                  60 aag caa aga aca gtg gtc aat gtg cga aat gga atg agc ttg cat gac     240
Lys Gln Arg Thr Val Val Asn Val Arg Asn Gly Met Ser Leu His Asp
65                  70                  75                  80 tgc ctt atg aaa gca ctc aag gtg agg ggc ctg caa cca gag tgc tgt     288
Cys Leu Met Lys Ala Leu Lys Val Arg Gly Leu Gln Pro Glu Cys Cys
                85                  90                  95 gca gtg ttc aga ctt ctc cac gaa cac aaa ggt aaa aaa gca cgc tta     336
Ala Val Phe Arg Leu Leu His Glu His Lys Gly Lys Lys Ala Arg Leu
                100                 105                 110 gat tgg aat act gat gct gcg tct ttg att gga gaa gaa ctt caa gta     384
Asp Trp Asn Thr Asp Ala Ala Ser Leu Ile Gly Glu Glu Leu Gln Val
            115                 120                 125 gat ttc ctg gat cat gtt ccc ctc aca aca cac aac ttt gct cgg aag     432
Asp Phe Leu Asp His Val Pro Leu Thr Thr His Asn Phe Ala Arg Lys
        130                 135                 140 acg ttc ctg aag ctt gcc ttc tgt gac atc tgt cag aaa ttc ctg ctc     480
Thr Phe Leu Lys Leu Ala Phe Cys Asp Ile Cys Gln Lys Phe Leu Leu
145                 150                 155                 160 aat gga ttt cga tgt cag act tgt ggc tac aaa ttt cat gag cac tgt     528
Asn Gly Phe Arg Cys Gln Thr Cys Gly Tyr Lys Phe His Glu His Cys
                165                 170                 175 agc acc aaa gta cct act atg tgt gtg gac tgg agt aac atc aga caa     576
Ser Thr Lys Val Pro Thr Met Cys Val Asp Trp Ser Asn Ile Arg Gln
                180                 185                 190 ctc tta ttg ttt cca aat tcc act att ggt gat agt gga gtc cca gca     624
Leu Leu Leu Phe Pro Asn Ser Thr Ile Gly Asp Ser Gly Val Pro Ala
            195                 200                 205 cta cct tct ttg act atg cgt cgt atg cga gag tct gtt tcc agg atg     672
Leu Pro Ser Leu Thr Met Arg Arg Met Arg Glu Ser Val Ser Arg Met
        210                 215                 220
```

```
cct gtt agt tct cag cac aga tat tct aca cct cac gcc ttc acc ttt      720
Pro Val Ser Ser Gln His Arg Tyr Ser Thr Pro His Ala Phe Thr Phe
225                 230                 235                 240 aac acc tcc agt ccc tca tct gaa ggt tcc ctc tcc cag agg cag agg      768
Asn Thr Ser Ser Pro Ser Ser Glu Gly Ser Leu Ser Gln Arg Gln Arg
                245                 250                 255 tcg aca tcc aca cct aat gtc cac atg gtc agc acc acc ctg cct gtg     816
Ser Thr Ser Thr Pro Asn Val His Met Val Ser Thr Thr Leu Pro Val
            260                 265                 270 gac agc agg atg att gag gat gca att cga agt cac agc gaa tca gcc     864
Asp Ser Arg Met Ile Glu Asp Ala Ile Arg Ser His Ser Glu Ser Ala
        275                 280                 285 tca cct tca gcc ctg tcc agt agc ccc aac aat ctg agc cca aca ggc     912
Ser Pro Ser Ala Leu Ser Ser Ser Pro Asn Asn Leu Ser Pro Thr Gly
    290                 295                 300 tgg tca cag ccg aaa acc ccc gtg cca gca caa aga gag cgg gca cca     960
Trp Ser Gln Pro Lys Thr Pro Val Pro Ala Gln Arg Glu Arg Ala Pro
305                 310                 315                 320 gta tct ggg acc cag gag aaa aac aaa att agg cct cgt gga cag aga     1008
Val Ser Gly Thr Gln Glu Lys Asn Lys Ile Arg Pro Arg Gly Gln Arg
                325                 330                 335 gat tca agc tat tat tgg gaa ata gaa gcc agt gaa gtg atg ctg tcc     1056
Asp Ser Ser Tyr Tyr Trp Glu Ile Glu Ala Ser Glu Val Met Leu Ser
            340                 345                 350 act cgg att ggg tca ggc tct ttt gga act gtt tat aag ggt aaa tgg     1104
Thr Arg Ile Gly Ser Gly Ser Phe Gly Thr Val Tyr Lys Gly Lys Trp
        355                 360                 365 cac gga gat gtt gca gta aag atc cta aag gtt gtc gac cca acc cca     1152
His Gly Asp Val Ala Val Lys Ile Leu Lys Val Val Asp Pro Thr Pro
    370                 375                 380 gag caa ttc cag gcc ttc agg aat gag gtg gct gtt ctg cgc aaa aca     1200
Glu Gln Phe Gln Ala Phe Arg Asn Glu Val Ala Val Leu Arg Lys Thr
385                 390                 395                 400 cgg cat gtg aac att ctg ctt ttc atg ggg tac atg aca aag gac aac     1248
Arg His Val Asn Ile Leu Leu Phe Met Gly Tyr Met Thr Lys Asp Asn
                405                 410                 415 ctg gca att gtg acc cag tgg tgc gag ggc agc agc ctc tac aaa cac     1296
Leu Ala Ile Val Thr Gln Trp Cys Glu Gly Ser Ser Leu Tyr Lys His
            420                 425                 430 ctg cat gtc cag gag acc aag ttt cag atg ttc cag cta att gac att     1344
Leu His Val Gln Glu Thr Lys Phe Gln Met Phe Gln Leu Ile Asp Ile
        435                 440                 445 gcc cgg cag acg gct cag gga atg gac tat ttg cat gca aag aac atc     1392
Ala Arg Gln Thr Ala Gln Gly Met Asp Tyr Leu His Ala Lys Asn Ile
    450                 455                 460 atc cat aga gac atg aaa tcc aac aat ata ttt ctc cat gaa ggc tta     1440
Ile His Arg Asp Met Lys Ser Asn Asn Ile Phe Leu His Glu Gly Leu
465                 470                 475                 480 aca gtg aaa att gga gat ttt ggt ttg gca aca gta aag tca cgc tgg     1488
Thr Val Lys Ile Gly Asp Phe Gly Leu Ala Thr Val Lys Ser Arg Trp
                485                 490                 495 agt ggt tct cag cag gtt gaa caa cct act ggc tct gtc ctc tgg atg     1536
Ser Gly Ser Gln Gln Val Glu Gln Pro Thr Gly Ser Val Leu Trp Met
            500                 505                 510 gcc cca gag gtg atc cga atg cag gat aac aac cca ttc agt ttc cag     1584
Ala Pro Glu Val Ile Arg Met Gln Asp Asn Asn Pro Phe Ser Phe Gln
        515                 520                 525 tcg gat gtc tac tcc tat ggc atc gta ttg tat gaa ctg atg acg ggg     1632
Ser Asp Val Tyr Ser Tyr Gly Ile Val Leu Tyr Glu Leu Met Thr Gly
```

```
                        530                  535                  540
gag ctt cct tat tct cac atc aac aac cga gat cag atc atc ttc atg       1680
Glu Leu Pro Tyr Ser His Ile Asn Asn Arg Asp Gln Ile Ile Phe Met
545                 550                  555                  560 gtg ggc cga gga tat gcc tcc cca gat ctt agt aag cta tat aag aac       1728
Val Gly Arg Gly Tyr Ala Ser Pro Asp Leu Ser Lys Leu Tyr Lys Asn
                565                  570                  575 tgc ccc aaa gca atg aag agg ctg gta gct gac tgt gtg aag aaa gta       1776
Cys Pro Lys Ala Met Lys Arg Leu Val Ala Asp Cys Val Lys Lys Val
            580                  585                  590 aag gaa gag agg cct ctt ttt ccc cag atc ctg tct tcc att gag ctg       1824
Lys Glu Glu Arg Pro Leu Phe Pro Gln Ile Leu Ser Ser Ile Glu Leu
        595                  600                  605 ctc caa cac tct cta ccg aag atc aac cgg agc gct tcc gag cca tcc       1872
Leu Gln His Ser Leu Pro Lys Ile Asn Arg Ser Ala Ser Glu Pro Ser
    610                  615                  620 ttg cat cgg gca gcc cac act gag gat atc aat gct tgc acg ctg acc       1920
Leu His Arg Ala Ala His Thr Glu Asp Ile Asn Ala Cys Thr Leu Thr
625                  630                  635                  640 acg tcc ccg agg ctg cct gtc ttc tag                                    1947
Thr Ser Pro Arg Leu Pro Val Phe
                645

<210> SEQ ID NO 29
<211> LENGTH: 648
<212> TYPE: PRT
<213> ORGANISM: Homo sapiens

<400> SEQUENCE: 29

Met Glu His Ile Gln Gly Ala Trp Lys Thr Ile Ser Asn Gly Phe Gly
1               5                   10                  15

Phe Lys Asp Ala Val Phe Asp Gly Ser Ser Cys Ile Ser Pro Thr Ile
            20                  25                  30

Val Gln Gln Phe Gly Tyr Gln Arg Arg Ala Ser Asp Asp Gly Lys Leu
        35                  40                  45

Thr Asp Pro Ser Lys Thr Ser Asn Thr Ile Arg Val Phe Leu Pro Asn
    50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
            100                 105                 110

Asp Trp Asn Thr Asp Ala Ala Ser Leu Ile Gly Glu Glu Leu Gln Val
        115                 120                 125

Asp Phe Leu Asp His Val Pro Leu Thr Thr His Asn Phe Ala Arg Lys
    130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Ile Gly Asp Ser Gly Val Pro Ala
        195                 200                 205

Leu Pro Ser Leu Thr Met Arg Arg Met Arg Glu Ser Val Ser Arg Met
    210                 215                 220
```

-continued

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
            245                 250                 255

Ser Thr Ser Thr Pro Asn Val His Met Val Ser Thr Thr Leu Pro Val
        260                 265                 270

Asp Ser Arg Met Ile Glu Asp Ala Ile Arg Ser His Ser Glu Ser Ala
    275                 280                 285

Ser Pro Ser Ala Leu Ser Ser Pro Asn Asn Leu Ser Pro Thr Gly
290                 295                 300

Trp Ser Gln Pro Lys Thr Pro Val Pro Ala Gln Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
            340                 345                 350

Thr Arg Ile Gly Ser Gly Ser Phe Gly Thr Val Tyr Lys Gly Lys Trp
        355                 360                 365

His Gly Asp Val Ala Val Lys Ile Leu Lys Val Asp Pro Thr Pro
    370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
            420                 425                 430

Leu His Val Gln Glu Thr Lys Phe Gln Met Phe Gln Leu Ile Asp Ile
        435                 440                 445

Ala Arg Gln Thr Ala Gln Gly Met Asp Tyr Leu His Ala Lys Asn Ile
    450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
                485                 490                 495

Ser Gly Ser Gln Gln Val Glu Gln Pro Thr Gly Ser Val Leu Trp Met
            500                 505                 510

Ala Pro Glu Val Ile Arg Met Gln Asp Asn Asn Pro Phe Ser Phe Gln
        515                 520                 525

Ser Asp Val Tyr Ser Tyr Gly Ile Val Leu Tyr Glu Leu Met Thr Gly
    530                 535                 540

Glu Leu Pro Tyr Ser His Ile Asn Asn Arg Asp Gln Ile Ile Phe Met
545                 550                 555                 560

Val Gly Arg Gly Tyr Ala Ser Pro Asp Leu Ser Lys Leu Tyr Lys Asn
                565                 570                 575

Cys Pro Lys Ala Met Lys Arg Leu Val Ala Asp Cys Val Lys Lys Val
            580                 585                 590

Lys Glu Glu Arg Pro Leu Phe Pro Gln Ile Leu Ser Ser Ile Glu Leu
        595                 600                 605

Leu Gln His Ser Leu Pro Lys Ile Asn Arg Ser Ala Ser Glu Pro Ser
    610                 615                 620

Leu His Arg Ala Ala His Thr Glu Asp Ile Asn Ala Cys Thr Leu Thr
625                 630                 635                 640

```
Thr Ser Pro Arg Leu Pro Val Phe
            645

<210> SEQ ID NO 30
<211> LENGTH: 20
<212> TYPE: PRT
<213> ORGANISM: Artificial Sequence
<220> FEATURE:
<223> OTHER INFORMATION: N-terminal myristoylation signal sequence

<400> SEQUENCE: 30

Met Gly Ser Ser Lys Ser Lys Pro Lys Asp Pro Ser Gln Arg Arg Arg
1               5                   10                  15

Arg Ile Arg Thr
            20

<210> SEQ ID NO 31
<211> LENGTH: 34
<212> TYPE: DNA
<213> ORGANISM: Bacteriophage P1

<400> SEQUENCE: 31
ataacttcgt atagcataca ttatacgaag ttat                              34

<210> SEQ ID NO 32
<211> LENGTH: 34
<212> TYPE: DNA
<213> ORGANISM: Artificial Sequence
<220> FEATURE:
<223> OTHER INFORMATION: mutant loxP (lox71) sequence

<400> SEQUENCE: 32
taccgttcgt atagcataca ttatacgaag ttat                              34

<210> SEQ ID NO 33
<211> LENGTH: 34
<212> TYPE: DNA
<213> ORGANISM: Artificial Sequence
<220> FEATURE:
<223> OTHER INFORMATION: mutant loxP (lox66) sequence

<400> SEQUENCE: 33
ataacttcgt atagcataca ttatacgaac ggta                              34

<210> SEQ ID NO 34
<211> LENGTH: 2657
<212> TYPE: DNA
<213> ORGANISM: Mus musculus
<220> FEATURE:
<221> NAME/KEY: CDS
<222> LOCATION: (371)..(1837)

<400> SEQUENCE: 34
gcggggcggg gagaaggcgg gccggcggcg gcggcggcag caccgagtcg gcgggcggcc    60
ggcccagcgc ggcagcgcac gcgagtccgg gaccagcgga gcggaccgag cagcgtcctg   120
tggccggcac cgcggcggcc cagatccggc cagcagcgcg cgcccggacg ccgctgcctt   180
cagccggccc cgcccagcgc ccgccgcgcg gatgcggagc ggcgggcgcc cgaggccgcg   240
gcccggctag gcccagtcgc ccgcacgcgg cggcccgacg ctgcggccag gccggctggg   300
ctcagcctac cgagaagaga ctctgagcat catccctggg ttaccctgt ctctgggggc    360 cacggatacc atg aac gac gta gcc att gtg aag gag ggc tgg ctg cac     409
            Met Asn Asp Val Ala Ile Val Lys Glu Gly Trp Leu His
            1               5                   10
```

```
aaa cga ggg gaa tat att aaa acc tgg cgg cca cgc tac ttc ctc ctc     457
Lys Arg Gly Glu Tyr Ile Lys Thr Trp Arg Pro Arg Tyr Phe Leu Leu
 15              20                  25 aag aac gat ggc acc ttt att ggc tac aag gaa cgg cct cag gat gtg     505
Lys Asn Asp Gly Thr Phe Ile Gly Tyr Lys Glu Arg Pro Gln Asp Val
 30              35                  40                  45 gat cag cga gag tcc cca ctc aac aac ttc tca gtg gca caa tgc cag     553
Asp Gln Arg Glu Ser Pro Leu Asn Asn Phe Ser Val Ala Gln Cys Gln
                 50                  55                  60 ctg atg aag aca gag cgg cca agg ccc aac acc ttt atc atc cgc tgc     601
Leu Met Lys Thr Glu Arg Pro Arg Pro Asn Thr Phe Ile Ile Arg Cys
             65                  70                  75 ctg cag tgg acc aca gtc att gag cgc acc ttc cat gtg gaa acg cct     649
Leu Gln Trp Thr Thr Val Ile Glu Arg Thr Phe His Val Glu Thr Pro
         80                  85                  90 gag gag cgg gaa gaa tgg gcc acc gcc att cag act gtg gca gat gga     697
Glu Glu Arg Glu Glu Trp Ala Thr Ala Ile Gln Thr Val Ala Asp Gly
     95                 100                 105 ctc aag agg cag gaa gaa gag acg atg gac ttc cga tca ggc tca ccc     745
Leu Lys Arg Gln Glu Glu Glu Thr Met Asp Phe Arg Ser Gly Ser Pro
110                 115                 120                 125 agt gac aac tca ggg gct gaa gag atg gag gtg tcc ctg gcc aag ccc     793
Ser Asp Asn Ser Gly Ala Glu Glu Met Glu Val Ser Leu Ala Lys Pro
                130                 135                 140 aag cac cgt gtg acc atg aac gag ttt gag tac ctg aag cta ctg ggc     841
Lys His Arg Val Thr Met Asn Glu Phe Glu Tyr Leu Lys Leu Leu Gly
            145                 150                 155 aag ggc acc ttt ggg aag gtg att ctg gtg aaa gag aag gcc aca ggc     889
Lys Gly Thr Phe Gly Lys Val Ile Leu Val Lys Glu Lys Ala Thr Gly
        160                 165                 170 cgc tac tat gcc atg aag atc ctc aag aag gag gtc atc gtc gcc aag     937
Arg Tyr Tyr Ala Met Lys Ile Leu Lys Lys Glu Val Ile Val Ala Lys
    175                 180                 185 gat gag gtt gcc cac acg ctt act gag aac cgt gtc ctg cag aac tct     985
Asp Glu Val Ala His Thr Leu Thr Glu Asn Arg Val Leu Gln Asn Ser
190                 195                 200                 205 agg cat ccc ttc ctt acg gcc ctc aag tac tca ttc cag acc cac gac    1033
Arg His Pro Phe Leu Thr Ala Leu Lys Tyr Ser Phe Gln Thr His Asp
                210                 215                 220 cgc ctc tgc ttt gtc atg gag tat gcc aac ggg ggc gag ctc ttc ttc    1081
Arg Leu Cys Phe Val Met Glu Tyr Ala Asn Gly Gly Glu Leu Phe Phe
            225                 230                 235 cac ctg tct cga gag cgt gtg ttc tcc gag gac cgg gcc cgc ttc tat    1129
His Leu Ser Arg Glu Arg Val Phe Ser Glu Asp Arg Ala Arg Phe Tyr
        240                 245                 250 ggt gcg gag att gtg tct gcc ctg gac tac ttg cac tcc gag aag aac    1177
Gly Ala Glu Ile Val Ser Ala Leu Asp Tyr Leu His Ser Glu Lys Asn
    255                 260                 265 gtg gtg tac cgg gac ctg aag ctg gag aac ctc atg ctg gac aag gac    1225
Val Val Tyr Arg Asp Leu Lys Leu Glu Asn Leu Met Leu Asp Lys Asp
270                 275                 280                 285 ggg cac atc aag ata acg gac ttc ggg ctg tgc aag gag ggg atc aag    1273
Gly His Ile Lys Ile Thr Asp Phe Gly Leu Cys Lys Glu Gly Ile Lys
                290                 295                 300 gac ggt gcc act atg aag aca ttc tgc gga acg ccg gag tac ctg gcc    1321
Asp Gly Ala Thr Met Lys Thr Phe Cys Gly Thr Pro Glu Tyr Leu Ala
            305                 310                 315 cct gag gtg ctg gag gac aac gac tac ggc cgt gca gtg gac tgg tgg    1369
Pro Glu Val Leu Glu Asp Asn Asp Tyr Gly Arg Ala Val Asp Trp Trp
```

|  |  |  |  |  |  |  |  |  |  |  |  |  |  |  |  |
|---|---|---|---|---|---|---|---|---|---|---|---|---|---|---|---|
|  | 320 |  |  |  | 325 |  |  |  |  | 330 |  |  |  |  |  |
| ggg | ctg | ggc | gtg | gtc | atg | tac | gag | atg | atg | tgt | ggc | cgc | ctg | ccc | ttc |
| Gly | Leu | Gly | Val | Val | Met | Tyr | Glu | Met | Met | Cys | Gly | Arg | Leu | Pro | Phe |
|  | 335 |  |  |  | 340 |  |  |  |  | 345 |  |  |  |  |  |

1417

| tac | aac | cag | gac | cac | gag | aag | ctg | ttc | gag | ctg | atc | ctc | atg | gag | gag |
|---|---|---|---|---|---|---|---|---|---|---|---|---|---|---|---|
| Tyr | Asn | Gln | Asp | His | Glu | Lys | Leu | Phe | Glu | Leu | Ile | Leu | Met | Glu | Glu |
| 350 |  |  |  |  | 355 |  |  |  |  | 360 |  |  |  |  | 365 |

1465

| atc | cgc | ttc | ccg | cgc | aca | ctc | ggc | cct | gag | gcc | aag | tcc | ctg | ctc | tcc |
|---|---|---|---|---|---|---|---|---|---|---|---|---|---|---|---|
| Ile | Arg | Phe | Pro | Arg | Thr | Leu | Gly | Pro | Glu | Ala | Lys | Ser | Leu | Leu | Ser |
|  |  |  |  | 370 |  |  |  |  | 375 |  |  |  |  | 380 |  |

1513

| ggg | ctg | ctc | aag | aag | gac | cct | aca | cag | agg | ctc | ggt | ggg | ggc | tcc | gag |
|---|---|---|---|---|---|---|---|---|---|---|---|---|---|---|---|
| Gly | Leu | Leu | Lys | Lys | Asp | Pro | Thr | Gln | Arg | Leu | Gly | Gly | Gly | Ser | Glu |
|  |  | 385 |  |  |  |  | 390 |  |  |  |  | 395 |  |  |  |

1561

| gat | gcc | aag | gag | atc | atg | cag | cac | cgg | ttc | ttt | gcc | aac | atc | gtg | tgg |
|---|---|---|---|---|---|---|---|---|---|---|---|---|---|---|---|
| Asp | Ala | Lys | Glu | Ile | Met | Gln | His | Arg | Phe | Phe | Ala | Asn | Ile | Val | Trp |
| 400 |  |  |  |  | 405 |  |  |  |  | 410 |  |  |  |  |  |

1609

| cag | gat | gtg | tat | gag | aag | aag | ctg | agc | cca | cct | ttc | aag | ccc | cag | gtc |
|---|---|---|---|---|---|---|---|---|---|---|---|---|---|---|---|
| Gln | Asp | Val | Tyr | Glu | Lys | Lys | Leu | Ser | Pro | Pro | Phe | Lys | Pro | Gln | Val |
|  | 415 |  |  |  |  | 420 |  |  |  |  | 425 |  |  |  |  |

1657

| acc | tct | gag | act | gac | acc | agg | tat | ttc | gat | gag | gag | ttc | aca | gct | cag |
|---|---|---|---|---|---|---|---|---|---|---|---|---|---|---|---|
| Thr | Ser | Glu | Thr | Asp | Thr | Arg | Tyr | Phe | Asp | Glu | Glu | Phe | Thr | Ala | Gln |
| 430 |  |  |  |  | 435 |  |  |  |  | 440 |  |  |  |  | 445 |

1705

| atg | atc | acc | atc | acg | ccg | cct | gat | caa | gtt | ctc | cta | ctc | agc | cag | tgg |
|---|---|---|---|---|---|---|---|---|---|---|---|---|---|---|---|
| Met | Ile | Thr | Ile | Thr | Pro | Pro | Asp | Gln | Val | Leu | Leu | Leu | Ser | Gln | Trp |
|  |  |  |  | 450 |  |  |  |  | 455 |  |  |  |  | 460 |  |

1753

| cac | agc | ctg | agg | cct | ggg | gca | gcg | gct | ggc | agc | tcc | acg | ctc | ctc | tgc |
|---|---|---|---|---|---|---|---|---|---|---|---|---|---|---|---|
| His | Ser | Leu | Arg | Pro | Gly | Ala | Ala | Ala | Gly | Ser | Ser | Thr | Leu | Leu | Cys |
|  |  |  | 465 |  |  |  |  | 470 |  |  |  |  | 475 |  |  |

1801

| att | gcc | gag | tcc | aga | agc | ccc | gca | tgg | atc | atc | tga | acctgatgtt |
|---|---|---|---|---|---|---|---|---|---|---|---|---|
| Ile | Ala | Glu | Ser | Arg | Ser | Pro | Ala | Trp | Ile | Ile |  |  |
|  |  | 480 |  |  |  |  | 485 |  |  |  |  |  |

1847

| ttgtttctcg | gatgcgctgg | ggaggaacct | tgccagcctc | caggaccagg | ggaggatgtt | 1907 |
|---|---|---|---|---|---|---|
| tctactgtgg | gcagcagcct | acctcccagc | caggtcagga | ggaaaactat | cctgggtttt | 1967 |
| ttcttaattt | atttcatcca | gtttgagacc | acacatgtgg | cctcagtgcc | agaacaatt | 2027 |
| agattcatgt | agaaaactat | taaggactga | cgcgaccatg | tgcaatgtgg | gctcatgggt | 2087 |
| ctgggtgggt | cccgtcactg | cccccattgg | cctgtccacc | ctggccgcca | cctgtctcta | 2147 |
| gggtccaggg | ccaaagtcca | gcaagaaggc | accagaagca | ccccctgtg | gtatgctaac | 2207 |
| tggccctctc | cctctgggcg | gggagaggtc | acagctgctt | cagccctagg | gctggatggg | 2267 |
| atggccaggg | ctcaagtgag | gttgacagag | gaacaagaat | ccagtttgtt | gctgtgtccc | 2327 |
| atgctgttca | gagacattta | ggggatttta | atcttggtga | caggagagcc | cctgccctcc | 2387 |
| cgcacccgct | cccgcgtggt | ggctcttagc | gggtaccctg | ggagcgcctg | cctcacgtga | 2447 |
| gcccttctcc | tagcacttgt | cctttagat | gctttccctc | tcccgctgtc | cgtcaccctg | 2507 |
| gcctgtcccc | tccggccag | acgctggcca | ttgctgcacc | atgtcgtttt | ttacaacatt | 2567 |
| cagcttcagc | attttactga | ttataataag | aaactgtccc | tccaaattca | ataaaaattg | 2627 |
| cttttcaagc | ttgaaaaaaa | aaaaaaaaaa |  |  |  | 2657 |

<210> SEQ ID NO 35
<211> LENGTH: 488
<212> TYPE: PRT
<213> ORGANISM: Mus musculus

<400> SEQUENCE: 35

Met Asn Asp Val Ala Ile Val Lys Glu Gly Trp Leu His Lys Arg Gly

-continued

```
1               5                   10                  15
Glu Tyr Ile Lys Thr Trp Arg Pro Arg Tyr Phe Leu Leu Lys Asn Asp
                20                  25                  30
Gly Thr Phe Ile Gly Tyr Lys Glu Arg Pro Gln Asp Val Asp Gln Arg
                35                  40                  45
Glu Ser Pro Leu Asn Asn Phe Ser Val Ala Gln Cys Gln Leu Met Lys
 50                  55                  60
Thr Glu Arg Pro Arg Pro Asn Thr Phe Ile Ile Arg Cys Leu Gln Trp
 65                  70                  75                  80
Thr Thr Val Ile Glu Arg Thr Phe His Val Glu Thr Pro Glu Glu Arg
                85                  90                  95
Glu Glu Trp Ala Thr Ala Ile Gln Thr Val Ala Asp Gly Leu Lys Arg
                100                 105                 110
Gln Glu Glu Glu Thr Met Asp Phe Arg Ser Gly Ser Pro Ser Asp Asn
                115                 120                 125
Ser Gly Ala Glu Glu Met Glu Val Ser Leu Ala Lys Pro Lys His Arg
 130                 135                 140
Val Thr Met Asn Glu Phe Glu Tyr Leu Lys Leu Leu Gly Lys Gly Thr
 145                 150                 155                 160
Phe Gly Lys Val Ile Leu Val Lys Glu Lys Ala Thr Gly Arg Tyr Tyr
                165                 170                 175
Ala Met Lys Ile Leu Lys Lys Glu Val Ile Val Ala Lys Asp Glu Val
                180                 185                 190
Ala His Thr Leu Thr Glu Asn Arg Val Leu Gln Asn Ser Arg His Pro
                195                 200                 205
Phe Leu Thr Ala Leu Lys Tyr Ser Phe Gln Thr His Asp Arg Leu Cys
 210                 215                 220
Phe Val Met Glu Tyr Ala Asn Gly Gly Glu Leu Phe Phe His Leu Ser
 225                 230                 235                 240
Arg Glu Arg Val Phe Ser Glu Asp Arg Ala Arg Phe Tyr Gly Ala Glu
                245                 250                 255
Ile Val Ser Ala Leu Asp Tyr Leu His Ser Glu Lys Asn Val Val Tyr
                260                 265                 270
Arg Asp Leu Lys Leu Glu Asn Leu Met Leu Asp Lys Asp Gly His Ile
                275                 280                 285
Lys Ile Thr Asp Phe Gly Leu Cys Lys Glu Gly Ile Lys Asp Gly Ala
 290                 295                 300
Thr Met Lys Thr Phe Cys Gly Thr Pro Glu Tyr Leu Ala Pro Glu Val
 305                 310                 315                 320
Leu Glu Asp Asn Asp Tyr Gly Arg Ala Val Asp Trp Trp Gly Leu Gly
                325                 330                 335
Val Val Met Tyr Glu Met Met Cys Gly Arg Leu Pro Phe Tyr Asn Gln
                340                 345                 350
Asp His Glu Lys Leu Phe Glu Leu Ile Leu Met Glu Glu Ile Arg Phe
                355                 360                 365
Pro Arg Thr Leu Gly Pro Glu Ala Lys Ser Leu Leu Ser Gly Leu Leu
                370                 375                 380
Lys Lys Asp Pro Thr Gln Arg Leu Gly Gly Gly Ser Glu Asp Ala Lys
 385                 390                 395                 400
Glu Ile Met Gln His Arg Phe Phe Ala Asn Ile Val Trp Gln Asp Val
                405                 410                 415
Tyr Glu Lys Lys Leu Ser Pro Pro Phe Lys Pro Gln Val Thr Ser Glu
                420                 425                 430
```

```
Thr Asp Thr Arg Tyr Phe Asp Glu Glu Phe Thr Ala Gln Met Ile Thr
        435                 440                 445

Ile Thr Pro Pro Asp Gln Val Leu Leu Leu Ser Gln Trp His Ser Leu
    450                 455                 460

Arg Pro Gly Ala Ala Gly Ser Ser Thr Leu Leu Cys Ile Ala Glu
465             470                 475                 480

Ser Arg Ser Pro Ala Trp Ile Ile
                485

<210> SEQ ID NO 36
<211> LENGTH: 2878
<212> TYPE: DNA
<213> ORGANISM: Homo sapiens
<220> FEATURE:
<221> NAME/KEY: CDS
<222> LOCATION: (425)..(1867)

<400> SEQUENCE: 36
cggcaggacc gagcgcggca ggcggctggc ccagcgcagc cagcgcggcc cgaaggacgg      60
gagcaggcgg ccgagcaccg agcgctgggc accgggcacc gagcggcggc ggcacgcgag     120
gcccggcccc gagcagcgcc cccgcccgcc gcggcctcca gcccggcccc gcccagcgcc     180
ggcccgcggg gatgcggagc ggcgggcgcc ggaggccgcg gcccggctag gcccgcgctc     240
gcgcccggac gcggcggccc ggggcttagg gaaggccgag ccagcctggg tcaaagaagt     300
caaaggggct gcctggagga ggcagcctgt cagctggtgc atcagaggct gtggccaggc     360
cagctgggct cggggagcgc cagcctgaga ggagcgcgtg agcgtcgcgg gagcctcggg     420 cacc atg agc gac gtg gct att gtg aag gag ggt tgg ctg cac aaa cga     469
     Met Ser Asp Val Ala Ile Val Lys Glu Gly Trp Leu His Lys Arg
     1               5                   10                  15 ggg gag tac atc aag acc tgg cgg cca cgc tac ttc ctc ctc aag aat     517
Gly Glu Tyr Ile Lys Thr Trp Arg Pro Arg Tyr Phe Leu Leu Lys Asn
                20                  25                  30 gat ggc acc ttc att ggc tac aag gag cgg ccg cag gat gtg gac caa     565
Asp Gly Thr Phe Ile Gly Tyr Lys Glu Arg Pro Gln Asp Val Asp Gln
            35                  40                  45 cgt gag gct ccc ctc aac aac ttc tct gtg gcg cag tgc cag ctg atg     613
Arg Glu Ala Pro Leu Asn Asn Phe Ser Val Ala Gln Cys Gln Leu Met
        50                  55                  60 aag acg gag cgg ccc cgg ccc aac acc ttc atc atc cgc tgc ctg cag     661
Lys Thr Glu Arg Pro Arg Pro Asn Thr Phe Ile Ile Arg Cys Leu Gln
    65                  70                  75 tgg acc act gtc atc gaa cgc acc ttc cat gtg gag act cct gag gag     709
Trp Thr Thr Val Ile Glu Arg Thr Phe His Val Glu Thr Pro Glu Glu
80                  85                  90                  95 cgg gag gag tgg aca acc gcc atc cag act gtg gct gac ggc ctc aag     757
Arg Glu Glu Trp Thr Thr Ala Ile Gln Thr Val Ala Asp Gly Leu Lys
                100                 105                 110 aag cag gag gag gag gag atg gac ttc cgg tcg ggc tca ccc agt gac     805
Lys Gln Glu Glu Glu Glu Met Asp Phe Arg Ser Gly Ser Pro Ser Asp
            115                 120                 125 aac tca ggg gct gaa gag atg gag gtg tcc ctg gcc aag ccc aag cac     853
Asn Ser Gly Ala Glu Glu Met Glu Val Ser Leu Ala Lys Pro Lys His
        130                 135                 140 cgc gtg acc atg aac gag ttt gag tac ctg aag ctg ctg ggc aag ggc     901
Arg Val Thr Met Asn Glu Phe Glu Tyr Leu Lys Leu Leu Gly Lys Gly
    145                 150                 155 act ttc ggc aag gtg atc ctg gtg aag gag aag gcc aca ggc cgc tac     949
```

```
Thr Phe Gly Lys Val Ile Leu Val Lys Glu Lys Ala Thr Gly Arg Tyr
160             165                 170                 175 tac gcc atg aag atc ctc aag aag gaa gtc atc gtg gcc aag gac gag       997
Tyr Ala Met Lys Ile Leu Lys Lys Glu Val Ile Val Ala Lys Asp Glu
                180                 185                 190 gtg gcc cac aca ctc acc gag aac cgc gtc ctg cag aac tcc agg cac      1045
Val Ala His Thr Leu Thr Glu Asn Arg Val Leu Gln Asn Ser Arg His
            195                 200                 205 ccc ttc ctc aca gcc ctg aag tac tct ttc cag acc cac gac cgc ctc      1093
Pro Phe Leu Thr Ala Leu Lys Tyr Ser Phe Gln Thr His Asp Arg Leu
            210                 215                 220 tgc ttt gtc atg gag tac gcc aac ggg ggc gag ctg ttc ttc cac ctg      1141
Cys Phe Val Met Glu Tyr Ala Asn Gly Gly Glu Leu Phe Phe His Leu
225                 230                 235 tcc cgg gag cgt gtg ttc tcc gag gac cgg gcc cgc ttc tat ggc gct      1189
Ser Arg Glu Arg Val Phe Ser Glu Asp Arg Ala Arg Phe Tyr Gly Ala
240                 245                 250                 255 gag att gtg tca gcc ctg gac tac ctg cac tcg gag aag aac gtg gtg      1237
Glu Ile Val Ser Ala Leu Asp Tyr Leu His Ser Glu Lys Asn Val Val
                260                 265                 270 tac cgg gac ctc aag ctg gag aac ctc atg ctg gac aag gac ggg cac      1285
Tyr Arg Asp Leu Lys Leu Glu Asn Leu Met Leu Asp Lys Asp Gly His
            275                 280                 285 att aag atc aca gac ttc ggg ctg tgc aag gag ggg atc aag gac ggt      1333
Ile Lys Ile Thr Asp Phe Gly Leu Cys Lys Glu Gly Ile Lys Asp Gly
            290                 295                 300 gcc acc atg aag acc ttt tgc ggc aca cct gag tac ctg gcc ccc gag      1381
Ala Thr Met Lys Thr Phe Cys Gly Thr Pro Glu Tyr Leu Ala Pro Glu
305                 310                 315 gtg ctg gag gac aat gac tac ggc cgt gca gtg gac tgg tgg ggg ctg      1429
Val Leu Glu Asp Asn Asp Tyr Gly Arg Ala Val Asp Trp Trp Gly Leu
320                 325                 330                 335 ggc gtg gtc atg tac gag atg atg tgc ggt cgc ctg ccc ttc tac aac      1477
Gly Val Val Met Tyr Glu Met Met Cys Gly Arg Leu Pro Phe Tyr Asn
                340                 345                 350 cag gac cat gag aag ctt ttt gag ctc atc ctc atg gag gag atc cgc      1525
Gln Asp His Glu Lys Leu Phe Glu Leu Ile Leu Met Glu Glu Ile Arg
            355                 360                 365 ttc ccg cgc acg ctt ggt ccc gag gcc aag tcc ttg ctt tca ggg ctg      1573
Phe Pro Arg Thr Leu Gly Pro Glu Ala Lys Ser Leu Leu Ser Gly Leu
            370                 375                 380 ctc aag aag gac ccc aag cag agg ctt ggc ggg ggc tcc gag gac gcc      1621
Leu Lys Lys Asp Pro Lys Gln Arg Leu Gly Gly Gly Ser Glu Asp Ala
385                 390                 395 aag gag atc atg cag cat cgc ttc ttt gcc ggt atc gtg tgg cag cac      1669
Lys Glu Ile Met Gln His Arg Phe Phe Ala Gly Ile Val Trp Gln His
400                 405                 410                 415 gtg tac gag aag aag ctc agc cca ccc ttc aag ccc cag gtc acg tcg      1717
Val Tyr Glu Lys Lys Leu Ser Pro Pro Phe Lys Pro Gln Val Thr Ser
                420                 425                 430 gag act gac acc agg tat ttt gat gag gag ttc acg gcc cag atg atc      1765
Glu Thr Asp Thr Arg Tyr Phe Asp Glu Glu Phe Thr Ala Gln Met Ile
            435                 440                 445 acc atc aca cca cct gac caa gat gac agc atg gag tgt gtg gac agc      1813
Thr Ile Thr Pro Pro Asp Gln Asp Asp Ser Met Glu Cys Val Asp Ser
            450                 455                 460 gag cgc agg ccc cac ttc ccc cag ttc tcc tac tcg gcc agc ggc acg      1861
Glu Arg Arg Pro His Phe Pro Gln Phe Ser Tyr Ser Ala Ser Gly Thr
465                 470                 475
```

```
gcc tga ggcggcggtg gactgcgctg gacgatagct tggagggatg gagaggcggc     1917
Ala
480 ctcgtgccat gatctgtatt taatggtttt tatttctcgg gtgcatttga gagaagccac     1977 gctgtcctct cgagcccaga tggaaagacg tttttgtgct gtgggcagca ccctcccccg     2037 cagcggggta gggaagaaaa ctatcctgcg ggttttaatt tatttcatcc agtttgttct     2097 ccgggtgtgg cctcagccct cagaacaatc cgattcacgt agggaaatgt taaggacttc     2157 tgcagctatg cgcaatgtgg cattgggggg ccgggcaggt cctgcccatg tgtccctca      2217 ctctgtcagc cagccgccct gggctgtctg tcaccagcta tctgtcatct ctctggggcc     2277 ctgggcctca gttcaacctg gtggcaccag atgcaacctc actatggtat gctggccagc     2337 accctctcct gggggtggca ggcacacagc agccccccag cactaaggcc gtgtctctga     2397 ggacgtcatc ggaggctggg cccctgggat gggaccaggg atgggggatg ggccagggtt     2457 tacccagtgg gacagaggag caaggtttaa atttgttatt gtgtattatg ttgttcaaat     2517 gcattttggg ggttttttaat ctttgtgaca ggaaagccct ccccttccc cttctgtgtc     2577 acagttcttg gtgactgtcc caccgggagc ctccccctca gatgatctct ccacggtagc     2637 acttgacctt ttcgacgctt aacctttccg ctgtcgcccc aggccctccc tgactccctg     2697 tgggggtggc catccctggg cccctccacg cctcctggcc agacgctgcc gctgccgctg     2757 caccacggcg ttttttttaca acattcaact ttagtatttt tactattata atataatatg     2817 gaaccttccc tccaaattct tcaataaaag ttgcttttca aaaaaaaaa aaaaaaaaa      2877 a                                                                    2878

<210> SEQ ID NO 37
<211> LENGTH: 480
<212> TYPE: PRT
<213> ORGANISM: Homo sapiens

<400> SEQUENCE: 37

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175
```

```
Ala Met Lys Ile Leu Lys Lys Glu Val Ile Val Ala Lys Asp Val
            180                 185                 190
Ala His Thr Leu Thr Glu Asn Arg Val Leu Gln Asn Ser Arg His Pro
            195                 200                 205
Phe Leu Thr Ala Leu Lys Tyr Ser Phe Gln Thr His Asp Arg Leu Cys
            210                 215                 220
Phe Val Met Glu Tyr Ala Asn Gly Gly Glu Leu Phe Phe His Leu Ser
225                 230                 235                 240
Arg Glu Arg Val Phe Ser Glu Asp Arg Ala Arg Phe Tyr Gly Ala Glu
                245                 250                 255
Ile Val Ser Ala Leu Asp Tyr Leu His Ser Glu Lys Asn Val Val Tyr
            260                 265                 270
Arg Asp Leu Lys Leu Glu Asn Leu Met Leu Asp Lys Asp Gly His Ile
            275                 280                 285
Lys Ile Thr Asp Phe Gly Leu Cys Lys Glu Gly Ile Lys Asp Gly Ala
            290                 295                 300
Thr Met Lys Thr Phe Cys Gly Thr Pro Glu Tyr Leu Ala Pro Glu Val
305                 310                 315                 320
Leu Glu Asp Asn Asp Tyr Gly Arg Ala Val Asp Trp Trp Gly Leu Gly
                325                 330                 335
Val Val Met Tyr Glu Met Met Cys Gly Arg Leu Pro Phe Tyr Asn Gln
            340                 345                 350
Asp His Glu Lys Leu Phe Glu Leu Ile Leu Met Glu Glu Ile Arg Phe
            355                 360                 365
Pro Arg Thr Leu Gly Pro Glu Ala Lys Ser Leu Leu Ser Gly Leu Leu
            370                 375                 380
Lys Lys Asp Pro Lys Gln Arg Leu Gly Gly Gly Ser Glu Asp Ala Lys
385                 390                 395                 400
Glu Ile Met Gln His Arg Phe Phe Ala Gly Ile Val Trp Gln His Val
                405                 410                 415
Tyr Glu Lys Lys Leu Ser Pro Pro Phe Lys Pro Gln Val Thr Ser Glu
            420                 425                 430
Thr Asp Thr Arg Tyr Phe Asp Glu Glu Phe Thr Ala Gln Met Ile Thr
            435                 440                 445
Ile Thr Pro Pro Asp Gln Asp Asp Ser Met Glu Cys Val Asp Ser Glu
            450                 455                 460
Arg Arg Pro His Phe Pro Gln Phe Ser Tyr Ser Ala Ser Gly Thr Ala
465                 470                 475                 480

<210> SEQ ID NO 38
<211> LENGTH: 1521
<212> TYPE: DNA
<213> ORGANISM: Mus musculus
<220> FEATURE:
<221> NAME/KEY: CDS
<222> LOCATION: (126)..(680)

<400> SEQUENCE: 38
ccgcgcccgc cgccgtgctc tgtatgccgc gttctcccgg cgcagccgcc gccgatagtc      60
tgagccggag gagccgccgc cgccgcggtt aatgtggttg ggtcggggct gagcaggcca     120 ccaag atg cct cag tcc aag tcc cgg aag atc gcc atc ctg ggc tac cgg    170
      Met Pro Gln Ser Lys Ser Arg Lys Ile Ala Ile Leu Gly Tyr Arg
      1               5                  10                  15 tct gtg gga aag tcc tca ttg aca att cag ttt gtt gaa ggc caa ttt      218
Ser Val Gly Lys Ser Ser Leu Thr Ile Gln Phe Val Glu Gly Gln Phe
                20                  25                  30
```

| | | | | | | | | | | | | | | | |
|---|---|---|---|---|---|---|---|---|---|---|---|---|---|---|---|
| gtt | gat | tcc | tac | gat | cca | acc | ata | gag | aac | acg | ttc | acc | aag | ttg | atc | 266 |
| Val | Asp | Ser | Tyr | Asp | Pro | Thr | Ile | Glu | Asn | Thr | Phe | Thr | Lys | Leu | Ile |
| | | | 35 | | | | 40 | | | | | 45 | | | |

```
gtt gat tcc tac gat cca acc ata gag aac acg ttc acc aag ttg atc      266
Val Asp Ser Tyr Asp Pro Thr Ile Glu Asn Thr Phe Thr Lys Leu Ile
            35                  40                  45 acg gta aat ggt caa gag tat cat ctt cag ctt gta gac aca gcg ggg      314
Thr Val Asn Gly Gln Glu Tyr His Leu Gln Leu Val Asp Thr Ala Gly
        50                  55                  60 cag gat gaa tat tcc att ttt cct cag aca tac tcc ata gat att aat      362
Gln Asp Glu Tyr Ser Ile Phe Pro Gln Thr Tyr Ser Ile Asp Ile Asn
65                  70                  75 ggt tat att ctt gtg tat tct gtt aca tca atc aaa agt ttt gaa gta      410
Gly Tyr Ile Leu Val Tyr Ser Val Thr Ser Ile Lys Ser Phe Glu Val
80                  85                  90                  95 att aaa gtt atc cat ggc aag ttg ttg gat atg gtg ggg aaa gtg cag      458
Ile Lys Val Ile His Gly Lys Leu Leu Asp Met Val Gly Lys Val Gln
            100                 105                 110 ata cct att atg ttg gtt gga aat aag aag gac ctg cat atg gaa agg      506
Ile Pro Ile Met Leu Val Gly Asn Lys Lys Asp Leu His Met Glu Arg
        115                 120                 125 gtg atc agc tat gaa gaa gga aag gct ttg gca gaa tct tgg aat gca      554
Val Ile Ser Tyr Glu Glu Gly Lys Ala Leu Ala Glu Ser Trp Asn Ala
130                 135                 140 gct ttt ttg gaa tct tct gct aaa gaa aat caa act gct gtt gat gtt      602
Ala Phe Leu Glu Ser Ser Ala Lys Glu Asn Gln Thr Ala Val Asp Val
145                 150                 155 ttt aaa agg ata att ttg gaa gca gaa aag att gat gga gca gct tca      650
Phe Lys Arg Ile Ile Leu Glu Ala Glu Lys Ile Asp Gly Ala Ala Ser
160                 165                 170                 175 caa gga aag tct tcg tgc tcg gtg atg tga caattctgct gcagagcctg        700
Gln Gly Lys Ser Ser Cys Ser Val Met
            180 cggacactgg ggatatattc cacctgagga agcaaactgc ccgtcatcct tgaagataaa   760
actatgcttc tgttttcttc tgttaacctg aaagatgtca tttgggtcag ggtcctccc   820
cttttcagatt atgttaacgt ctgactctgt ccaaatgagt tcacctccat tttcaaattt  880
taaacaatca tattttcaat ttatatattg tatttcttaa tattatgacc aagaattta   940
tcggcattaa tttttttcagt gtagtttgtt gtttaaaata atgtaatcat caaaatgata 1000
cacatgttac actactatta actaggcttc aatatatcag tgtttatttc attgtgttaa 1060
atgtatactt gtaaataaaa tagctgcaaa ccttaagcct ttgagctact tggtgtggtt 1120
tttaaaccag gaaccatgtt aggatggggc atgggcgtgc acatcgtttg tttttgtttt 1180
gtttgctttt tcgagacagg gtttctctat gtaacagcac tggctgtcct ggaacccact 1240
ctgtagacca ggctgtcctc gaactcgaga tttgcctgcc tctgcctccc aagtgctggg 1300
attaaaggcg tgcaccacca ctgcctggct gtacagtgtt ccctggttct attaccccg  1360
gctcttttac ctcacttggc cccaacacct ccctcttaca ttttcacatt ctctcctgca 1420
tccagttatt gcctcctgtt ggcatgttag ttcatctggt ctctatcttc cgtgttaact 1480
gcagtggcca tgtcatgcct agtaaacagt attttactgc a                      1521
```

<210> SEQ ID NO 39
<211> LENGTH: 184
<212> TYPE: PRT
<213> ORGANISM: Mus musculus

<400> SEQUENCE: 39

```
Met Pro Gln Ser Lys Ser Arg Lys Ile Ala Ile Leu Gly Tyr Arg Ser
1               5                   10                  15
```

```
Val Gly Lys Ser Ser Leu Thr Ile Gln Phe Val Glu Gly Gln Phe Val
         20                  25                  30

Asp Ser Tyr Asp Pro Thr Ile Glu Asn Thr Phe Thr Lys Leu Ile Thr
         35                  40                  45

Val Asn Gly Gln Glu Tyr His Leu Gln Leu Val Asp Thr Ala Gly Gln
 50                  55                  60

Asp Glu Tyr Ser Ile Phe Pro Gln Thr Tyr Ser Ile Asp Ile Asn Gly
 65                  70                  75                  80

Tyr Ile Leu Val Tyr Ser Val Thr Ser Ile Lys Ser Phe Glu Val Ile
                 85                  90                  95

Lys Val Ile His Gly Lys Leu Leu Asp Met Val Gly Lys Val Gln Ile
                100                 105                 110

Pro Ile Met Leu Val Gly Asn Lys Lys Asp Leu His Met Glu Arg Val
                115                 120                 125

Ile Ser Tyr Glu Glu Gly Lys Ala Leu Ala Glu Ser Trp Asn Ala Ala
130                 135                 140

Phe Leu Glu Ser Ser Ala Lys Glu Asn Gln Thr Ala Val Asp Val Phe
145                 150                 155                 160

Lys Arg Ile Ile Leu Glu Ala Glu Lys Ile Asp Gly Ala Ala Ser Gln
                165                 170                 175

Gly Lys Ser Ser Cys Ser Val Met
                180
```

<210> SEQ ID NO 40
<211> LENGTH: 2092
<212> TYPE: DNA
<213> ORGANISM: Homo sapiens
<220> FEATURE:
<221> NAME/KEY: CDS
<222> LOCATION: (414)..(968)

<400> SEQUENCE: 40

```
ggcgtaatta aaaagcggcg gaagaaggtg ggagggtcat gacgcagcga gtttcagtcg      60
tgacttttct gggggcatcg cggcgtcccc tttttttgcc tttaaagtaa aacgtcgccc     120
cgacgcaccc cccgcgtatt tcgggggcg gaggcggcgg gccacggcgc gaagaggggc      180
ggtgctgacg ccggccggtc acgtgggcgt gttgtggggg ggaggggcgc cgccgcgcgg     240
tcggttccgg gcggttggga gcgcgcgagc tagcgagcga gaggcagccg cgccccgccgc    300 cgccctgct ctgtatgccg ctctctcccg gcgcggccgc cgccgatcac agcagcagga      360
gccaccgccg ccgcggttga tgtggttggg ccggggctga ggaggccgcc aag atg       416
                                                             Met
                                                              1 ccg cag tcc aag tcc cgg aag atc gcg atc ctg ggc tac cgg tct gtg      464
Pro Gln Ser Lys Ser Arg Lys Ile Ala Ile Leu Gly Tyr Arg Ser Val
          5                  10                  15 ggg aaa tcc tca ttg acg att caa ttt gtt gaa ggc caa ttt gtg gac      512
Gly Lys Ser Ser Leu Thr Ile Gln Phe Val Glu Gly Gln Phe Val Asp
         20                  25                  30 tcc tac gat cca acc ata gaa aac act ttt aca aag ttg atc aca gta      560
Ser Tyr Asp Pro Thr Ile Glu Asn Thr Phe Thr Lys Leu Ile Thr Val
         35                  40                  45 aat gga caa gaa tat cat ctt caa ctt gta gac aca gcc ggg caa gat      608
Asn Gly Gln Glu Tyr His Leu Gln Leu Val Asp Thr Ala Gly Gln Asp
 50                  55                  60                  65 gaa tat tct atc ttt cct cag aca tac tcc ata gat att aat ggc tat      656
Glu Tyr Ser Ile Phe Pro Gln Thr Tyr Ser Ile Asp Ile Asn Gly Tyr
```

-continued

|  |  |  | 70 |  |  |  | 75 |  |  |  | 80 |  |  |  |  |
|---|---|---|---|---|---|---|---|---|---|---|---|---|---|---|---|
| att | ctt | gtg | tat | tct | gtt | aca | tca | atc | aaa | agt | ttt | gaa | gtg | att | aaa | 704 |
| Ile | Leu | Val | Tyr | Ser | Val | Thr | Ser | Ile | Lys | Ser | Phe | Glu | Val | Ile | Lys |
|  |  |  | 85 |  |  |  | 90 |  |  |  | 95 |  |  |  |  |
| gtt | atc | cat | ggc | aaa | ttg | ttg | gat | atg | gtg | ggg | aaa | gta | caa | ata | cct | 752 |
| Val | Ile | His | Gly | Lys | Leu | Leu | Asp | Met | Val | Gly | Lys | Val | Gln | Ile | Pro |
|  |  | 100 |  |  |  |  | 105 |  |  |  |  | 110 |  |  |  |
| att | atg | ttg | gtt | ggg | aat | aag | aaa | gac | ctg | cat | atg | gaa | agg | gtg | atc | 800 |
| Ile | Met | Leu | Val | Gly | Asn | Lys | Lys | Asp | Leu | His | Met | Glu | Arg | Val | Ile |
|  | 115 |  |  |  |  | 120 |  |  |  |  | 125 |  |  |  |  | agt tat gaa gaa ggg aaa gct ttg gca gaa tct tgg aat gca gct ttt    848
Ser Tyr Glu Glu Gly Lys Ala Leu Ala Glu Ser Trp Asn Ala Ala Phe
130             135                 140                 145 ttg gaa tct tct gct aaa gaa aat cag act gct gtg gat gtt ttt cga    896
Leu Glu Ser Ser Ala Lys Glu Asn Gln Thr Ala Val Asp Val Phe Arg
        150                 155                 160 agg ata att ttg gag gca gaa aaa atg gac ggg gca gct tca caa ggc    944
Arg Ile Ile Leu Glu Ala Glu Lys Met Asp Gly Ala Ala Ser Gln Gly
            165                 170                 175 aag tct tca tgc tcg gtg atg tga ttctgctgca aagcctgagg acactgggaa   998
Lys Ser Ser Cys Ser Val Met
            180 tatattctac ctgaagaagc aaactgcccg ttctccttga agataaacta tgcttctttt  1058
ttcttctgtt aacctgaaag atatcatttg ggtcagagct cccctccctt cagattatgt  1118
taactctgag tctgtccaaa tgagttcact tccattttca aattttaagc aatcatattt  1178
tcaatttata tattgtattt cttaatatta tgaccaagaa ttttatcggc attaattttt  1238
cagtgtagtt tgttgtttaa ataatgtaa tcatcaaaat gatgcatatt gttacactac   1298
tattaactag gcttcagtat atcagtgttt atttcattgt gttaaatgta tacttgtaaa  1358
taaaatagct gcaaacctca gtcctttgtg ctacttgatg tggctttcaa agaagagaag  1418
ccttgtcctg agtttctcac ttggcttcag gaaggcccca ggttggattc agaaaccag   1478
tgaagatgtg gccacaggag gaggtgtgct gaggtggctg ctgaccgtgg actccctgcg  1538
cagtggcctg cagatgttgg ggctgggtta cagctgattg aagctgagtg gccctggggg  1598
gtctgtgagg ggagttcctc cccagtgatg aaattctctc cttccaccct caaatcccta  1658
gaccttgact gaaatgctcc gtggtcggga gcctggtcaa ggaggaggag ctgctgagag  1718
gcattgttcg cccttgctca tagcttagct cgatgtccgt gtcagacagg agatgattga  1778
gaacagcctt gcctgtcact gtcctagaac acctggagt ttagtgttct gtgtcagagt   1838
cttgggagcc tccttcagac ccagatgacg ggcctccctc tgtccaagga gcagctgtaa  1898
aggagaagag ggatttcatt tgtttggtgg ctgttacctt gtctgtaagt caaacttgga  1958
gttgagcagt gcttttaaaa cgattcccct ttgcagctaa aatttcacag gctatttct   2018
aatacgtaag caaatgttac cattgacttt attaataaaa tatagttttg ctttgcaaaa  2078
aaaaaaaaaa aaaa                                                    2092

<210> SEQ ID NO 41
<211> LENGTH: 184
<212> TYPE: PRT
<213> ORGANISM: Homo sapiens

<400> SEQUENCE: 41

Met Pro Gln Ser Lys Ser Arg Lys Ile Ala Ile Leu Gly Tyr Arg Ser
1               5                   10                  15

-continued

```
Val Gly Lys Ser Ser Leu Thr Ile Gln Phe Val Glu Gly Gln Phe Val
         20                  25                  30

Asp Ser Tyr Asp Pro Thr Ile Glu Asn Thr Phe Thr Lys Leu Ile Thr
         35                  40                  45

Val Asn Gly Gln Glu Tyr His Leu Gln Leu Val Asp Thr Ala Gly Gln
 50                  55                  60

Asp Glu Tyr Ser Ile Phe Pro Gln Thr Tyr Ser Ile Asp Ile Asn Gly
65                  70                  75                  80

Tyr Ile Leu Val Tyr Ser Val Thr Ser Ile Lys Ser Phe Glu Val Ile
                 85                  90                  95

Lys Val Ile His Gly Lys Leu Leu Asp Met Val Gly Lys Val Gln Ile
            100                 105                 110

Pro Ile Met Leu Val Gly Asn Lys Lys Asp Leu His Met Glu Arg Val
            115                 120                 125

Ile Ser Tyr Glu Glu Gly Lys Ala Leu Ala Glu Ser Trp Asn Ala Ala
        130                 135                 140

Phe Leu Glu Ser Ser Ala Lys Glu Asn Gln Thr Ala Val Asp Val Phe
145                 150                 155                 160

Arg Arg Ile Ile Leu Glu Ala Glu Lys Met Asp Gly Ala Ala Ser Gln
                165                 170                 175

Gly Lys Ser Ser Cys Ser Val Met
            180

<210> SEQ ID NO 42
<211> LENGTH: 1410
<212> TYPE: DNA
<213> ORGANISM: Mus musculus
<220> FEATURE:
<221> NAME/KEY: CDS
<222> LOCATION: (86)..(436)

<400> SEQUENCE: 42
cgcgtttctc atgctcaccg tgtaggaagc agttttatca cggactggca ttgcaatttt       60
ctgcttcttg ctcttatcgg atgcc atg gct acc cag cgg gca cac agg gca      112
                           Met Ala Thr Gln Arg Ala His Arg Ala
                             1               5 gag aca cct gca cac ccc aac cgc ctg tgg atc tgg gag aag cac gtg      160
Glu Thr Pro Ala His Pro Asn Arg Leu Trp Ile Trp Glu Lys His Val
 10              15                  20                  25 tac ttg gat gag ttt cgt cga agc tgg ctg ccc gta gtc atc aag agt      208
Tyr Leu Asp Glu Phe Arg Arg Ser Trp Leu Pro Val Val Ile Lys Ser
                 30                  35                  40 aat gaa aaa ttc cag gtg atc ttg cgc cag gaa gat gtc acc ttg ggg      256
Asn Glu Lys Phe Gln Val Ile Leu Arg Gln Glu Asp Val Thr Leu Gly
             45                  50                  55 gaa gct atg tcc ccc agt cag ctg gtg cct tac gag ctg cct tta atg      304
Glu Ala Met Ser Pro Ser Gln Leu Val Pro Tyr Glu Leu Pro Leu Met
         60                  65                  70 tgg caa ctg tac ccc aag gac agg tac cga agc tgc gac tcc atg tat      352
Trp Gln Leu Tyr Pro Lys Asp Arg Tyr Arg Ser Cys Asp Ser Met Tyr
     75                  80                  85 tgg cag atc ctg tac cat atc aag ttt aga gac gtg gag gac atg ttg      400
Trp Gln Ile Leu Tyr His Ile Lys Phe Arg Asp Val Glu Asp Met Leu
 90                  95                 100                 105 ctt gaa ctg ata gac tcg gag tcc aac gat gaa taa cccagacccg            446
Leu Glu Leu Ile Asp Ser Glu Ser Asn Asp Glu
                110                 115 gtcctgcagc tcctgtctgc cttgcccagg cctggcccca caggggagat gttggtactt     506
```

-continued

```
atgttctgtc tgttcgctag tcatgtcctt tttcctctac actgggctcc aagaagaaaa    566
ctctggccag acgctgcccc ttcccatgct gctgttgcct gctcggctgc cttggttggt    626
ccctcagctc tgctgactcc ctggcaaggg gctccagaga agatcccagt tctcctcacc    686
tcctctaggt gctcagtggt gtctgtgcct ctgatgatct tagctgattg actcttccgt    746
ctttcccttt ggcctcacaa gacaactagt gtctctgact tatgaacttg ccttcttcct    806
cacgggtccc tcagcagtac atacaccatg agggacaaga cctcgtcatt ggaatctggc    866
caggccccag atcagccatc actcaaggtg ttgtgcctgt acccacctga cctgtgaagc    926
cccacctacc cagcaaacat aggctttgat tgcagagcgg tgtaagacct gagagctctc    986
ttgcccttcc ttagaaccta ggtgcttgca gccagggata tgcaaacctg gggcctatgg   1046
cctcactaga acaagaggcc aggcagtggg cctggttcag atgggccctc tgattgcctg   1106
tgtgcaggct tcctctctgg gtgttcaggt tctgtattta gtgtaaacac gtcctgtcgc   1166
tgattaaata tttcactcac ctaagttggg ccaaatcggc ttccatcctt gaccgagatg   1226
ccaataaatg agggagagaa gactgctccg ggtctcccca gagaagccag ggtcacccag   1286
ggaagccttg gtctcctagt aagaatgttg aaagggaatg tgtgggattt tatgtggttc   1346
tattttagag atacggctgg atttaataaa gctttgtaga actttaaaaa aaaaaaaaaa   1406
aaaa                                                                1410
```

<210> SEQ ID NO 43
<211> LENGTH: 116
<212> TYPE: PRT
<213> ORGANISM: Mus musculus

<400> SEQUENCE: 43

```
Met Ala Thr Gln Arg Ala His Arg Ala Glu Thr Pro Ala His Pro Asn
 1               5                   10                  15

Arg Leu Trp Ile Trp Glu Lys His Val Tyr Leu Asp Glu Phe Arg Arg
            20                  25                  30

Ser Trp Leu Pro Val Val Ile Lys Ser Asn Glu Lys Phe Gln Val Ile
        35                  40                  45

Leu Arg Gln Glu Asp Val Thr Leu Gly Glu Ala Met Ser Pro Ser Gln
    50                  55                  60

Leu Val Pro Tyr Glu Leu Pro Leu Met Trp Gln Leu Tyr Pro Lys Asp
65                  70                  75                  80

Arg Tyr Arg Ser Cys Asp Ser Met Tyr Trp Gln Ile Leu Tyr His Ile
                85                  90                  95

Lys Phe Arg Asp Val Glu Asp Met Leu Leu Glu Leu Ile Asp Ser Glu
            100                 105                 110

Ser Asn Asp Glu
        115
```

<210> SEQ ID NO 44
<211> LENGTH: 1405
<212> TYPE: DNA
<213> ORGANISM: Homo sapiens
<220> FEATURE:
<221> NAME/KEY: CDS
<222> LOCATION: (131)..(475)

<400> SEQUENCE: 44

```
gtcctcccgc cccgccgctt ggtggcggcc gcatgctgcc cggatataaa gggtcggccc     60
cacatcccag ggaccagcga gcggccttga gaggctctgg ctcttgcttc ttaggcggcc    120
```

```
cgaggacgcc atg gcc gag tgc ccg aca ctc ggg gag gca gtc acc gac     169
           Met Ala Glu Cys Pro Thr Leu Gly Glu Ala Val Thr Asp
            1               5                  10 cac ccg gac cgc ctg tgg gcc tgg gag aag ttc gtg tat ttg gac gag     217
His Pro Asp Arg Leu Trp Ala Trp Glu Lys Phe Val Tyr Leu Asp Glu
 15              20                  25 aag cag cac gcc tgg ctg ccc tta acc atc gag ata aag gat agg tta     265
Lys Gln His Ala Trp Leu Pro Leu Thr Ile Glu Ile Lys Asp Arg Leu
 30              35                  40                  45 cag tta cgg gtg ctc ttg cgt cgg gaa gac gtc gtc ctg ggg agg cct     313
Gln Leu Arg Val Leu Leu Arg Arg Glu Asp Val Val Leu Gly Arg Pro
                 50                  55                  60 atg acc ccc acc cag ata ggc cca agc ctg ctg cct atc atg tgg cag     361
Met Thr Pro Thr Gln Ile Gly Pro Ser Leu Leu Pro Ile Met Trp Gln
             65                  70                  75 ctc tac cct gat gga cga tac cga tcc tca gac tcc agt ttc tgg cgc     409
Leu Tyr Pro Asp Gly Arg Tyr Arg Ser Ser Asp Ser Ser Phe Trp Arg
             80                  85                  90 tta gtg tac cac atc aag att gac ggc gtg gag gac atg ctt ctc gag     457
Leu Val Tyr His Ile Lys Ile Asp Gly Val Glu Asp Met Leu Leu Glu
         95                 100                 105 ctg ctg cca gat gac tga tgtcttggca gcacctgtct cctttcaccc            505
Leu Leu Pro Asp Asp
110 cagggcctga gcctggccag cctacaatgg ggatgttgtg tttctgttca ccttcgttta    565 ctatgcctgt gtcttctcca ccacgctggg gtctgggagg aatggacaga cagaggatga    625 gctctaccca gggcctgcag gacctgcctg tagcccactc tgctcgcctt agcactacca    685 ctcctgccaa ggaggattcc atttggcaga gcttcttcca ggtgcccagc tatacctgtg    745 cctcggcttt tctcagctgg atgatggtct tcagcctctt tctgtccctt ctgtccctca    805 cagcactagt atttcatgtt gcacacccac tcagctccgt gaacttgtga gaacacagcc    865 gattcacctg agcaggacct ctgaaaccct ggaccagtgg tctcacatgg tgctacgcct    925 gcatgtaaac acgcctgcaa acgctgcctg ccggtaaaca cgcctgcaaa cgctgcctgc    985 ccgtaaacac gcctgcaaac gctgcctgcc cacacaggtt cacgtgcagc tcaaggaaag    1045 gcctgaaagg agcccttatc tgtgctcagg actcagaagc ctctgggtca gtggtccaca    1105 tcccgggacg cagcaggagg ccaggccggc gagccctgtg gatgagccct cagaacccct    1165 ggcttgccca cgtggaaaag ggatagaggt tgggtttccc cccttttata gatggtcacg    1225 cacctgggtg ttacaaagtt gtatgtggca tgaatacttt ttgtaatgat tgattaaatg    1285 caagatagtt tatctaactt cgtgcggaat cagcttctat ccttgactta gattctggtg    1345 gagagaagtg agaataggca gcccccaaat aaaaatatt catggaaaaa aaaaaaaaa     1405
```

<210> SEQ ID NO 45
<211> LENGTH: 114
<212> TYPE: PRT
<213> ORGANISM: Homo sapiens

<400> SEQUENCE: 45

Met Ala Glu Cys Pro Thr Leu Gly Glu Ala Val Thr Asp His Pro Asp
 1               5                  10                  15

Arg Leu Trp Ala Trp Glu Lys Phe Val Tyr Leu Asp Glu Lys Gln His
            20                  25                  30

Ala Trp Leu Pro Leu Thr Ile Glu Ile Lys Asp Arg Leu Gln Leu Arg
        35                  40                  45

```
Val Leu Leu Arg Arg Glu Asp Val Val Leu Gly Arg Pro Met Thr Pro
         50                  55                  60

Thr Gln Ile Gly Pro Ser Leu Leu Pro Ile Met Trp Gln Leu Tyr Pro
 65                  70                  75                  80

Asp Gly Arg Tyr Arg Ser Ser Asp Ser Ser Phe Trp Arg Leu Val Tyr
                 85                  90                  95

His Ile Lys Ile Asp Gly Val Glu Asp Met Leu Leu Glu Leu Leu Pro
             100                 105                 110

Asp Asp
```

```
<210> SEQ ID NO 46
<211> LENGTH: 5395
<212> TYPE: DNA
<213> ORGANISM: Mus musculus
<220> FEATURE:
<221> NAME/KEY: CDS
<222> LOCATION: (102)..(1679)

<400> SEQUENCE: 46
```

| | | |
|---|---|---|
| tgaacttgag gagccagtct ggggcctagg cgcagacgca ttgagcttaa gcagccggtg | | 60 |
| atggcggcag cagccgtgga gtctgcggcg ggtccgggcc c atg agg cga cga cgg<br>                                                      Met Arg Arg Arg Arg<br>                                                      1               5 | | 116 |

```
agg cgg gac ggc ttt tac cta gcg cct gac ttc cga cac agg gaa gct       164
Arg Arg Asp Gly Phe Tyr Leu Ala Pro Asp Phe Arg His Arg Glu Ala
             10                  15                  20 gag gac atg gca gga gtg ttt gac ata gac ctg gac cag cca gaa gat       212
Glu Asp Met Ala Gly Val Phe Asp Ile Asp Leu Asp Gln Pro Glu Asp
         25                  30                  35 gca ggc tct gag gat gag ctg gag gag ggg ggt cag tta aat gaa agc       260
Ala Gly Ser Glu Asp Glu Leu Glu Glu Gly Gly Gln Leu Asn Glu Ser
     40                  45                  50 atg gac cat ggg gga gtt gga cca tat gaa ctt ggc atg gaa cat tgt       308
Met Asp His Gly Gly Val Gly Pro Tyr Glu Leu Gly Met Glu His Cys
 55                  60                  65 gag aaa ttt gaa atc tca gaa act agt gtg aac aga ggg cca gaa aaa       356
Glu Lys Phe Glu Ile Ser Glu Thr Ser Val Asn Arg Gly Pro Glu Lys
 70                  75                  80                  85 atc aga cca gaa tgt ttt gag cta ctt cgg gta ctt ggt aaa ggg ggc       404
Ile Arg Pro Glu Cys Phe Glu Leu Leu Arg Val Leu Gly Lys Gly Gly
                 90                  95                 100 tat gga aag gtt ttt caa gta cga aaa gta aca gga gca aat act ggg       452
Tyr Gly Lys Val Phe Gln Val Arg Lys Val Thr Gly Ala Asn Thr Gly
             105                 110                 115 aag ata ttt gcc atg aag gtg ctt aaa aag gca atg ata gtg agg aat       500
Lys Ile Phe Ala Met Lys Val Leu Lys Lys Ala Met Ile Val Arg Asn
         120                 125                 130 gct aag gac acg gcc cac acg aaa gca gag cgg aac att ctg gag gaa       548
Ala Lys Asp Thr Ala His Thr Lys Ala Glu Arg Asn Ile Leu Glu Glu
     135                 140                 145 gtg aaa cac cct ttc att gtg gac ctg att tat gcc ttt cag acc gga       596
Val Lys His Pro Phe Ile Val Asp Leu Ile Tyr Ala Phe Gln Thr Gly
150                 155                 160                 165 gga aag ctc tac ctc atc ctc gag tat ctc agt gga gga gaa cta ttt       644
Gly Lys Leu Tyr Leu Ile Leu Glu Tyr Leu Ser Gly Gly Glu Leu Phe
                 170                 175                 180 atg cag tta gaa aga gag gga ata ttc atg gaa gac aca gcg tgc ttt       692
Met Gln Leu Glu Arg Glu Gly Ile Phe Met Glu Asp Thr Ala Cys Phe
             185                 190                 195
```

| | | | | |
|---|---|---|---|---|
| tac ttg gct gaa atc tcc atg gct ttg ggg cat tta cat caa aaa ggg<br>Tyr Leu Ala Glu Ile Ser Met Ala Leu Gly His Leu His Gln Lys Gly<br>       200                    205                   210 | | | | 740 |
| atc atc tac aga gac ctg aag ccg gag aac atc atg ctt aat cac caa<br>Ile Ile Tyr Arg Asp Leu Lys Pro Glu Asn Ile Met Leu Asn His Gln<br>215                    220                    225 | | | | 788 |
| ggt cac gtg aaa cta aca gac ttt gga cta tgc aaa gaa tct att cat<br>Gly His Val Lys Leu Thr Asp Phe Gly Leu Cys Lys Glu Ser Ile His<br>230                    235                    240                   245 | | | | 836 |
| gat gga aca gtc acg cac aca ttt tgt gga aca ata gaa tac atg gcc<br>Asp Gly Thr Val Thr His Thr Phe Cys Gly Thr Ile Glu Tyr Met Ala<br>                250                    255                   260 | | | | 884 |
| cct gaa atc tta atg aga agc ggc cac aac cgt gct gtg gat tgg tgg<br>Pro Glu Ile Leu Met Arg Ser Gly His Asn Arg Ala Val Asp Trp Trp<br>              265                    270                   275 | | | | 932 |
| agt ttg gga gca tta atg tat gac atg ctg act gga gca cct cca ttc<br>Ser Leu Gly Ala Leu Met Tyr Asp Met Leu Thr Gly Ala Pro Pro Phe<br>      280                    285                    290 | | | | 980 |
| act ggg gag aat aga aag aaa aca att gac aaa atc ctc aaa tgt aaa<br>Thr Gly Glu Asn Arg Lys Lys Thr Ile Asp Lys Ile Leu Lys Cys Lys<br>295                    300                    305 | | | | 1028 |
| ctt aat ttg cct ccc tac ctc aca caa gaa gct cga gat ctg ctt aaa<br>Leu Asn Leu Pro Pro Tyr Leu Thr Gln Glu Ala Arg Asp Leu Leu Lys<br>310                    315                    320                   325 | | | | 1076 |
| aag ctg ctg aaa aga aat gct gct tct cgt ctt gga gct ggc cct ggg<br>Lys Leu Leu Lys Arg Asn Ala Ala Ser Arg Leu Gly Ala Gly Pro Gly<br>                330                    335                   340 | | | | 1124 |
| gat gct gga gaa gtc caa gct cat cct ttt ttc aga cac att aac tgg<br>Asp Ala Gly Glu Val Gln Ala His Pro Phe Phe Arg His Ile Asn Trp<br>                  345                    350                   355 | | | | 1172 |
| gaa gaa ctt ctg gct cgg aag gtg gaa cct ccc ttt aag cct ctg ttg<br>Glu Glu Leu Leu Ala Arg Lys Val Glu Pro Pro Phe Lys Pro Leu Leu<br>            360                    365                   370 | | | | 1220 |
| caa tct gaa gag gat gtg agt cag ttt gat tca aag ttt aca cgt cag<br>Gln Ser Glu Glu Asp Val Ser Gln Phe Asp Ser Lys Phe Thr Arg Gln<br>375                    380                    385 | | | | 1268 |
| aca cct gtt gac agc cct gat gac tcc act ctc agt gaa agt gcc aac<br>Thr Pro Val Asp Ser Pro Asp Asp Ser Thr Leu Ser Glu Ser Ala Asn<br>390                    395                    400                   405 | | | | 1316 |
| cag gtc ttt ctg ggt ttt aca tat gtg gct cca tct gta ctt gaa agt<br>Gln Val Phe Leu Gly Phe Thr Tyr Val Ala Pro Ser Val Leu Glu Ser<br>                410                    415                   420 | | | | 1364 |
| gtg aaa gaa aag ttt tca ttt gaa cca aaa atc cga tct cct aga aga<br>Val Lys Glu Lys Phe Ser Phe Glu Pro Lys Ile Arg Ser Pro Arg Arg<br>            425                    430                   435 | | | | 1412 |
| ttt att ggt agt cca cga aca cct gtc agc cca gtc aaa ttc tct cct<br>Phe Ile Gly Ser Pro Arg Thr Pro Val Ser Pro Val Lys Phe Ser Pro<br>                440                    445                   450 | | | | 1460 |
| ggg gat ttc tgg gga cga ggt gct tca gcc agc acg gca aat cct cag<br>Gly Asp Phe Trp Gly Arg Gly Ala Ser Ala Ser Thr Ala Asn Pro Gln<br>            455                    460                   465 | | | | 1508 |
| acc cct gtg gaa tac cca atg gaa aca agt ggg ata gag cag atg gat<br>Thr Pro Val Glu Tyr Pro Met Glu Thr Ser Gly Ile Glu Gln Met Asp<br>470                    475                    480                   485 | | | | 1556 |
| gtg aca gtg agc ggg gaa gca tca gcg cca ctt cca atc cga caa ccc<br>Val Thr Val Ser Gly Glu Ala Ser Ala Pro Leu Pro Ile Arg Gln Pro<br>                490                    495                   500 | | | | 1604 |
| aac tcc ggg ccg tac aaa aaa caa gct ttt cct atg atc tcc aaa cgg<br>Asn Ser Gly Pro Tyr Lys Lys Gln Ala Phe Pro Met Ile Ser Lys Arg | | | | 1652 |

```
                505                 510                 515
cca gag cac ctg cgg atg aat cta tga tgaaacaatg cttttattaa          1699
Pro Glu His Leu Arg Met Asn Leu
         520                 525 tgcaaaatca aaaggaaac aaatccggga aggggatgtg tgagcatcct gcaatataaa   1759
aacaagaata aaatggcagt ctcaaagagt cagtgtcatt acctggaatg ctttcgatgg  1819
aggaaaaaat aaacatggat tttaaaaaat caatcaaaaa tggtgcaaaa aaaaaaataa  1879
acccacaaaa aactcaagca aaatagtatt gtggaatcca cagacacatc agctgactgg  1939
ttcctatcct agcaacatct cggcgttcgc aagggttctc atgctgatgg ctgcaaactg  1999
acagtattaa gggtaggatg ttgcttcgga atcaccgttg aaatctgatg atgtcaaata  2059
agggttatcc taataggcaa agtttgagat tgcctgtaat acttgcaact aaggacaaat  2119
tagcatgcaa gctttgtcaa acttttcca gcaacacaga atcaaagaca aagaaactt    2179 tatcgattga tgttttacgt gcaaacaacc tgaatctttt ttttatataa atatatattt  2239
ttcaaataga ttttgattc agctcattat gaaaacatc ccaaacttta aaatgcgaag    2299
ttattggttg gtgtgaagaa agccagcttc tgtcttctct tgatgaaata aaatgcaaat  2359
gatcattgtt aaccacagct gtggcttgtc tgagggcctg gggtggacct ggggtgtttt  2419
tttaatcttt tgttttagt aacctagctg caatacttgt ctgtaatact agggggaaa    2479 agtctgttta atcattttta cttgcagtac tgctgtgtgt ttggcgtaac tgcaagcctt  2539
gggacaggca gaagttgtat gatctacatt gcatccttgt cctgggcctg cactacactg  2599
gaaacagtat caccacctgt tcttatacca gtatttgagt caagccttgg tcgaggaggg  2659
acagaagaga atcaggctaa agtgcataaa gagggcagta agcggggag atagacctgc   2719 aggggagagg gtgttgccac gggcgtctct ctcgactctt tacagcacat tggtgtggtt  2779
ctaggtttac tttgtactgt tatgctgttt accttcctta acaattttct tttttgagaa  2839
tctaaaaaag aaaaaatgg tgtttttttc ccctcctgca ctggggctac attttttcact 2899 tataaaaata tttgatggcc ttttgatgaa tgtcttccat aacgaataag aaaacctagt  2959
ggcttaattt aggaaacatg ttaacaagac actgttttg aaattgtaac aaagtcaaca   3019
taagtgattt acaggtacaa agaataaaaa taaaggtaac tttacctttc ttaaatactt  3079
cctgccttaa ggagcatttc catgactagc tggtgaaagg gtttaatatc tgcagagctt  3139
tataaaatat actgcagtgc atactggtct aggtagatgg tcacacagtg agtcctgtca  3199
cgccactctg ttggtctttt ttgtcttggt aatagttgca gcccttgggt ttcttttatgc 3259 agatgctctt gctgtgttcc tcaaaggatc caagccataa aattctttat gcatgtcaca  3319
gtcaggattg acccagacct tgcttattca aattgtaatt gaagtgagat gggaagaaat  3379
gttaacagtg agcaaaaata gaaccttgag aggctggaga gatgactcag cagttaagaa  3439
ctctggctac ttttccagag gtcctgagtt caatcccagc acccacatga tagcttacat  3499
ctataaactg tagtctcgtt ggatcaaatg ttctcttaca tgcacatgtg cagacaaaac  3559
atccacatac ataaaaatct taaaaaaaaa aaacaaaaaa aaaaaaccag agccatggca  3619
gatgactgga aatactgccc ttcaattgtg gcagcaaacg tccatctgga cagagaattt  3679
ctttttttat catttaaatg gtcattcctg attctcttga ctgtagcagc attttgagaa  3739
cttcataatt gtagcagtaa attaggagct gcagtaatga ttaagaatgt tcttcattct  3799
ttgagagttt gtggtatctt aaaaaataga acccctcaaa aaacctatgg caatgcatta  3859
taggaatcat ttcagactgc aaatggcttg tgctactctg atatctgttt ctaaatgtgt  3919
```

```
ttactaacta tagcgttgac tgcctggcca aattccaata aaactttttac actaaatgat    3979 tcctccttag ccctagttgc tagtaatatg tgcactgtga ccaccccata aactgttaat    4039
aaactgttca tagaattact gccagcaata gtggcaaata tcgcaacgtt tttgtgtaga    4099
acgcattaat tgtacacctt ctgtcgactt ccatctacac aaatatatag cttttctatc    4159
acaacattaa gtgaaattga tgctgtggca agtttattga gaactttca taaatggata    4219 tccctactat gactgtgaaa acatgtcagg tgtcacatga gtgtcacaga cagaaagcac    4279
atgcctatgc aatatggcct actctgtatt tatttgtaaa aactgaagca taatttaaag    4339
tgtatatcaa tactactctg agtttctaag agaggtgttc atgcttgtac caggtaagtg    4399
aataaaaaaa aagattaagt gcttttttctt tcattacttg attatttttct ttaaaatcag    4459 ctattacagg atatttttttt attttctaca ttctgttttt taattaatat gtactcactg    4519
aactgaaatt tactaaattt gttttataag gtttgtagtg ttacagaata actaaactgg    4579
gatttataaa ccagctgtga ttaacaatgt attaattatt tgaacttgaa ccagaccatt    4639
aggaaaatta tgttatttgt tccccttgta tgctcttaac ttaaagaatt ttcccacata    4699 ccgttttttga gatagtttga gatttgagga taggatgcat gtgagagact ccataaattc    4759
aacattctgt actatagctg acaactataa acaaaatgta tcttagcatt aatatcttga    4819
gccttgaaca tcatatttaa tacaggacca ttttagaaat attcagttag ttgtatattt    4879
cctaggttac aagggctaga tctaagatta ttctcatgag aaatgttgaa tttatgagaa    4939
atggattttg aggctttgaa aatgaaaatg gctagtatct caaagatgtc agtatccata    4999
catctatggt ttcatcccag gagcagacat tagctagctg acaaacagt tgtgacaata    5059 tttgtcacat aggggcctat ggtttgttgc tcaacaatat agtacttttc tcatgtgact    5119
caacactata gcacaagtat tatttccctg gattctctga aggagcatct aaaagacggg    5179
tttctgacag tgtttgctct ttaaactatg ttttctccta cccaagttg gctttgcatc    5239 tattaaataa gttcttcagc tgccttacta ggagttctac gagggcaaca tcttttctgc    5299
atttcacctt gtatttagtt tactgtgtta agatatttga tttcagattg aatgaatgta    5359
aatagaaatt aaatgcaaat ttgaatgaac ataaaa                              5395

<210> SEQ ID NO 47
<211> LENGTH: 525
<212> TYPE: PRT
<213> ORGANISM: Mus musculus

<400> SEQUENCE: 47

Met Arg Arg Arg Arg Arg Asp Gly Phe Tyr Leu Ala Pro Asp Phe
1               5                   10                  15

Arg His Arg Glu Ala Glu Asp Met Ala Gly Val Phe Asp Ile Asp Leu
            20                  25                  30

Asp Gln Pro Glu Asp Ala Gly Ser Glu Asp Leu Glu Glu Gly Gly
        35                  40                  45

Gln Leu Asn Glu Ser Met Asp His Gly Gly Val Gly Pro Tyr Glu Leu
    50                  55                  60

Gly Met Glu His Cys Glu Lys Phe Glu Ile Ser Glu Thr Ser Val Asn
65                  70                  75                  80

Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
            100                 105                 110
```

```
Gly Ala Asn Thr Gly Lys Ile Phe Ala Met Lys Val Leu Lys Lys Ala
            115                 120                 125

Met Ile Val Arg Asn Ala Lys Asp Thr Ala His Thr Lys Ala Glu Arg
130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
                165                 170                 175

Gly Gly Glu Leu Phe Met Gln Leu Glu Arg Glu Gly Ile Phe Met Glu
            180                 185                 190

Asp Thr Ala Cys Phe Tyr Leu Ala Glu Ile Ser Met Ala Leu Gly His
            195                 200                 205

Leu His Gln Lys Gly Ile Ile Tyr Arg Asp Leu Lys Pro Glu Asn Ile
    210                 215                 220

Met Leu Asn His Gln Gly His Val Lys Leu Thr Asp Phe Gly Leu Cys
225                 230                 235                 240

Lys Glu Ser Ile His Asp Gly Thr Val Thr His Thr Phe Cys Gly Thr
                245                 250                 255

Ile Glu Tyr Met Ala Pro Glu Ile Leu Met Arg Ser Gly His Asn Arg
            260                 265                 270

Ala Val Asp Trp Trp Ser Leu Gly Ala Leu Met Tyr Asp Met Leu Thr
            275                 280                 285

Gly Ala Pro Pro Phe Thr Gly Glu Asn Arg Lys Lys Thr Ile Asp Lys
            290                 295                 300

Ile Leu Lys Cys Lys Leu Asn Leu Pro Pro Tyr Leu Thr Gln Glu Ala
305                 310                 315                 320

Arg Asp Leu Leu Lys Lys Leu Leu Lys Arg Asn Ala Ala Ser Arg Leu
                325                 330                 335

Gly Ala Gly Pro Gly Asp Ala Gly Glu Val Gln Ala His Pro Phe Phe
            340                 345                 350

Arg His Ile Asn Trp Glu Glu Leu Leu Ala Arg Lys Val Glu Pro Pro
            355                 360                 365

Phe Lys Pro Leu Leu Gln Ser Glu Glu Asp Val Ser Gln Phe Asp Ser
            370                 375                 380

Lys Phe Thr Arg Gln Thr Pro Val Asp Ser Pro Asp Asp Ser Thr Leu
385                 390                 395                 400

Ser Glu Ser Ala Asn Gln Val Phe Leu Gly Phe Thr Tyr Val Ala Pro
                405                 410                 415

Ser Val Leu Glu Ser Val Lys Glu Lys Phe Ser Phe Glu Pro Lys Ile
            420                 425                 430

Arg Ser Pro Arg Arg Phe Ile Gly Ser Pro Arg Thr Pro Val Ser Pro
            435                 440                 445

Val Lys Phe Ser Pro Gly Asp Phe Trp Gly Arg Gly Ala Ser Ala Ser
    450                 455                 460

Thr Ala Asn Pro Gln Thr Pro Val Glu Tyr Pro Met Glu Thr Ser Gly
465                 470                 475                 480

Ile Glu Gln Met Asp Val Thr Val Ser Gly Glu Ala Ser Ala Pro Leu
                485                 490                 495

Pro Ile Arg Gln Pro Asn Ser Gly Pro Tyr Lys Lys Gln Ala Phe Pro
            500                 505                 510

Met Ile Ser Lys Arg Pro Glu His Leu Arg Met Asn Leu
            515                 520                 525
```

<210> SEQ ID NO 48
<211> LENGTH: 5332
<212> TYPE: DNA
<213> ORGANISM: Homo sapiens
<220> FEATURE:
<221> NAME/KEY: CDS
<222> LOCATION: (104)..(1681)

<400> SEQUENCE: 48

```
gctgaacttt aggagccagt ctaaggccta ggcgcagacg cactgagcct aagcagccgg        60
tgatggcggc agcggctgtg gtggctgcgg cgggtccggg ccc atg agg cga cga       115
                                              Met Arg Arg Arg
                                                1 agg agg cgg gac ggc ttt tac cca gcc ccg gac ttc cga gac agg gaa       163
Arg Arg Arg Asp Gly Phe Tyr Pro Ala Pro Asp Phe Arg Asp Arg Glu
  5              10                  15                  20 gct gag gac atg gca gga gtg ttt gac ata gac ctg gac cag cca gag       211
Ala Glu Asp Met Ala Gly Val Phe Asp Ile Asp Leu Asp Gln Pro Glu
             25                  30                  35 gac gcg ggc tct gag gat gag ctg gag gag ggg ggt cag tta aat gaa       259
Asp Ala Gly Ser Glu Asp Glu Leu Glu Glu Gly Gly Gln Leu Asn Glu
         40                  45                  50 agc atg gac cat ggg gga gtt gga cca tat gaa ctt ggc atg gaa cat       307
Ser Met Asp His Gly Gly Val Gly Pro Tyr Glu Leu Gly Met Glu His
     55                  60                  65 tgt gag aaa ttt gaa atc tca gaa act agt gtg aac aga ggg cca gaa       355
Cys Glu Lys Phe Glu Ile Ser Glu Thr Ser Val Asn Arg Gly Pro Glu
 70                  75                  80 aaa atc aga cca gaa tgt ttt gag cta ctt cgg gta ctt ggt aaa ggg       403
Lys Ile Arg Pro Glu Cys Phe Glu Leu Leu Arg Val Leu Gly Lys Gly
 85                  90                  95                 100 ggc tat gga aag gtt ttt caa gta cga aaa gta aca gga gca aat act       451
Gly Tyr Gly Lys Val Phe Gln Val Arg Lys Val Thr Gly Ala Asn Thr
                105                 110                 115 ggg aaa ata ttt gcc atg aag gtg ctt aaa aag gca atg ata gta aga       499
Gly Lys Ile Phe Ala Met Lys Val Leu Lys Lys Ala Met Ile Val Arg
            120                 125                 130 aat gct aaa gat aca gct cat aca aaa gca gaa cgg aat att ctg gag       547
Asn Ala Lys Asp Thr Ala His Thr Lys Ala Glu Arg Asn Ile Leu Glu
        135                 140                 145 gaa gta aag cat ccc ttc atc gtg gat tta att tat gcc ttt cag act       595
Glu Val Lys His Pro Phe Ile Val Asp Leu Ile Tyr Ala Phe Gln Thr
    150                 155                 160 ggt gga aaa ctc tac ctc atc ctt gag tat ctc agt gga gga gaa cta       643
Gly Gly Lys Leu Tyr Leu Ile Leu Glu Tyr Leu Ser Gly Gly Glu Leu
165                 170                 175                 180 ttt atg cag tta gaa aga gag gga ata ttt atg gaa gac act gcc tgc       691
Phe Met Gln Leu Glu Arg Glu Gly Ile Phe Met Glu Asp Thr Ala Cys
                185                 190                 195 ttt tac ttg gca gaa atc tcc atg gct ttg ggg cat tta cat caa aag       739
Phe Tyr Leu Ala Glu Ile Ser Met Ala Leu Gly His Leu His Gln Lys
            200                 205                 210 ggg atc atc tac aga gac ctg aag ccg gag aat atc atg ctt aat cac       787
Gly Ile Ile Tyr Arg Asp Leu Lys Pro Glu Asn Ile Met Leu Asn His
        215                 220                 225 caa ggt cat gtg aaa cta aca gac ttt gga cta tgc aaa gaa tct att       835
Gln Gly His Val Lys Leu Thr Asp Phe Gly Leu Cys Lys Glu Ser Ile
    230                 235                 240 cat gat gga aca gtc aca cac aca ttt tgt gga aca ata gaa tac atg       883
His Asp Gly Thr Val Thr His Thr Phe Cys Gly Thr Ile Glu Tyr Met
```

```
            245                 250                 255                 260
gcc cct gaa atc ttg atg aga agt ggc cac aat cgt gct gtg gat tgg          931
Ala Pro Glu Ile Leu Met Arg Ser Gly His Asn Arg Ala Val Asp Trp
                    265                 270                 275 tgg agt ttg gga gca tta atg tat gac atg ctg act gga gcc ccc cca          979
Trp Ser Leu Gly Ala Leu Met Tyr Asp Met Leu Thr Gly Ala Pro Pro
                280                 285                 290 ttc act ggg gag aat aga aag aaa aca att gac aaa atc ctc aaa tgt         1027
Phe Thr Gly Glu Asn Arg Lys Lys Thr Ile Asp Lys Ile Leu Lys Cys
            295                 300                 305 aaa ctc aat ttg cct ccc tac ctc aca caa gaa gcc aga gat ctg ctt         1075
Lys Leu Asn Leu Pro Pro Tyr Leu Thr Gln Glu Ala Arg Asp Leu Leu
        310                 315                 320 aaa aag ctg ctg aaa aga aat gct gct tct cgt ctg gga gct ggt cct         1123
Lys Lys Leu Leu Lys Arg Asn Ala Ala Ser Arg Leu Gly Ala Gly Pro
325                 330                 335                 340 ggg gac gct gga gaa gtt caa gct cat cca ttc ttt aga cac att aac         1171
Gly Asp Ala Gly Glu Val Gln Ala His Pro Phe Phe Arg His Ile Asn
                    345                 350                 355 tgg gaa gaa ctt ctg gct cga aag gtg gag ccc ccc ttt aaa cct ctg         1219
Trp Glu Glu Leu Leu Ala Arg Lys Val Glu Pro Pro Phe Lys Pro Leu
                360                 365                 370 ttg caa tct gaa gag gat gta agt cag ttt gat tcc aag ttt aca cgt         1267
Leu Gln Ser Glu Glu Asp Val Ser Gln Phe Asp Ser Lys Phe Thr Arg
            375                 380                 385 cag aca cct gtc gac agc cca gat gac tca act ctc agt gaa agt gcc         1315
Gln Thr Pro Val Asp Ser Pro Asp Asp Ser Thr Leu Ser Glu Ser Ala
        390                 395                 400 aat cag gtc ttt ctg ggt ttt aca tat gtg gct cca tct gta ctt gaa         1363
Asn Gln Val Phe Leu Gly Phe Thr Tyr Val Ala Pro Ser Val Leu Glu
405                 410                 415                 420 agt gtg aaa gaa aag ttt tcc ttt gaa cca aaa atc cga tca cct cga         1411
Ser Val Lys Glu Lys Phe Ser Phe Glu Pro Lys Ile Arg Ser Pro Arg
                    425                 430                 435 aga ttt att ggc agc cca cga aca cct gtc agc cca gtc aaa ttt tct         1459
Arg Phe Ile Gly Ser Pro Arg Thr Pro Val Ser Pro Val Lys Phe Ser
                440                 445                 450 cct ggg gat ttc tgg gga aga ggt gct tcg gcc agc aca gca aat cct         1507
Pro Gly Asp Phe Trp Gly Arg Gly Ala Ser Ala Ser Thr Ala Asn Pro
            455                 460                 465 cag aca cct gtg gaa tac cca atg gaa aca agt ggc ata gag cag atg         1555
Gln Thr Pro Val Glu Tyr Pro Met Glu Thr Ser Gly Ile Glu Gln Met
        470                 475                 480 gat gtg aca atg agt ggg gaa gca tcg gca cca ctt cca ata cga cag         1603
Asp Val Thr Met Ser Gly Glu Ala Ser Ala Pro Leu Pro Ile Arg Gln
485                 490                 495                 500 ccg aac tct ggg cca tac aaa aaa caa gct ttt ccc atg atc tcc aaa         1651
Pro Asn Ser Gly Pro Tyr Lys Lys Gln Ala Phe Pro Met Ile Ser Lys
                    505                 510                 515 cgg cca gag cac ctg cgt atg aat cta tga cagagcaatg cttttaatga          1701
Arg Pro Glu His Leu Arg Met Asn Leu
                520                 525 atttaaggca aaaaggtgg agagggagat gtgtgagcat cctgcaaggt gaaacgactc        1761
aaaatgacag tttcagagag tcaatgtcat tacatagaac acttcagaca caggaaaaat      1821
aaacgtggat tttaaaaaat caatcaatgg tgcaaaaaaa aacttaaagc aaaatagtat      1881
tgctgaactc ttaggcacat caattaattg attcctcgcg acatcttctc aaccttatca     1941
aggattttca tgttgatgac tcgaaactga cagtattaag ggtaggatgt tgcttctgaa     2001
```

```
tcactgttga gttctgattg tgttgaagaa gggttatcct ttcattaggc aaagtacaaa   2061
attgcctata atacttgcaa ctaaggacaa attagcatgc aagcttggtc aaacttttc    2121 cagcaaaatg gaagcaaaga caaagaaac ttaccaattg atgttttacg tgcaaacaac    2181
ctgaatcttt tttttatata aatatatatt tttcaaatag atttttgatt cagctcatta   2241
tgaaaaacat cccaaacttt aaaatgcgaa attattggtt ggtgtgaaga aagccagaca   2301
acttctgttt cttctcttgg tgaaataata aaatgcaaat gaatcattgt taaccacagc   2361
tgtggctcgt ttgagggatt ggggtggacc tggggtttat tttcagtaac ccagctgcaa   2421
tacctgtctg taatatgaga aaaaaaaaat gaatctattt aatcatttct acttgcagta   2481
ctgctatgtg ctaagcttaa ctggaagcct tggaatgggc ataagttgta tgtcctacat   2541
ttcatcattg tcccgggcct gcattgcact ggaaaaaaaa atcgccacct gttcttacac   2601
cagtatttgg ttcaagacac caaatgtctt cagcccatgg ctgaagaaca acagaagaga   2661
gtcaggataa aaaatacata ctgtggtcgg caaggtgagg gagataggga tatccagggg   2721
aagagggtgt tgctgtggcc cactctctgt ctaatctctt tacagcaaat tggtaagatt   2781
ttcagtttta cttcttctcta ctgtttctgc tgtctacctt ccttatattt ttttcctcaa   2841
cagttttaaa aagaaaaaaa ggtctatttt tttttctcct atacttgggc tacattttt    2901 gattgtaaaa atatttgatg cctttgat gaatgtcttc cacagtaaag aaacttagt     2961 ggcttaattt aggaaacatg ttaacaggac actatgtttt tgaaattgta acaaaatcta   3021
cataaatgat ttacaggtta aaagaataaa aataaaggta actttacctt tcttaaatat   3081
ttcctgcctt aaagagagca tttccatgac tttagctggt gaagggttt aatatctgca    3141 gagctttata aaaatatatt tcagtgcata ctggtataat agatgatcat gcagttgcag   3201
ttgagttgta tcacctttt tgtttgtctt ttataatgtc ttcagtctga gtgtgcaaag    3261
tcaatttgta atattttgca accctaggat tttttttaaat agatgctgct tgctatgttt   3321
tcaaaccttt ttgagccata ggatccaagc cataaaattc tttatgcatg ttgaattcag   3381
tcagaaaaga gcaaggcttt gctttttgaa attgcaactc aaatgagatg ggatgaaatc   3441
ctatgacagt aagcaaaaac agaaccatga aaaatgattg gacatacacc ttttcaattg   3501
tggcaataat tgaaagaatc gataaaagtt catctttgga cagaaagcct ttaaaaaaaa   3561
aatcactccc tcttccccct cctcccttat tgcagcagcc tactgagaac tttgactgtt   3621
gctggtaaat tagaagctac aataataatt aagggcagaa attatactta aaaagtgcag   3681
atccttgttc tttgacaatt tgtgatgtct gaaaaaacag aacccgaaaa gctatggtga   3741
tatgtacagg cattatttca gactgtaaat ggcttgtgat actcttgata cttgttttca   3801
aatatgttta ctaactgtag tgttgactgc ctgaccaaat tccagtgaaa cttatacacc   3861
aaaatattct tcctaggtcc tatttgctag taacatgagc actgtgattg gctggctata   3921
accaccccag ttaaccatt ttcataatta gtagtgccag caatagtggc aaacactgca    3981
acttttctgc ataaaaagca ttaattgcac agctaccatc cacacaaata catagttttt   4041
ctgacttcac atttattaag tgaaatttat ttcccatgct gtggaaagtt tattgagaac   4101
ttgtttcata aatggatatc cctactatga ctgtgaaaac atgtcaagtg tcacattagt   4161
gtcacagaca gaaagcacac acctatgcaa tatggcttat ctatatttat ttgtaaaaat   4221
ccaagcatag tttaaaatat gatgtcgata ttactagtct tgagtttcta agagggttct   4281
ttatgttata ccaggtaagt gtataaaaga gattaagtgc ttttttttca tcacttgatt   4341
```

```
attttctttta aaatcagcta ttacaggata ttttttttatt ttatacatgc tgtttttttaa    4401 ttaaaatata atcactgaag tttactaatt tgatttttata aggtttgtag cattacagaa    4461
taactaaact gggatttata aaccagctgt gattaacaat gtaaagtatt aattattgaa    4521
ctttgaacca gattttttagg aaaattatgt tcttttttccc cctttatggt cttaactaat    4581
ttgaatcctt caagaaggat ttttccatac tattttttaa gatagaagat aatttgtggg    4641
caggggtgga ggatgcatgt atgatactcc ataaattcaa cattctttac tataggtaat    4701
gaatgattat aaacaagatg catcttagat agtattaata tactgagcct tggattatat    4761
atttaatata ggacctattt tgaatattca gttaatcata tggttcctag cttacaaggg    4821
ctagatctaa gattattccc atgagaaatg ttgaatttat gaagaataga ttttaaggct    4881
ttgaaaatgg ttaatttctc aaaaacatca atgtccaaac atctaccttt tttcatagga    4941
gtagacacta gcaagctgga caaactatca caaaagtatt tgtcacacat aacctgtggt    5001
ctgttgctga ttaatacagt acttttttctt gtgtgattct taacattata gcacaagtat    5061
tatctcagtg gattatccgg aataacatct gaaagatggg ttcatctatg tttgtgtttg    5121
ctctttaaac tattgtttct cctatcccaa gttcgctttg catctatcag taaataaaat    5181
tcttcagctg ccttattagg agtgctatga gggtaacacc tgttctgctt ttcatcttgt    5241
atttagttga ctgtattatt tgatttcgga ttgaatgaat gtaaatagaa attaaatgca    5301
aatttgaatg aacataaaaa aaaaaaaaaa a                                     5332
```

<210> SEQ ID NO 49
<211> LENGTH: 525
<212> TYPE: PRT
<213> ORGANISM: Homo sapiens

<400> SEQUENCE: 49

```
Met Arg Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
            20                  25                  30

Asp Gln Pro Glu Asp Ala Gly Ser Glu Asp Glu Leu Glu Glu Gly Gly
        35                  40                  45

Gln Leu Asn Glu Ser Met Asp His Gly Gly Val Gly Pro Tyr Glu Leu
    50                  55                  60

Gly Met Glu His Cys Glu Lys Phe Glu Ile Ser Glu Thr Ser Val Asn
65                  70                  75                  80

Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
            100                 105                 110

Gly Ala Asn Thr Gly Lys Ile Phe Ala Met Lys Val Leu Lys Lys Ala
        115                 120                 125

Met Ile Val Arg Asn Ala Lys Asp Thr Ala His Thr Lys Ala Glu Arg
    130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
                165                 170                 175

Gly Gly Glu Leu Phe Met Gln Leu Glu Arg Glu Gly Ile Phe Met Glu
            180                 185                 190

Asp Thr Ala Cys Phe Tyr Leu Ala Glu Ile Ser Met Ala Leu Gly His
```

-continued

```
            195                 200                 205
Leu His Gln Lys Gly Ile Ile Tyr Arg Asp Leu Lys Pro Glu Asn Ile
        210                 215                 220

Met Leu Asn His Gln Gly His Val Lys Leu Thr Asp Phe Gly Leu Cys
225                 230                 235                 240

Lys Glu Ser Ile His Asp Gly Thr Val Thr His Thr Phe Cys Gly Thr
                    245                 250                 255

Ile Glu Tyr Met Ala Pro Glu Ile Leu Met Arg Ser Gly His Asn Arg
                260                 265                 270

Ala Val Asp Trp Trp Ser Leu Gly Ala Leu Met Tyr Asp Met Leu Thr
                275                 280                 285

Gly Ala Pro Pro Phe Thr Gly Glu Asn Arg Lys Lys Thr Ile Asp Lys
        290                 295                 300

Ile Leu Lys Cys Lys Leu Asn Leu Pro Pro Tyr Leu Thr Gln Glu Ala
305                 310                 315                 320

Arg Asp Leu Leu Lys Lys Leu Leu Lys Arg Asn Ala Ala Ser Arg Leu
                325                 330                 335

Gly Ala Gly Pro Gly Asp Ala Gly Glu Val Gln Ala His Pro Phe Phe
                340                 345                 350

Arg His Ile Asn Trp Glu Glu Leu Leu Ala Arg Lys Val Glu Pro Pro
                355                 360                 365

Phe Lys Pro Leu Leu Gln Ser Glu Glu Asp Val Ser Gln Phe Asp Ser
        370                 375                 380

Lys Phe Thr Arg Gln Thr Pro Val Asp Ser Pro Asp Asp Ser Thr Leu
385                 390                 395                 400

Ser Glu Ser Ala Asn Gln Val Phe Leu Gly Phe Thr Tyr Val Ala Pro
                405                 410                 415

Ser Val Leu Glu Ser Val Lys Glu Lys Phe Ser Phe Glu Pro Lys Ile
                420                 425                 430

Arg Ser Pro Arg Arg Phe Ile Gly Ser Pro Arg Thr Pro Val Ser Pro
        435                 440                 445

Val Lys Phe Ser Pro Gly Asp Phe Trp Gly Arg Gly Ala Ser Ala Ser
        450                 455                 460

Thr Ala Asn Pro Gln Thr Pro Val Glu Tyr Pro Met Glu Thr Ser Gly
465                 470                 475                 480

Ile Glu Gln Met Asp Val Thr Met Ser Gly Glu Ala Ser Ala Pro Leu
                485                 490                 495

Pro Ile Arg Gln Pro Asn Ser Gly Pro Tyr Lys Lys Gln Ala Phe Pro
                500                 505                 510

Met Ile Ser Lys Arg Pro Glu His Leu Arg Met Asn Leu
        515                 520                 525
```

EFFICIENT METHOD FOR ESTABLISHING INDUCED PLURIPOTENT STEM CELLS

CROSS-REFERENCE TO RELATED APPLICATIONS

This patent application is the U.S. national phase of International Patent Application No. PCT/JP2011/077992, filed Dec. 2, 2011, which claims the benefit of U.S. Provisional Patent Application No. 61/419,320, filed on Dec. 3, 2010, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 242,371 bytes ASCII (Text) file named "713609SequenceListing.txt," created Jun. 3, 2013.

TECHNICAL FIELD

The present invention relates to a method of improving the efficiency of establishment of induced pluripotent stem (hereinafter sometimes referred to as iPS) cells and a reagent therefor. More specifically, the present invention relates to a method of improving the iPS cell establishment efficiency by using a member of the Ras family, and an agent for improving the iPS cell establishment efficiency, which comprises a member of the Ras family as an active ingredient.

BACKGROUND ART

In recent years, mouse and human iPS cells have been established one after another. Takahashi and Yamanaka (non-patent document 1) induced iPS cells by transferring the Oct3/4, Sox2, Klf4 and c-Myc genes into fibroblasts from a reporter mouse wherein the neomycin resistance gene is knocked-in into the Fbx15 locus, and forcing the cells to express the genes. Okita et al. (non-patent document 2) succeeded in establishing iPS cells (Nanog iPS cells) that show almost the same gene expression and epigenetic modification profiles as those of embryonic stem (ES) cells by creating a transgenic mouse having the green fluorescent protein (GFP) and puromycin-resistance genes integrated into the locus of Nanog, whose expression is more localized in pluripotent cells than the expression of Fbx15, forcing fibroblasts from the mouse to express the above-mentioned four genes, and selecting puromycin-resistant and GFP-positive cells. Thereafter, it was revealed that iPS cells could also be produced with three of the factors other than the c-Myc gene (non-patent document 3).

Furthermore, Takahashi et al. (non-patent document 4) succeeded in establishing iPS cells by transferring into human dermal fibroblasts the same four genes as those used in the mouse. On the other hand, Yu et al. (non-patent document 5) produced human iPS cells using Nanog and Lin28 in place of Klf4 and c-Myc. Hence, it has been demonstrated that iPS cells comparable to ES cells in terms of pluripotency can be produced in both humans and mice, by transferring defined factors into somatic cells.

However, the iPS cell establishment efficiency is still low and, especially, a problem of extremely low iPS cell establishment efficiency occurs when human iPS cell is produced by introducing 3 factors (Oct3/4, Sox2 and Klf4) excluding c-Myc, which is feared to cause tumorigenesis in tissues or individuals differentiated from iPS cells, into somatic cells.

Ras, which is a small GTPase, regulates growth and differentiation in many cells. Ras is generally present as an inactivated form bound with GDP. When stimulated by a growth factor and the like, it dissociates GDP, binds to GTP to turn into an activated form, and transmits signal to the downstream via a target factor. As Ras target factor, Raf, phosphatidylinositol 3-kinase (PI3 kinase), Ral Guanine nucleotide Exchanging Factor (RalGEF) and the like are known. A constitutively activating point mutation of Ras has been reported in various human cancer cells, and therefore, functional collapse of Ras protein caused by abnormality in the downstream signaling by these target factors is assumed to be one of the important steps of cell canceration.

Takahashi et al. (non-patent document 6) identified a gene specifically expressed in embryonic stem cells (ES cells) and having a homology with other Ras genes and named it ERas. Although ERas shows only about 40% homology with other Ras as a whole, it highly conserves 5 guanine nucleotide-binding domains (G1-G5) essential for the function of Ras, and also has C-terminal Caax motif (C: cysteine, a: aliphatic amino acid, x: any amino acid) necessary for membrane localization.

However, the relationship between Ras family and reprogramming of somatic cell has not been sufficiently elucidated.

DOCUMENT LIST

Non-Patent Documents non-patent document 1: Takahashi, K. and Yamanaka, S., Cell, 126: 663-676 (2006)
non-patent document 2: Okita, K. et al., Nature, 448: 313-317 (2007)
non-patent document 3: Nakagawa, M. et al., Nat. Biotechnol., 26: 101-106 (2008)
non-patent document 4: Takahashi, K. et al., Cell, 131: 861-872 (2007)
non-patent document 5: Yu, J. et al., Science, 318: 1917-1920 (2007)
non-patent document 6: Takahashi, K. et al., Nature, 423: 541-545 (2003)

SUMMARY OF THE INVENTION

Problems to be Solved by the Invention

It is an object of the present invention to provide a means of improving the iPS cell establishment efficiency, and a method of efficiently producing iPS cells using the means.

Means of Solving the Problems

The present inventors have conducted intensive studies in an attempt to achieve the above-mentioned object, and clarified that the iPS cell establishment efficiency can be remarkably enhanced by increasing the level of the Ras family members in activated form, or target factors or related factors thereof (PI3 kinase, RalGEF, Raf, AKT family members, Rheb, TCL1 and activated molecule of S6K) in activated form during the nuclear reprogramming step of somatic cell. Moreover, they have clarified from experiments using various activated mutants that activation of signal transduction pathway via PI3 kinase (PI3 kinase pathway), signal transduction pathway via RalGEF (Ral pathway) and AKT pathway by Ras protein greatly contributes to the improvement of iPS cell establishment efficiency, which resulted in the completion of the present invention.

Accordingly, the present invention provides:

[1] A method of improving the efficiency of establishment of induced pluripotent stem cell, comprising the step of increasing the level of activated form of one or more proteins selected from the group consisting of Ras family members, PI3 kinase, RalGEF, Raf, AKT family members, Rheb, TCL1 and S6K in a nuclear reprogramming step of somatic cell.

[2] The method according to [1] above, comprising contacting one or more factors selected from the group consisting of Ras family members, PI3 kinase, RalGEF, Raf, AKT family members, Rheb, TCL1 and S6K, and nucleic acids that encode the same with a somatic cell.

[3] The method according to [2] above, wherein the Ras family members, PI3 kinase, RalGEF, Raf, AKT family members and S6K are constitutively active forms.

[4] The method according to [2] or [3] above, wherein the Ras family members are selected from the group consisting of ERas, HRas, NRas and KRas.

[5] The method according to [3] or [4] above, wherein the Ras family members constitutively activate one or more signal transduction pathways selected from PI3 kinase pathway, Ral pathway and MAP kinase pathway.

[6] The method according to [3] or [4] above, wherein the Ras family members constitutively activate PI3 kinase pathway and/or Ral pathway.

[7] The method according to [3] above, wherein the PI3 kinase constitutively activates signal transduction pathway of AKT pathway.

[8] The method according to [2] or [3] above, wherein the AKT family members are selected from the group consisting of AKT1, AKT2 and AKT3.

[9] The method according to [3] or [8] above, wherein the AKT family members constitutively activate signal transduction pathway of mTOR pathway.

[10] The method according to [2] above, further comprising contacting one or more factors selected from the group consisting of p53 inhibitor, GLIS family members, and nucleic acids that encode the same them with the somatic cell.

[11] An agent for improving the efficiency of establishment of induced pluripotent stem cell, comprising a factor selected from the group consisting of Ras family members, PI3 kinase, RalGEF, Raf, AKT family members, Rheb, TCL1 and S6K, and nucleic acids that encode the same.

[12] The agent according to [11] above, wherein the Ras family members, PI3 kinase, RalGEF, Raf, AKT family members and S6K are constitutively active forms.

[13] The agent according to [11] or [12] above, wherein the Ras family members are selected from the group consisting of ERas, HRas, NRas and KRas.

[14] The agent according to [12] or [13] above, wherein the Ras family members constitutively activate one or more signal transduction pathways selected from PI3 kinase pathway, Ral pathway and MAP kinase pathway.

[15] The agent according to [12] or [13] above, wherein the Ras family members constitutively activate PI3 kinase pathway and/or Ral pathway.

[16] The agent according to [12] above, wherein the PI3 kinase constitutively activates signal transduction pathway of AKT pathway.

[17] The agent according to [11] or [12] above, wherein the AKT family members are selected from the group consisting of AKT1, AKT2 and AKT3.

[18] The agent according to [12] or [17] above, wherein the AKT members constitutively activate signal transduction pathway of mTOR pathway.

[19] The agent according to [11] above, further comprising one or more factors selected from the group consisting of p53 inhibitor, GLIS family members, and nucleic acids that encode the same.

[20] A method of producing induced pluripotent stem cells, comprising contacting a somatic cell with nuclear reprogramming substance(s) and one or more factors selected from the group consisting of Ras family members, PI3 kinase, RalGEF, Raf, AKT family members, Rheb, TCL1 and S6K, and nucleic acids that encode the same.

[21] The method according to [20] above, wherein the Ras family members, PI3 kinase, RalGEF, Raf, AKT family members and S6K are constitutively active forms.

[22] The method according to [20] or [21] above, wherein the Ras family members are selected from the group consisting of ERas, HRas, NRas and KRas.

[23] The method according to [21] or [22] above, wherein the Ras family members constitutively activate one or more signal transduction pathways selected from PI3 kinase pathway, Ral pathway and MAP kinase pathway.

[24] The method according to [21] or [22] above, wherein the Ras family members constitutively activate PI3 kinase pathway and/or Ral pathway.

[25] The method according to [21] above, wherein the PI3 kinase constitutively activates signal transduction pathway of AKT pathway.

[26] The method according to [20] or [21] above, wherein the AKT family members are selected from the group consisting of AKT1, AKT2 and AKT3.

[27] The method according to [21] or [26] above, wherein the AKT family members constitutively activate signal transduction pathway of mTOR pathway.

[28] The method according to [20] above, further comprising contacting one or more factors selected from the group consisting of p53 inhibitor, GLIS family members, and nucleic acids that encode the same with the somatic cell.

[29] The method according to [20] above, wherein the nuclear reprogramming substance(s) is(are) selected from the group consisting of Oct family members, Sox family members, Klf4 family members, Myc family members, Lin family members and Nanog, as well as nucleic acids that encode the same.

[30] The method according to [20] above, wherein the nuclear reprogramming substances are Oct3/4, Klf4 and Sox2, or nucleic acids that encode the same.

[31] The method according to [20] above, wherein the nuclear reprogramming substances are Oct3/4, Klf4, Sox2, as well as c-Myc or L-Myc and/or Nanog and/or Lin28 or Lin28B, or nucleic acids that encode the same.

[32] An agent for inducing an induced pluripotent stem cell, comprising a factor selected from the group consisting of Ras family members, PI3 kinase, RalGEF, Raf, AKT family members, Rheb, TCL1 and S6K, and nucleic acids that encode the same, as well as nuclear reprogramming substance(s).

[33] The agent according to [32] above, Ras family members, PI3 kinase, RalGEF, Raf, AKT family members and S6K are constitutively active forms.

[34] The agent according to [32] or [33] above, wherein the Ras family members are selected from the group consisting of ERas, HRas, NRas and KRas.

[35] The agent according to [33] or [34] above, wherein the Ras family members constitutively activate one or more signal transduction pathways selected from PI3 kinase pathway, Ral pathway and MAP kinase pathway.

[36] The agent according to [33] or [34] above, wherein the Ras family members constitutively activate PI3 kinase pathway and/or Ral pathway.

[37] The agent according to [32] above, wherein the nuclear reprogramming substance(s) is(are) selected from the group consisting of Oct family members, Sox family members, Klf4 family members, Myc family members, members of the Lin family and Nanog, and nucleic acids that encode the same.

[38] The agent according to [33] above, wherein the PI3 kinase constitutively activates signal transduction pathway of AKT pathway.

[39] The agent according to [32] or [33] above, wherein the AKT family members are selected from the group consisting of AKT1, AKT2 and AKT3.

[40] The agent according to [33] or [39] above, wherein the AKT family members constitutively activate signal transduction pathway of mTOR pathway.

[41] The agent according to [32] above, further comprising one or more factors selected from the group consisting of p53 inhibitor, GLIS family members, and nucleic acids that encode the same.

[42] The agent according to [32] above, wherein the nuclear reprogramming substances are Oct3/4, Klf4 and Sox2, or nucleic acids that encode the same.

[43] The agent according to [32] above, wherein the nuclear reprogramming substance(s) are Oct3/4, Klf4, Sox2 as well as c-Myc or L-Myc and/or Nanog and/or Lin28 or Lin28B, or nucleic acids that encode the same.

[44] An induced pluripotent stem cell, comprising an exogeneous nucleic acid encoding Ras family members, PI3 kinase, RalGEF, Raf, AKT family members, Rheb, TCL1 or S6K.

[45] The cell according to [44] above, wherein the aforementioned exogenous nucleic acid is integrated in the genome.

[46] A method of producing a somatic cell, comprising the steps of:
(1) producing an induced pluripotent stem cell by the method according to any of [20] to [31] above, and
(2) performing a differentiation induction treatment on the iPS cell obtained through the step (1) to cause the induced pluripotent stem cell to differentiate into a somatic cell.

[47] A use of one or more factors selected from the group consisting of Ras family members, PI3 kinase, RalGEF, Raf, AKT family members, Rheb, TCL1 and S6K, and nucleic acids that encode the same for improving the iPS cell establishment efficiency.

[48] A use of one or more factors selected from the group consisting of Ras family members, PI3 kinase, RalGEF, Raf, AKT family members, Rheb, TCL1 and S6K, and nucleic acids that encode the same, for producing an iPS cell, wherein the factor(s) is(are) contacted with a somatic cell along with nuclear reprogramming substance(s).

[49] A use of the induced pluripotent stem cell according to [44] or [45] above in producing a somatic cell.

[50] The induced pluripotent stem cell according to [44] or [45] above, as a cell source in producing a somatic cell.

Effect of the Invention

The iPS cell establishment efficiency can be remarkably enhanced by increasing the level of activated molecules of the Ras family members, target factors thereof (PI3 kinase, RalGEF or Raf), or related factors thereof (AKT family members, Rheb, TCL1 or S6K) during nuclear reprogramming, which is particularly useful in the induction of iPS cells by means of 3 factors except c-Myc that has conventionally showed low establishment efficiency.

BRIEF DESCRIPTION OF THE DRAWINGS

FIG. 8 shows graphs presenting the results of Example 8.

FIG. 11 shows a graph and photographs presenting the results of Example 11.

FIG. 12 shows a graph presenting the results of Example 12.

DESCRIPTION OF EMBODIMENTS

Figure 1:
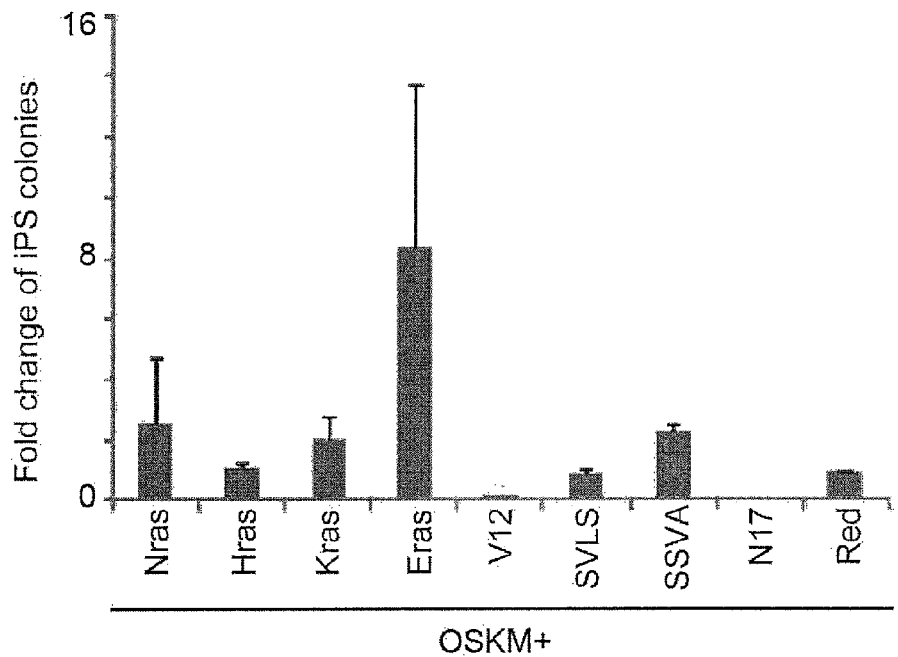
FIG. 1 shows a graph presenting the results of Example 1, wherein the vertical axis shows fold change of the number of iPS colonies when the number of colonies obtained by 4 transgenes of Oct3/4, Sox2, Klf4 and c-Myc is 1 (Red in the Figure), and the horizontal axis shows combinations of Oct3/4, Sox2, Klf4 and c-Myc genes and respective genes shown in the horizontal axis.

The present invention provides a method of improving efficiency of iPS cell establishment, comprising increasing the intracellular level of a Ras protein in activated form, an activated form of the target factor thereof, an activated form of a signaling factor downstream of Ras target factor or an activator of the signaling, in a nuclear reprogramming step of somatic cell. While the means of increasing the intracellular level of a Ras protein in activated form, an activated form of target factor thereof, an activated form of a signaling factor downstream of Ras target factor or an activator of the signal is not particularly limited, for example, a method including contacting a Ras family member protein, a target factor thereof (PI3 kinase, RalGEF or Raf), a signaling factor downstream of Ras target factor or an activator of the signaling (AKT family member, Rheb, TCL1 or S6K), or nucleic acids encoding them, or a substance that promotes conversion reaction of Ras protein into an activated form or a substance that inhibits conversion reaction of Ras protein into an inactivated form, with a somatic cell, and the like can be mentioned.

While nuclear reprogramming of a somatic cell is achieved by transferring a nuclear reprogramming substance to the somatic cell, the present invention also provides a method of producing an iPS cell by contacting the above-mentioned substance with a nuclear reprogramming substance to a somatic cell. In the present specification, cases where iPS cells cannot be established by using a nuclear reprogramming substance alone, but can be established by increasing the level of a Ras protein in activated form and the like, are also deemed as corresponding to "an improvement of establishment efficiency."

(a) Sources of Somatic Cells

In the present invention, any cells other than germ cells of mammalian origin (e.g., humans, mice, monkeys, bovines, pigs, rats, dogs etc.) can be used as starting material for the production of iPS cells. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., bacillary cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells (tissue progenitor cells) thereof and the like. There is no limitation on the degree of cell differentiation, the age of an animal from which cells are collected and the like; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as neural stem cells, hematopoietic stem cells, mesenchymal stem cells, and dental pulp stem cells.

The choice of mammal individual as a source of somatic cells is not particularly limited; however, when the iPS cells obtained are to be used for regenerative medicine in humans, it is particularly preferable, from the viewpoint of prevention of graft rejection, to collect the somatic cells from a patient or another person with the same or substantially the same HLA gene type as that of the patient. "Substantially the same HLA type" as used herein means that the HLA gene type of donor matches with that of patient to the extent that the transplanted cells, which have been obtained by inducing differentiation of iPS cells derived from the donor's somatic cells, can be engrafted when they are transplanted to the patient with use of immunosuppressant and the like. For example, it includes an HLA gene type wherein major HLAs (e.g., the three major loci of HLA-A, HLA-B and HLA-DR, the four loci further including HLA-C) are completely identical (hereinafter the same meaning shall apply) and the like. When the iPS cells obtained are not to be administered (transplanted) to a human, but used as, for example, a source of cells for screening for evaluating a patient's drug susceptibility or adverse reactions, it is likewise desired to collect the somatic cells from the patient or another person with the same genetic polymorphism correlating with the drug susceptibility or adverse reactions.

Somatic cells isolated from a mammal can be pre-cultured using a medium known per se suitable for their cultivation according to the choice of cells before being subjected to the nuclear reprogramming step. Examples of such media include, but are not limited to, minimal essential medium (MEM) containing about 5 to 20% fetal bovine serum (FCS), Dulbecco's modified Eagle medium (DMEM), RPMI1640 medium, 199 medium, F12 medium, and the like. When a transfer reagent such as cationic liposome, for example, is used in bringing the somatic cell into contact with nuclear reprogramming substances and a substance that increases the level of a Ras protein in activated form (and another iPS cell establishment efficiency improver if required), it is sometimes preferable that the medium have been replaced with a serum-free medium so as to prevent the transfer efficiency from decreasing.

(b) Substance that Increases Level of Ras Protein, Activated Molecule of Target Factor Thereof, Signaling Factor Downstream of Ras Target Factor or Activator of the Signaling In the present specification, the "substance that increases the level of Ras protein in activated form" may be any substance as long as it can increase the level of protein present as an activated form (GTP-bound form) of one or more proteins belonging to Ras family. That is, Ras protein per se or a nucleic acid per se encoding same, as well as a substance that eventually increases the level of Ras protein in an activated form by promoting a reaction to convert Ras protein from an inactivated form (GDP-bound form) to an activated form (GDP-GTP exchange reaction), or inhibiting a reaction to convert Ras protein from an activated form to an inactivated form (GTP hydrolysis), are included in the "substance that increases the level of Ras protein in activated form" in the present specification.

In the present specification, the "substance that increases level of activated form of Ras protein target factor" may be any substance as long as it can increase the intracellular level of an activated form of one or more factors, preferably 1 or 2 factors, of the three target factors of Ras protein, PI3 kinase, RalGEF and Raf, more preferably PI3 kinase and/or RalGEF. That is, PI3 kinase, RalGEF or Raf per se or a nucleic acid per se encoding the same, as well as a localization factor that recruits such target factors in the cell into the plasma membrane such as Ras protein in activated form, are included in the "substance that increases level of activated form of Ras protein target factor" in the present specification.

In the present specification, the "substance that increases level of signaling factor downstream of Ras target factor or activator of the signaling" may be any substance as long as it can increase the intracellular level of a signaling factor downstream of Ras protein target factor or an activator of the signaling (i.e., AKT family members, Rheb, TCL1 or S6K, preferably an activated form of AKT family members, an activated form of Rheb, TCL1 or S6K). That is, AKT family members, Rheb, TCL1 or S6K per se or a nucleic acid per se encoding the same, as well as a localization factor that recruits intracellular AKT family members into the plasma membrane such as PI3 kinase in activated form, are included in the "substance that increases level of Ras protein-related factors in activated form" in the present specification.

In the following, substances that increase the level of activated molecule of Ras protein, target factor thereof or a signaling factor downstream of Ras target factor, as well as an activator of the signalin, are sometimes collectively referred to as "the establishment efficiency improving factor of the present invention".

(b1) Ras Family Members

The "Ras family members" in the present specification means a protein from the Ras subfamily proteins characterized by homology of the primary structure with HRas, KRas, NRas identified as proto-oncogenes, which protein targets one or more molecules selected from Raf, PI3 kinase and RalGEF, preferably PI3 kinase and/or RalGEF, and can activate signal transduction pathway at the downstream of the above-mentioned target factors (i.e., Raf/MAP kinase pathway (MAP kinase pathway), PI3 kinase pathway, Ral pathway), by the action of activated form of the Ras protein. Preferable examples of the Ras family members include, but are not limited to, HRas, KRas; NRas, ERas and the like.

Preferable examples of the HRas protein include mouse HRas consisting of the amino acid sequence shown by SEQ ID NO:2 (RefSeq Accession No. NP_032310), human HRas consisting of the amino acid sequence shown by SEQ ID NO:4 (RefSeq Accession No. NP_001123914), orthologs thereof in other mammals, natural allelic variants and polymorphic variants thereof, splicing variants thereof, natural and artificial activated mutants thereof and the like. While HRas homologous to the animal species of the somatic cell to be the introduction target is desirably used, heterologous HRas can also be used.

Preferable examples of the KRas protein include mouse KRas consisting of the amino acid sequence shown by SEQ ID NO:6 (RefSeq Accession No. NP_067259), human KRas consisting of the amino acid sequence shown by SEQ ID NO:8 (RefSeq Accession No. NP_203524), orthologs thereof in other mammals, natural allelic variants and polymorphic variants thereof, splicing variants, natural and artificial activated mutants and the like. While KRas homologous to the animal species of the somatic cell to be the introduction target is desirably used, heterologous KRas can also be used.

Preferable examples of the NRas protein include mouse NRas consisting of the amino acid sequence shown by SEQ ID NO:10 (RefSeq Accession No. NP_035067), human NRas consisting of the amino acid sequence shown by SEQ ID NO:12 (RefSeq Accession No. NP_002515), orthologs thereof in other mammals, natural allelic variants and polymorphic variants thereof, splicing variants, natural and artificial activated mutants and the like. While NRas homologous to the animal species of the somatic cell to be the introduction target is desirably used, heterologous NRas can also be used.

Preferable examples of the ERas protein include mouse ERas consisting of the amino acid sequence shown by SEQ ID NO:14 (RefSeq Accession No. NP_853526), human ERas consisting of the amino acid sequence shown by SEQ ID NO:16 (RefSeq Accession No. NP_853510), orthologs thereof in other mammals, natural allelic variants and polymorphic variants thereof, splicing variants thereof, and the like. While ERas homologous to the animal species of the somatic cell to be the introduction target is desirably used, heterologous ERas can also be used.

The homology of the amino acid sequences of Ras protein can be calculated using the blastp program of homology calculation algorithm NCBI BLAST (National Center for Biotechnology Information Basic Local Alignment Search Tool) and under the following conditions (expect threshold-10; accept gap; matrix=BLOSUM62; filtering=OFF). Under the above-mentioned conditions, human HRas and mouse HRas show 100% amino acid identity, human KRas and mouse KRas show about 89% amino acid identity, and human NRas and mouse NRas show about 99% amino acid identity. The region of 164 amino acids from the N-terminus of Ras protein is extremely highly conserved and, in this region, human KRas and mouse KRas show about 98% amino acid identity, and human NRas and mouse NRas show 100% amino acid identity. In this region, moreover, the amino acid identity of human HRas and human KRas is about 95%, and the amino acid identity of human HRas and human NRas is about 92%. In said region, 5 domains (G1-G5) relating to the binding with guanine nucleotide, and the effector domain relating to the binding with target factor are particularly well conserved. Furthermore, of the C-terminal sequences rich in diversity, 4 amino acid residues at the C-terminal are called Caax motif (C: cysteine, a: aliphatic amino acid, x: any amino acid; SEQ ID NO:17) and highly conserved. They are subject to post-translational modification, whereby farnesyl group is added to the cysteine residue, and successive cleavage of terminal 3 amino acids, and methyl esterification of newly exposed C-terminal cysteine. Ras protein is strongly bonded to the inner surface of plasma membrane by such lipid modification.

Many of the Ras proteins such as HRas, KRas, NRas and the like are generally present as a GDP-bound inactivated form, and converted to a GTP-bound activated form on receipt of a signal from the upstream. Constitutively active Ras mutant has been isolated from various carcinomas, and a number of amino acid substitutions contributing to constitutive activation have been reported. The level of Ras protein in activated form can be efficiently increased by introducing a constitutively active mutant of such Ras protein into a somatic cell. For example, a mutant wherein 12th glycine of H-, K- and N-Ras is substituted by valine is a constitutively active mutant that activates all 3 signal transduction pathways (PI3 kinase pathway, Ral pathway, MAP kinase pathway) at the downstream of Ras. A double mutant wherein 35th threonine is substituted by serine, a double mutant wherein 37th glutamic acid is substituted by glycine and a double mutant wherein 40th tyrosine is substituted by cysteine, each in addition to the above-mentioned mutation, are constitutively active mutants that selectively activate MAP kinase pathway, Ral pathway and PI3 kinase pathway, respectively.

While human and mouse ERas have about 40% homology with HRas over entire protein, G1-G5 and effector domain essential for the function of Ras, and Caax motif necessary for membrane localization are conserved. When even only one of 12th glycine of H-, K- and N-Ras, 59th alanine and 63rd glutamic acid is substituted by other amino acid, a constitutively active form is produced. It is known that in human Eras, 2 of the 3 amino acids are different from other Ras, and in mouse Eras, all the 3 amino acids different from other Ras, and PI3 kinase pathway from the 3 signal transduction pathways at the downstream of Ras is constitutively activated.

The constitutively active Ras protein to be used in the present invention is not particularly limited as long as it can constitutively activate at least one of the 3 signal transduction pathways at the downstream of Ras (PI3 kinase pathway, Ral pathway, MAP kinase pathway). It preferably constitutively activates 1 or 2 signal transduction pathways from PI3 kinase pathway, Ral pathway and MAP kinase pathway, more preferably PI3 kinase pathway and/or Ral pathway. Specific examples of the Ras protein that constitutively activates PI3 kinase pathway and/or Ral pathway include, but are not limited to, ERas, a double mutant wherein 12th glycine of H-, K- or N-Ras is substituted by valine, and 37th glutamic acid is substituted by glycine or 40th tyrosine is substituted by cysteine and the like.

The Ras protein to be used in the present invention may be a protein containing an amino acid sequence which is the amino acid sequence of any of the above-mentioned Ras proteins wherein 1 or more, preferably 1-20, more preferably 1-10, still more preferably 1-several (5, 4, 3, 2), amino acids are substituted, deleted, inserted or added, as long as any of the 3 signal transduction pathways at the downstream of Ras is not constitutively inactivated, preferably none of PI3 kinase pathway and Ral pathway is constitutively inactivated. Alternatively, it may be a protein containing an amino acid sequence having identity of not less than 80%, preferably not less than 90%, more preferably not less than 95%, still more preferably not less than 97%, particularly preferably not less than 98%, with the amino acid sequence of any of the above-mentioned Ras proteins. Preferred is a protein that conserves Caax motif necessary for membrane localization, and G1 (10-17th amino acids), G2 (32-36th amino acids), G3 (57-60th amino acids), G4 (116-119th amino acids), G5 (145-147th amino acids) domain, and effector domain (26-45th amino acids) essential for the function of Ras, or a protein that is mutated to provide constitutively activation.

(b2) Ras Target Factor (Effector)

As the "Ras target factor (effector)" to be used in the present invention, PI3 kinase, RalGEF and Raf can be mentioned.

PI3 kinase in the present invention is a class IA PI3 kinase to be the target factor of Ras, which consists of p110 catalytic subunit (3 isoforms of α, β and δ) and regulatory subunit (p85α, p85β, p55γ and splicing variants thereof). Of these, p110 having a domain relating to the binding with Ras and a kinase domain that catalyzes the phosphorylation reaction from phosphatidylinositol-4,5-diphosphoric acid ($PIP_2$) to phosphatidylinositol-3,4,5-triphosphoric acid ($PIP_3$) can be preferably used as an establishment efficiency improving factor in the present invention.

Preferable examples of p110 protein include mouse p110α consisting of the amino acid sequence shown by SEQ ID NO:19 (RefSeq Accession No. NP_032865), human p110α consisting of the amino acid sequence shown by SEQ ID NO:21 (RefSeq Accession No. NP_006209), mouse p110β (RefSeq Accession No. NP_083370), human p110β (RefSeq Accession No. NP_006210), mouse p110δ (RefSeq Accession No. NP_0010250058), human p110δ (RefSeq Accession No. NP_005017), orthologs thereof in other mammals, natural allelic variants and polymorphic variants thereof, splicing variants thereof, natural and artificial activated mutants thereof and the like. While p110 homologous to the animal species of the somatic cell to be the introduction target is desirably used, heterologous p110 can also be used.

Preferable examples of RalGEF protein include mouse RalGDS consisting of the amino acid sequence shown by SEQ ID NO:23 (RefSeq Accession No. NP_033084), human RalGDS consisting of the amino acid sequence shown by SEQ ID NO:25 (RefSeq Accession No. NP_006266), mouse Rgl (RefSeq Accession No. NP_058542), human Rgl (RefSeq Accession No. NP_055964), mouse Rlf/Rgl2 (RefSeq Accession No. NP_033085), human Rlf/Rgl2 (RefSeq Accession No. NP_004752), orthologs thereof in other mammals, natural allelic variants and polymorphic variants thereof, splicing variants thereof, natural and artificial activated mutants thereof and the like. While RalGEF homologous to the animal species of the somatic cell to be the introduction target is desirably used, heterologous RalGEF can also be used.

Preferable examples of Raf protein include mouse c-Raf consisting of the amino acid sequence shown by SEQ ID NO:27 (RefSeq Accession No. NP_084056), human c-Raf consisting of the amino acid sequence shown by SEQ ID NO:29 (RefSeq Accession No. NP_002871), mouse A-Raf (RefSeq Accession No. NP_033833), human A-Raf (RefSeq Accession No. NP_001645), mouse B-Raf (RefSeq Accession No. NP_647455), human B-Raf (RefSeq Accession No. NP_004324), orthologs thereof in other mammals, natural allelic variants and polymorphic variants thereof, splicing variants thereof, natural and artificial activated mutants thereof and the like. While Raf homologous to the animal species of the somatic cell to be the introduction target is desirably used, heterologous Raf can also be used.

Ras target factors such as PI3 kinase, RalGEF, Raf and the like are activated by being localized on the inner surface of the plasma membrane via binding to activated Ras, and activates signal transduction pathway in the downstream. Therefore, the level of activated Ras target factor can be efficiently increased by introducing constitutively active mutants of these target factors into somatic cells. For example, since Ras target factor is activated by being localized on the membrane, a constitutively active mutant of the target factor can be produced by adding a membrane localization signal sequence to the N-terminal or C-terminal of the target factor. For example, a membrane-localized constitutively active mutant can be obtained by adding a myristoylation signal sequence (e.g., c-Src-derived myristoylation signal sequence (MGSSKSKPKDPSQRRRRIRT; SEQ ID NO:30)) to the N-terminal of the target factor (e.g., Myr-PI3K of Example 3 etc.), or adding Caax motif to the C-terminal (e.g., PI3K-CaaX of Example 3, RalGDS-Caax and Raf-CaaX of Example 4, etc.). Examples of other constitutively active mutant include, but are not limited to, PI3 kinase mutant wherein 1047th histidine of p110α is substituted by arginine, PI3 kinase mutant wherein 545th glutamic acid of p110α is substituted by lysine, PI3 kinase mutant wherein 227th lysine of p110α is substituted by glutamic acid, PI3 kinase mutant wherein 108 amino acids at the N-terminus (regulatory subunit binding domain) of p110 are deleted, Raf mutant wherein 305 amino acids at the N-terminus (including Ras binding domain) of c-Raf are deleted, Raf mutant wherein 600th valine of B-Raf is substituted by glutamic acid, Raf mutant wherein 340th tyrosine of c-Raf is substituted by aspartic acid and the like.

The Ras target factor in constitutively active form to be used in the present invention is preferably a constitutively active mutant of PI3 kinase (p110) or RalGEF, which is specifically exemplified by Myr-PI3K, PI3K-CaaX, RalGDS-CaaX and the like used in the Examples to be described below.

PI3 kinase in constitutively active form to be used in the present invention constitutively activates the signal transduction pathway of AKT pathway.

The Ras target factor to be used in the present invention may be a protein containing an amino acid sequence which is the amino acid sequence of any of the above-mentioned Ras target factor wherein 1 or more, preferably 1-20, more preferably 1-10, still more preferably 1-several (5, 4, 3, 2), amino acids are substituted, deleted, inserted or added, as long as the signal transduction pathway at the downstream of the target factor is not constitutively inactivated. Alternatively, it may be a protein containing an amino acid sequence having identity of not less than 80%, preferably not less than 90%, more preferably not less than 95%, still more preferably not less than 97%, particularly preferably not less than 98%, with the amino acid sequence of any of the above-mentioned Ras proteins.

(b3) Signaling Factor Downstream of Ras Target Factor (Effector) and Activator of the Signaling Examples of the "signaling factor downstream of Ras target factor (effector)" to be used in the present invention" include AKT family members, Rheb and S6K, and examples of the "activator of signaling downstream of Ras target factor (effector)" include TCL1.

The "AKT family member" in the present specification is a protein identified as a gene homologous to viral oncogene v-Akt, and capable of transmitting the signal for activation of mTOR at the downstream thereof. Preferable examples of AKT family members include, but are not limited to, AKT1, AKT2, AKT3 and the like. Preferable examples of AKT protein include mouse Akt1 consisting of the amino acid sequence shown by SEQ ID NO:35 (RefSeq Accession No. NP_001159366), human AKT1 consisting of the amino acid sequence shown by SEQ ID NO:37 (RefSeq Accession No. NP_001014432), orthologs thereof in other mammals, natural allelic variants and polymorphic variants thereof, splicing variants thereof (e.g., RefSeq Accession No. NP_033782, RefSeq Accession No. NP_001014431, RefSeq Accession No. NP_005154 and the like), natural and artificial activated mutants thereof and the like. While AKT family members homologous to the animal species of the somatic cell to be the introduction target are desirably used, heterologous AKT family members can also be used.

Preferable examples of Rheb protein include mouse Rheb consisting of the amino acid sequence shown by SEQ ID NO:39 (RefSeq Accession No. NP_444305), human RHEB consisting of the amino acid sequence shown by SEQ ID NO:41 (RefSeq Accession No. NP_005605), orthologs thereof in other mammals, natural allelic variants and polymorphic variants thereof, splicing variants thereof, natural and artificial activated mutants thereof and the like. While Rheb homologous to the animal species of the somatic cell to be the introduction target is desirably used, heterologous Rheb can also be used.

Preferable examples of TCL1 protein include mouse Toil consisting of the amino acid sequence shown by SEQ ID NO:43 (RefSeq Accession No. NP_033363), human TCL1A consisting of the amino acid sequence shown by SEQ ID NO:45 (RefSeq Accession No. NP_001092195), orthologs thereof in other mammals, natural allelic variants and polymorphic variants thereof, splicing variants thereof (e.g., RefSeq Accession No. NP_068801 and the like), natural and artificial activated mutants thereof and the like. While TCL1 homologous to the animal species of the somatic cell to be the introduction target is desirably used, heterologous TCL1 can also be used.

Preferable examples of S6K protein include S6K consisting of the amino acid sequence shown by SEQ ID NO:47 (RefSeq Accession No. NP_001107806), human S6K1 consisting of the amino acid sequence shown by SEQ ID NO:49 (RefSeq Accession No. NP_003152), orthologs thereof in other mammals, natural allelic variants and polymorphic variants thereof, splicing variants thereof (e.g., RefSeq Accession No. NP_082535 and the like), natural and artificial activated mutants thereof and the like. While S6K homologous to the animal species of the somatic cell to be the introduction target is desirably used, heterologous S6K can also be used.

AKT family members are activated by being localized on the inner surface of the plasma membrane via binding to activated Ras, PI3 kinase etc., and activates signal transduction pathway in the downstream. Therefore, the level of downstream signaling factor can be efficiently increased by introducing constitutively active mutants of AKT family members into somatic cells. For example, since AKT family member is activated by being localized on the membrane, a constitutively active mutant of the target factor can be produced by adding a membrane localization signal sequence to the N-terminal or C-terminal of the target factor. For example, a membrane-localized constitutively active mutant can be obtained by adding a myristoylation signal sequence (e.g., c-Src-derived myristoylation signal sequence (MGSSKSKPKDPSQRRRRIRT; SEQ ID NO:30)) to the N-terminal of the target factor (e.g., Myr-AKT1 of Example 8 etc.). Examples of other constitutively active mutant include, but are not limited to, AKT1 mutant wherein 40th glutamic acid of AKT1 is substituted by lysin (E40K-AKT1), AKT1 mutant wherein 17th glutamic acid of AKT 1 is substituted by lysine (E17K-AKT1) and the like.

S6K protein is generally converted to an activated form by phosphorylation of 389th threonine, and has been reported to be constitutively activated by converting the 389th to glutamic acid. The level of S6K protein in activated form can be efficiently increased by introducing such constitutively active mutant of S6K protein into a somatic cell.

The signaling factor downstream of Ras target factor (effector) and activator of the signaling to be used in the present invention may be a protein containing an amino acid sequence which is the amino acid sequence of any of the above-mentioned signaling factor downstream of Ras target factor (effector) and activator of the signaling wherein 1 or more, preferably 1-20, more preferably 1-10, still more preferably 1-several (5, 4, 3, 2), amino acids are substituted, deleted, inserted or added, as long as the signal transduction pathway at the downstream of the target factor is not constitutively inactivated. Alternatively, it may be a protein containing an amino acid sequence having identity of not less than 80%, preferably not less than 90%, more preferably not less than 95%, still more preferably not less than 97%, particularly preferably not less than 98%, with the amino acid sequence of any of the above-mentioned AKT family members, Rheb, S6K and TCL1 protein.

The signaling factor downstream of the target factor (effector) of Ras in constitutively active form to be used in the present invention and the activator of the signaling are preferably constitutively active mutants of AKT family members or S6K. Specific examples thereof includes Myr-AKT1, Myr-AKT2, Myr-AKT3, S6K1 T389E and the like used in the Examples described later.

(b4) Ras Activator

When receptor tyrosine kinase is activated by stimulation with an extracellular signal such as growth factor and the like, autophosphorylation occurs, and RasGEF (Sos, Ras-GRF, RasGRF2, RasGRP, SmgGDS, Vav, C3G and the like) is recruited to the plasma membrane via an adapter protein that recognizes the autophosphorylated molecule such as Grb2, Shc and the like, whereby Ras protein localized in the plasma membrane is activated. Therefore, the iPS cell establishment efficiency can also be improved via activation of Ras protein by introduction of RasGEF and adapter protein into somatic cells.

Preferable examples of Sos protein include mouse Sos1 (RefSeq Accession No. NP_033257), human Sos1 (RefSeq Accession No. NP_005624), mouse Sos2 (RefSeq Accession No. XP 127051), human Sos2 (RefSeq Accession No. NP_008870), orthologs thereof in other mammals, natural allelic variants and polymorphic variants thereof, splicing variants thereof, natural and artificial activated mutants thereof and the like. While Sos homologous to the animal species of the somatic cell to be the introduction target is desirably used, heterologous Sos can also be used. Examples of the artificial activated mutant include membrane localized mutant wherein Caax motif is added to the aforementioned C-terminal or myristoylation signal is added to the N-terminal.

The amino acid sequences of other RasGEF proteins such as RasGRF, RasGRF2, RasGRP, SmgGDS, Vav, C3G and the like are known, and polymorphic variants and splicing variants thereof are also known. Examples of the activated mutant of these proteins include membrane localized mutant wherein Caax motif is added to the aforementioned C-terminal or myristoylation signal is added to the N-terminal.

Preferable examples of Grb2 protein include mouse Grb2 (RefSeq Accession No. NP_032189), human Grb2 (RefSeq Accession No. NP_002077), orthologs thereof in other mammals, natural allelic variants and polymorphic variants thereof, splicing variants thereof, natural and artificial activated mutants thereof and the like. While Grb2 homologous to the animal species of the somatic cell to be the introduction target is desirably used, heterologous Grb2 can also be used. Examples of the artificial activated mutant include membrane localized mutant wherein Caax motif is added to the aforementioned C-terminal or myristoylation signal is added to the N-terminal.

The proteins of (b1)-(b4) (sometimes to be referred to as "proteinous establishment efficiency improving factors of the present invention") may be isolated from, for example, a cell or tissue [e.g., cells and tissues of thymus, bone marrow, spleen, brain, spinal cord, heart, skeletal muscle, kidney, lung, liver, pancreas or prostate, progenitor cells, stem cells or cancer cells of these cells, and the like] of a human or another mammal (e.g., mouse, rat, monkey, pig, dog and the like) by a protein separation and purification technique known per se. Preferably, it is prepared as a recombinant protein by cloning cDNA from the above-mentioned cell or tissue by a conventional method and expressing same in a suitable host cell. The above-mentioned various activated mutants can be produced by introduction of point mutation or addition of a membrane localization signal sequence to the terminus by a gene recombination technique known per se.

Transfer of the proteinous establishment efficiency improving factor of the present invention to a somatic cell can be achieved using a method known per se for protein transfer into a cell. Such methods include, for example, the method using a protein transfer reagent, the method using a protein transfer domain (PTD)—or cell penetrating peptide (CPP)—fusion protein, the microinjection method and the like. Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IMGENEX); those based on a lipid, such as Profect-1 (Targeting Systems); those based on a membrane-permeable peptide, such as Penetrain Peptide (Q biogene) and Chariot Kit (Active Motif), GenomONE (ISHIHARA SANGYO KAISHA, LTD.) utilizing HVJ envelope (inactive hemagglutinating virus of Japan) and the like. The transfer can be achieved per the protocols attached to these reagents, a common procedure being as described below. The proteinous establishment efficiency improving factor of the present invention is diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium.

Developed PTDs include those using transcellular domains of proteins such as drosophila-derived AntP, HIV-derived TAT (Frankel, A. et al, *Cell* 55, 1189-93 (1988) or Green, M. & Loewenstein, P. M. *Cell* 55, 1179-88 (1988)), Penetratin (Derossi, D. et al, *J. Biol. Chem.* 269, 10444-50 (1994)), Buforin II (Park, C. B. et al. *Proc. Natl. Acad. Sci. USA* 97, 8245-50 (2000)), Transportan (Pooga, M. et al. *FASEB J.* 12, 67-77 (1998)), MAP (model amphipathic peptide) (Oehlke, J. et al. *Biochim. Biophys. Acta.* 1414, 127-39 (1998)), K-FGF (Lin, Y. Z. et al. *J. Biol. Chem.* 270, 14255-14258 (1995)), Ku70 (Sawada, M. et al. *Nature Cell Biol.* 5, 352-7 (2003)), Prion (Lundberg, P. et al. *Biochem. Biophys. Res. Commun.* 299, 85-90 (2002)), pVEC (Elmquist, A. et al. *Exp. Cell Res.* 269, 237-44 (2001)), Pep-1 (Morris, M. C. et al. *Nature Biotechnol.* 19, 1173-6 (2001)), Pep-7 (Gao, C. et al. *Bioorg. Med. Chem.* 10, 4057-65 (2002)), SynB1 (Rousselle, C. et al. *Mol. Pharmacol.* 57, 679-86 (2000)), HN-I (Hong, F. D. & Clayman, G L. *Cancer Res.* 60, 6551-6 (2000)), and HSV-derived VP22. CPPs derived from the PTDs include polyarginines such as 11R (*Cell Stem Cell,* 4, 381-384 (2009)) and 9R (*Cell Stem Cell,* 4, 472-476 (2009)).

A fused protein expression vector incorporating cDNA encoding the proteinous establishment efficiency improving factor of the present invention and PTD sequence or CPP sequence is prepared, and recombination expression is performed using the vector. The fused protein is recovered and used for transfer. Transfer can be performed in the same manner as above except that a protein transfer reagent is not added.

Microinjection, a method of placing a protein solution in a glass needle having a tip diameter of about 1 μm, and injecting the solution into a cell, ensures the transfer of the protein into the cell.

Other useful methods of protein transfer include the electroporation method, the semi-intact cell method [Kano, F. et al. Methods in Molecular Biology, Vol. 322, 357-365 (2006)], and transfer using the Wr-t peptide [Kondo, E. et al., Mol. Cancer Ther. 3(12), 1623-1630 (2004)] and the like.

The protein transferring operation can be performed one or more optionally chosen times (e.g., once or more to 10 times or less, or once or more to 5 times or less and the like). Preferably, the transferring operation can be performed twice or more (e.g., 3 times or 4 times) repeatedly. The time interval for repeated transferring operation is, for example, 6 to 48 hours, preferably 12 to 24 hours.

(b5) Nucleic Acid Encoding the Proteinous Establishment Efficiency Improving Factor of the Present Invention The nucleic acid encoding the proteinous establishment efficiency improving factor of the present invention (Ras family members, Ras target factor (effector), signaling factor downstream of Ras target factor (effector), activator of the signaling and Ras activator) (sometimes to be referred to as "the nucleic acidic establishment efficiency improving factor of the present invention") is not particularly limited as long as it encodes the above-mentioned Ras family members (e.g., HRas, KRas, NRas, ERas etc.), Ras target factor (effector) (e.g., PI3 kinase, RalGEF, Raf etc.), signaling factor downstream of Ras target factor (effector) (e.g., AKT1, AKT2, AKT3, Rheb, S6K etc.), activator of the signaling downstream of Ras target factor (effector) (e.g., TCL1 etc.) or Ras activator (e.g., RasGEF, receptor tyrosine kinase adapter protein etc.) in the present invention. The nucleic acid may be a DNA or an RNA, or a DNA/RNA chimera, with preference given to a DNA. The nucleic acid may be double-stranded or single-stranded. In the case of double strands, the nucleic acid may be a double-stranded DNA, a double-stranded RNA or a DNA:RNA hybrid.

The nucleic acidic establishment efficiency improving factor of the present invention can be cloned from a cDNA derived from a cell or tissue [e.g., cells and tissues of thymus, bone marrow, spleen, brain, spinal cord, heart, skeletal muscle, kidney, lung, liver, pancreas or prostate, progenitor cells, stem cells or cancer cells of these cells, and the like] of a human or another mammal (e.g., mice, rats, monkeys, pigs, dogs and the like) by a conventional method.

Examples of the nucleic acid encoding HRas include a nucleic acid comprising the nucleotide sequence shown by SEQ ID NO:1 or 3, and a nucleic acid containing a nucleotide sequence capable of hybridizing with a sequence complementary to the nucleotide sequence shown by SEQ ID NO:1 or 3 under stringent conditions, and encoding a protein capable of activating at least one of the 3 signal transduction pathways at the downstream of Ras, preferably PI3 kinase pathway and/or Ral pathway.

Examples of the nucleic acid encoding KRas include a nucleic acid comprising the nucleotide sequence shown by SEQ ID NO:5 or 7, and a nucleic acid containing a nucleotide sequence capable of hybridizing with a sequence complementary to the nucleotide sequence shown by SEQ ID NO:5 or 7 under stringent conditions, and encoding a protein capable of activating at least one of the 3 signal transduction pathways at the downstream of Ras, preferably PI3 kinase pathway and/or Ral pathway.

Examples of the nucleic acid encoding NRas include a nucleic acid comprising the nucleotide sequence shown by SEQ ID NO:9 or 11, and a nucleic acid containing a nucleotide sequence capable of hybridizing with a sequence complementary to the nucleotide sequence shown by SEQ ID NO:9 or 11 under stringent conditions, and encoding a protein capable of activating at least one of the 3 signal transduction pathways at the downstream of Ras, preferably PI3 kinase pathway and/or Ral pathway.

Examples of the nucleic acid encoding ERas include a nucleic acid comprising the nucleotide sequence shown by SEQ ID NO:13 or 15, and a nucleic acid containing a nucleotide sequence capable of hybridizing with a sequence complementary to the nucleotide sequence shown by SEQ ID NO:13 or 15 under stringent conditions, and encoding a protein capable of activating at least one of the 3 signal transduction pathways at the downstream of Ras, preferably PI3 kinase pathway and/or Ral pathway.

Examples of the nucleic acid encoding catalytic subunit (p110) of PI3 kinase include a nucleic acid encoding p110α containing the nucleotide sequence shown by SEQ ID NO:18 or 20, and a nucleic acid containing a nucleotide sequence capable of hybridizing with a sequence complementary to the nucleotide sequence shown by SEQ ID NO:18 or 20 under stringent conditions, and encoding a protein capable of activating PI3 kinase pathway. Alternatively, a nucleic acid containing the cDNA sequence of mouse p110β (RefSeq Accession No. NM_029094), human p110β (RefSeq Accession No. NM_006219), mouse p110δ (RefSeq Accession No. NM_001029837), human p110δ (RefSeq Accession No. NM_005026), and a nucleic acid containing a nucleotide sequence capable of hybridizing with a sequence complementary to the cDNA sequence and encoding a protein capable of activating PI3 kinase pathway can be mentioned.

Examples of the nucleic acid encoding RalGEF include a nucleic acid encoding RalGDS containing the nucleotide sequence shown by SEQ ID NO:22 or 24, and a nucleic acid containing a nucleotide sequence capable of hybridizing with a sequence complementary to the nucleotide sequence shown by SEQ ID NO:22 or 24 under stringent conditions and encoding a protein capable of activating Ral pathway. Alternatively, a nucleic acid containing the cDNA sequence of mouse Rgl (RefSeq Accession No. NM_016846), human Rgl (RefSeq Accession No. NM_015149), mouse Rlf/Rgl2 (RefSeq Accession No. NM_009059), human Rlf/Rgl2 (RefSeq Accession No. NM_004761), and a nucleic acid containing a nucleotide sequence capable of hybridizing with a sequence complementary to the cDNA sequence and encoding a protein capable of activating Ral pathway can be mentioned.

Examples of the nucleic acid encoding RalGEF include a nucleic acid encoding c-Raf containing the nucleotide sequence shown by SEQ ID NO:26 or 28, and a nucleic acid containing a nucleotide sequence capable of hybridizing with a sequence complementary to the nucleotide sequence shown by SEQ ID NO:26 or 28 under stringent conditions and encoding a protein capable of activating MAP kinase pathway. Alternatively, a nucleic acid containing the cDNA sequence of mouse A-Raf (RefSeq Accession No. NM_009703), human A-Raf (RefSeq Accession No. NM_001654), mouse B-Raf (RefSeq Accession No. NM_139294), human B-Raf (RefSeq Accession No. NM_004333), and a nucleic acid containing a nucleotide sequence capable of hybridizing with a sequence complementary to the cDNA sequence and encoding a protein capable of activating MAP kinase pathway can be mentioned.

Examples of the nucleic acid encoding Sos include a nucleic acid containing the cDNA sequence of mouse Sos1 (RefSeq Accession No. NM_009231), human Sos1 (RefSeq Accession No. NM_005633), mouse Sos2 (RefSeq Accession No. XM_127051), human Sos2 (RefSeq Accession No. NM_006939), and a nucleic acid containing a nucleotide sequence capable of hybridizing with a sequence complementary to the cDNA sequence and encoding a protein capable of activating Ras protein.

The cDNA sequences of other RasGEF proteins such as RasGRF, RasGRF2, RasGRP, SmgGDS, Vav, C3G and the like are known, and polymorphic variants and splicing variants thereof are also known.

Examples of the nucleic acid encoding Grb2 include a nucleic acid containing the cDNA sequence of mouse Grb2 (RefSeq Accession No. NM_008163), human Grb2 (RefSeq Accession No. NM_002086), and a nucleic acid containing a nucleotide sequence capable of hybridizing with a sequence complementary to the cDNA sequence and encoding a protein capable of recognizing and binding to a receptor tyrosine kinase, and recruiting RasGEF to the plasma membrane to activate Ras protein.

Examples of the nucleic acid encoding AKT1 as one embodiment of the AKT family members include a nucleic acid containing the nucleotide sequence shown by SEQ ID NO:34 or 36, and a nucleic acid containing a nucleotide sequence capable of hybridizing with a sequence complementary to the nucleotide sequence shown by SEQ ID NO:34 or 36 under stringent conditions and encoding a protein capable of activating AKT pathway.

Examples of the nucleic acid encoding Rheb include a nucleic acid containing the nucleotide sequence shown by SEQ ID NO:38 or 40, and a nucleic acid containing a nucleotide sequence capable of hybridizing with a sequence complementary to the nucleotide sequence shown by SEQ ID NO:38 or 40 under stringent conditions and encoding a protein capable of activating mTOR pathway at the downstream.

Examples of the nucleic acid encoding TCL1 include a nucleic acid containing the nucleotide sequence shown by SEQ ID NO:42 or 44, and a nucleic acid containing a nucleotide sequence capable of hybridizing with a sequence complementary to the nucleotide sequence shown by SEQ ID NO:42 or 44 under stringent conditions and encoding a protein capable of activating AKT1 protein.

Examples of the nucleic acid encoding S6K include a nucleic acid containing the nucleotide sequence shown by SEQ ID NO:46 or 48, and a nucleic acid containing a nucleotide sequence capable of hybridizing with a sequence complementary to the nucleotide sequence shown by SEQ ID NO:46 or 48 under stringent conditions and encoding a protein capable of activating S6 protein.

A useful nucleic acid capable of hybridizing with a sequence complementary to the nucleotide sequence shown by each SEQ ID NO under stringent conditions is a nucleic acid comprising a nucleotide sequence having an identity of about 80% or more, preferably about 90% or more, more preferably about 95% or more, to the nucleotide sequence shown by each SEQ ID NO. Examples of stringent conditions include conditions described in Current Protocols in Molecular Biology, John Wiley & Sons, 6.3.1-6.3.6, 1999, e.g., hybridization with 6×SSC (sodium chloride/sodium citrate)/45° C. followed by not less than one time of washing with 0.2×SSC/0.1% SDS/50 to 65° C.; those skilled art can choose as appropriate hybridization conditions that give equivalent stringency.

The proteinous establishment efficiency improving factor of the present invention is preferably a constitutively active molecule of Ras protein, a constitutively active molecule of Ras target factor (effector), a constitutively active molecule of signaling factor downstream of Ras target factor, an activated molecule of signaling downstream of Ras target factor or a constitutively active molecule of Ras activator. Accordingly, the nucleic acidic establishment efficiency improving factor of the present invention is preferably a nucleic acid encoding the above-mentioned constitutively active molecule. Said nucleic acid can be prepared by introducing the object amino acid substitution into a nucleic acid encoding a wild-type molecule obtained as mentioned above by site-directed mutagenesis, or adding an oligonucleotide encoding a membrane localization signal sequence to the terminus thereof by using ligase or PCR.

Transfer of the nucleic acidic establishment efficiency improving factor of the present invention to a somatic cell can be achieved using a method of gene transfer to cells known per se. A nucleic acid encoding Ras protein, Ras target factor, signaling factor downstream of Ras target factor, activator of the signaling or Ras activator is inserted into an appropriate expression vector comprising a promoter capable of functioning in a host somatic cell. Useful expression vectors include, for example, viral vectors such as retrovirus, lentivirus, adenovirus, adeno-associated virus, herpes virus and Sendai virus, plasmids for the expression in animal cells (e.g., pA1-11, pXT1, pRc/CMV, pRc/RSV, pcDNAI/Neo) and the like.

The type of a vector to be used can be chosen as appropriate according to the intended use of the iPS cell to be obtained. Useful vectors include adenoviral vector, plasmid vector, adeno-associated viral vector, retroviral vector, lentiviral vector, Sendai viral vector and the like.

Examples of promoters used in expression vectors include the EF1α promoter, the CAG promoter, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EF1α promoter, the CAG promoter, the MoMuLV LTR, the CMV promoter, the SRα promoter and the like.

The expression vector may contain as desired, in addition to a promoter, an enhancer, a polyadenylation signal, a selectable marker gene, a SV40 replication origin and the like. Examples of selectable marker genes include the dihydrofolate reductase gene, the neomycin resistant gene, the puromycin resistant gene and the like.

A nucleic acid that encodes Ras protein, Ras target factor, signaling factor downstream of Ras target factor, activator of the signaling or Ras activator may be integrated alone into an expression vector, or along with one or more reprogramming genes into an expression vector. Preference is given to the former case when using a retroviral or lentiviral vector, which offer high gene transfer efficiency, and to the latter case when using a plasmid, adenoviral, or episomal vector and the like, but there are no particular limitations.

In the context above, when a nucleic acid encoding Ras protein, Ras target factor, signaling factor downstream of Ras target factor, activator of signal thereof or Ras activator and one or more reprogramming genes are integrated in one expression vector, these genes can preferably be integrated into the expression vector via a sequence enabling polycistronic expression. By using a sequence enabling polycistronic expression, it is possible to more efficiently express a plurality of genes integrated in one expression vector. Useful sequences enabling polycistronic expression include, for example, the 2A sequence of foot-and-mouth disease virus (PLoS ONE 3, e2532, 2008, Stem Cells 25, 1707, 2007), the IRES sequence (U.S. Pat. No. 4,937,190) and the like, with preference given to the 2A sequence.

An expression vector harboring a nucleic acid encoding Ras protein, Ras target factor, signaling factor downstream of Ras target factor, activator of the signaling or Ras activator can be introduced into a cell by a technique known per se according to the choice of the vector. In the case of a viral vector, for example, a plasmid containing the nucleic acid is introduced into an appropriate packaging cell (e.g., Plat-E cells) or a complementary cell line (e.g., 293-cells), the viral vector produced in the culture supernatant is recovered, and the vector is infected to a cell by a method suitable for the viral vector. For example, specific means using a retroviral vector are disclosed in WO2007/69666, Cell, 126, 663-676 (2006) and Cell, 131, 861-872 (2007). Specific means using a lentiviral vector is disclosed in Science, 318, 1917-1920 (2007). When iPS cells are utilized as a source of cells for regenerative medicine, the expression (reactivation) of Ras protein, Ras target factor, signaling factor downstream of Ras target factor, activator of the signaling or Ras activator or the activation of a endogenous gene present in the vicinity of the site where exogeneous nucleic acid thereof is integrated potentially increases the risk of tumorigenesis in tissues regenerated from differentiated cells of iPS cell derivation; therefore, a nucleic acid that encodes Ras protein, Ras target factor or Ras activator is preferably expressed transiently, without being integrated into the chromosome of the cells. From this viewpoint, it is preferable to use an adenoviral vector, which is unlikely to be integrated into the chromosome, is preferred. Specific means using an adenoviral vector is described in *Science*, 322, 945-949 (2008). Adeno-associated virus is unlikely to be integrated into the chromosome, and is less cytotoxic and less phlogogenic than adenoviral vectors, so that it is another preferred vector. Sendai virus vectors are capable of being stably present outside of the chromosome, and can be degraded and removed using an siRNA as required, so that they are preferably utilized as well. Useful Sendai virus vectors are described in *J. Biol. Chem.*, 282, 27383-27391 (2007) or JP-B-3602058.

When a retroviral vector or a lentiviral vector is used, even if silencing of the transgene has occurred, it possibly becomes reactive; therefore, for example, a method can be used preferably wherein a nucleic acid encoding Ras protein, Ras target factor or Ras activator is cut out using the Cre-loxP system, when becoming unnecessary. That is, with loxP sequences arranged on both ends of the nucleic acid in advance, iPS cells are induced, thereafter the Cre recombinase is allowed to act on the cells using a plasmid vector or adenoviral vector, and the region sandwiched by the loxP sequences can be cut out. Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactive (SIN) LTR prepared by deleting the sequence, or substituting the sequence with a polyadenylation sequence such as of SV40. Specific means using the Cre-loxP system and SIN LTR is disclosed in Soldner et al., *Cell*, 136: 964-977 (2009), Chang et al., *Stem Cells*, 27: 1042-1049 (2009).

Meanwhile, being a non-viral vector, a plasmid vector can be transferred into a cell using the lipofection method, liposome method, electroporation method, calcium phosphate co-precipitation method, DEAE dextran method, microinjection method, gene gun method and the like. Specific means using a plasmid as a vector are described in, for example, *Science*, 322, 949-953 (2008) and the like.

When a plasmid vector, an adenovirus vector and the like are used, the transfection can be performed once or more optionally chosen times (e.g., once to 10 times, once to 5 times or the like). When two or more kinds of expression vectors are introduced into a somatic cell, it is preferable that these all kinds of expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre-loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transposase is allowed to act on the cell using a plasmid vector or adenoviral vector so as to completely eliminate the transgene from the chromosome. As examples of preferable transposons, piggyBac, a transposon derived from a lepidopterous insect, and the like can be mentioned. Specific means using the piggyBac transposon is disclosed in Kaji, K. et al., *Nature*, 458: 771-775 (2009), Woltjen et al., *Nature*, 458: 766-770 (2009).

Another preferable non-integration type vector is an episomal vector, which is capable of self-replication outside of the chromosome. Specific means using an episomal vector is disclosed by Yu et al., in *Science*, 324, 797-801 (2009). Where necessary, an expression vector may be constructed by inserting a nucleic acid that encodes Ras protein, Ras target factor or Ras activator into an episomal vector having loxP sequences placed in the same orientation on the 5' and 3' sides of a vector component essential for the replication of the episomal vector, and transferred to a somatic cell.

Examples of the episomal vector include a vector comprising as a vector component a sequence derived from EBV, SV40 and the like necessary for self-replication. The vector component necessary for self-replication is specifically exemplified by a replication origin and a gene that encodes a protein that binds to the replication origin to control the replication; examples include the replication origin oriP and the EBNA-1 gene for EBV, and the replication origin on and the SV40 large T antigen gene for SV40.

The episomal expression vector comprises a promoter that controls the transcription of a nucleic acid encoding Ras protein, Ras target factor, signaling factor downstream of Ras target factor, activator of the signaling or Ras activator. The promoter used may be as described above. The episomal expression vector may further contain as desired an enhancer, a polyadenylation signal, a selection marker gene and the like, as described above. Examples of the selection marker gene include the dihydrofolate reductase gene, the neomycin resistance gene and the like.

The loxP sequences useful in the present invention include, in addition to the bacteriophage P1-derived wild type loxP sequence (SEQ ID NO:31), optionally chosen mutant loxP sequences capable of deleting the sequence flanked by the loxP sequence by recombination when placed in the same orientation at positions flanking a vector component necessary for the replication of the transgene. Examples of such mutant loxP sequences include lox71 (SEQ ID NO:32), mutated in 5' repeat, lox66 (SEQ ID NO:33), mutated in 3' repeat, and lox2272 and lox511, mutated in spacer portion. Although the two loxP sequences placed on the 5' and 3' sides of the vector component may be identical or not, the two mutant loxP sequences mutated in spacer portion must be identical (e.g., a pair of lox2272 sequences, a pair of lox511 sequences). Preference is given to a combination of a mutant loxP sequence mutated in 5' repeat (e.g., lox71) and a mutant loxP sequence mutated in 3' repeat (e.g., lox66). In this case, the loxP sequences remaining on the chromosome have double mutations in the repeats on the 5' side and 3' side as a result of recombination, and are therefore unlikely to be recognized by Cre recombinase, thus reducing the risk of causing a deletion mutation in the chromosome due to unwanted recombination. When the mutant loxP sequences lox71 and lox66 are used in combination, each may be placed on any of the 5' and 3' sides of the aforementioned vector component, but it is necessary that the mutant loxP sequences be inserted in an orientation such that the mutated sites would be located at the outer ends of the respective loxP sequences.

Each of the two loxP sequences is placed in the same orientation on the 5' and 3' sides of a vector constituent essential for the replication of the transgene (i.e., a replication origin, or a gene sequence that encodes a protein that binds to the replication origin to control the replication). The vector constituent flanked by the loxP sequences may be either a replication origin or a gene sequence that encodes a protein that binds to the replication origin to control the replication, or both.

An episomal vector can be transferred into a cell using, for example, the lipofection method, liposome method, electroporation method, calcium phosphate co-precipitation method, DEAE dextran method, microinjection method, gene gun method and the like. Specifically, for example, methods described in *Science*, 324: 797-801 (2009) and elsewhere can be used.

Whether or not the vector component necessary for the replication of the transgene has been removed from the iPS cell can be confirmed by performing a Southern blot analysis or PCR analysis using a nucleic acid comprising a nucleotide sequence in the vector component and/or in the vicinity of the loxP sequence as a probe or primer, with the episome fraction isolated from the iPS cell as a template, and determining the presence or absence of a band or the length of the band detected. The episome fraction can be prepared by a method obvious in the art; for example, methods described in *Science*, 324: 797-801 (2009) and elsewhere can be used.

(c) Nuclear Reprogramming Substances

In the present invention, "a nuclear reprogramming substance" may be configured with any substance, such as a proteinous factor or a nucleic acid that encodes the same (including forms incorporated in a vector), or a low molecular compound, as far as it is a substance (substances) capable of inducing an iPS cell from a somatic cell when transferred alone to the somatic cell, or when contacted along with the establishment efficiency improving factor of the present invention to the somatic cell. When the nuclear reprogramming substance is a proteinous factor or a nucleic acid that encodes the same, preferable nuclear reprogramming substance is exemplified by the following combinations (hereinafter, only the names for proteinous factors are shown).

(1) Oct3/4, Klf4, c-Myc
(2) Oct3/4, Klf4, c-Myc, Sox2 (here, Sox2 is replaceable with Sox1, Sox3, Sox15, Sox17 or Sox18; Klf4 is replaceable with Klf1, Klf2 or Klf5; c-Myc is replaceable with T58A (activated mutant), or L-Myc)
(3) Oct3/4, Klf4, c-Myc, Sox2, Fbx15, Nanog, Eras, TclI
(4) Oct3/4, Klf4, c-Myc, Sox2, TERT, SV40 Large T antigen (hereinafter, SV40LT)
(5) Oct3/4, Klf4, c-Myc, Sox2, TERT, HPV16 E6
(6) Oct3/4, Klf4, c-Myc, Sox2, TERT, HPV16 E7
(7) Oct3/4, Klf4, c-Myc, Sox2, TERT, HPV6 E6, HPV16 E7
(8) Oct3/4, Klf4, c-Myc, Sox2, TERT, Bmil
[For details of these combinations, see WO 2007/069666 (however, in the combination (2) above, for replacement of Sox2 with Sox18, and replacement of Klf4 with Klf1 or Klf5, see *Nature Biotechnology*, 26, 101-106 (2008)); for details of the combination "Oct3/4, Klf4, c-Myc, Sox2", see also *Cell*, 126, 663-676 (2006), Cell, 131, 861-872 (2007) and the like; for details of the combination "Oct3/4, Klf2 (or Klf5), c-Myc, Sox2", see also *Nat. Cell Biol.*, 11, 197-203 (2009); for details of the combination "Oct3/4, Klf4, c-Myc, Sox2, hTERT, SV40LT", see also *Nature*, 451, 141-146 (2008)]
(9) Oct3/4, Klf4, Sox2 [see *Nature Biotechnology*, 26, 101-106 (2008)]
(10) Oct3/4, Sox2, Nanog, Lin28 [see *Science*, 318, 1917-1920 (2007)]
(11) Oct3/4, Sox2, Nanog, Lin28, hTERT, SV40LT [see *Stem Cells*, 26, 1998-2005 (2008)]
(12) Oct3/4, Klf4, c-Myc, Sox2, Nanog, Lin28 [see *Cell Research* (2008) 600-603]
(13) Oct3/4, Klf4, c-Myc, Sox2, SV40LT [see *Stem Cells*, 26, 1998-2005 (2008)]
(14) Oct3/4, Klf4 [see *Nature* 454:646-650 (2008), Cell Stem Cell, 2:525-528 (2008)]
(15) Oct3/4, c-Myc [see *Nature* 454:646-650 (2008)]
(16) Oct3/4, Sox2 [see Nature, 451, 141-146 (2008), WO2008/118820]
(17) Oct3/4, Sox2, Nanog (see WO2008/118820)
(18) Oct3/4, Sox2, Lin28 (see WO2008/118820)
(19) Oct3/4, Sox2, c-Myc, Esrrb [here, Esrrb is replaceable with Esrrg; see *Nat. Cell Biol.*, 11, 197-203 (2009)]
(20) Oct3/4, Sox2, Esrrb [see *Nat. Cell Biol.*, 11, 197-203 (2009)]
(21) Oct3/4, Klf4, L-Myc (see Proc. Natl. Acad. Sci. USA., 107, 14152-14157 (2010))
(22) Oct3/4, Nanog

(23) Oct3/4 [*Cell* 136: 411-419 (2009), *Nature,* 08436, doi:10.1038 published online (2009)]
(24) Oct3/4, Klf4, c-Myc, Sox2, Nanog, Lin28, SV40LT [see *Science,* 324: 797-801 (2009)]

In (1)-(24) above, in place of Oct3/4, other Oct family members, for example, Oct1A, Oct6 and the like, can also be used. In place of Sox2 (or Sox1, Sox3, Sox15, Sox17, Sox18), other Sox family members, for example, Sox7 and the like, can also be used. Furthermore, in (1) to (24) above, when c-Myc or Lin28 is included as a nuclear reprogramming factor, L-Myc or Lin28B can be used in place of c-Myc or Lin28, respectively.

A combination which does not fall in any one of (1) to (24) above, but which comprises all the constituents of any one thereof and an optionally chosen other substance, can also be included in the scope of "nuclear reprogramming substances" in the present invention. Provided that the somatic cell to undergo nuclear reprogramming is endogenously expressing one or more of the constituents of any one of (1) to (24) above at a level sufficient to cause nuclear reprogramming, a combination of only the remaining constituents excluding the endogenously expressed constituents can also be included in the scope of "nuclear reprogramming substances" in the present invention.

Of these combinations, ones wherein at least one, preferably 2 or more, more preferably 3 or more, different nuclear reprogramming genes selected from among Oct3/4, Sox2, Klf4, c-Myc or L-Myc, Nanog, Lin28 or Lin28B and SV40LT, are preferred.

Particularly, if a use of the iPS cells obtained for therapeutic purposes is born in mind, a combination of reprogramming factors without using c-Myc is preferable. Examples thereof include a combination of the three factors of Oct3/4, Sox2 and Klf4 [combination (9) above], a combination of the four factors of Oct3/4, Sox2, Klf4 and L-Myc [combination (2) above], and a combination containing these combinations and free of c-Myc. If a use of the iPS cells obtained for therapeutic purposes is not born in mind (e.g., used as an investigational tool for drug discovery screening and the like), in addition to the three factors consisting of Oct3/4, Sox2 and Klf4 and the four factors consisting of Oct3/4, Sox2, Klf4 and L-Myc, four factors consisting of Oct3/4, Sox2, Klf4 and c-Myc, five or six factors consisting of Oct3/4, Sox2, Klf4 and c-Myc/L-Myc as well as Nanog and/or Lin28/Lin28B, or six or seven factors consisting of the above five or six factors and additional SV40 Large T antigen are exemplified.

Information on the mouse and human cDNA sequences of the aforementioned proteinous factors is available with reference to the NCBI accession numbers mentioned in WO 2007/069666 (in the publication, Nanog is described as ECAT4). Mouse and human cDNA sequence information on Lin28, Lin28B, Esrrb, Esrrg, and L-Myc can be acquired by referring to the following NCBI accession numbers, respectively); those skilled in the art are able to easily isolate these cDNAs.

| Name of gene | Mouse | Human |
|---|---|---|
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| L-Myc | NM_008506 | NM_001033081 |

When a proteinous factor is used as it is as a nuclear reprogramming substance, it can be prepared by inserting the cDNA obtained into an appropriate expression vector, transferring it into a host cell, culturing the cell, and recovering the recombinant proteinous factor from the culture. Meanwhile, when a nucleic acid that encodes a proteinous factor is used as a nuclear reprogramming substance, the cDNA obtained is inserted into a viral vector, episomal vector or plasmid vector in the same manner as with the above-described case of the nucleic acidic establishment efficiency improving factor of the present invention to construct an expression vector, which is subjected to the nuclear reprogramming step. The aforementioned Cre-loxP system or piggyBac transposon system can also be utilized as required. When two or more nucleic acids that encodes two or more proteinous factors are transferred to a cell as nuclear reprogramming substances, the different nucleic acids may be carried by separate vectors, or the plurality of nucleic acids may be joined in tandem to obtain a polycistronic vector. In the latter case, to allow efficient polycistronic expression, it is desirable that the 2A self-cleaving peptide of foot-and-mouth disease virus be inserted between the nucleic acids [see *Science,* 322, 949-953 (2008) and the like].

A nuclear reprogramming substance can be contacted with a somatic cell (a) in the same manner as in the above-mentioned proteinous establishment efficiency improving factor of the present invention when the substance is a proteinous factor or (b) in the same manner as in the above-mentioned nucleic acidic establishment efficiency improving factor of the present invention when the substance is a nucleic acid encoding the proteinous factor of (a).

(d) Other iPS Cell Establishment Efficiency Improvers

Since the iPS cell establishment efficiency has been low, various substances that improve the efficiency have recently been proposed one after another. It can be expected, therefore, that the iPS cell establishment efficiency will be increased by bringing another establishment efficiency improver, in addition to the establishment efficiency improving factor of the present invention described above, into contact with the transfer subject somatic cell.

Examples of iPS cell establishment efficiency improvers include, but are not limited to, histone deacetylase (HDAC) inhibitors [e.g., valproic acid (VPA), low-molecular inhibitors such as trichostatin A (TSA), sodium butyrate (Cell Stem Cell, 7: 651-655 (2010)), MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], DNA methyltransferase inhibitors (e.g., 5'-azacytidine (5' azaC)) (Nat. Biotechnol., 26(7): 795-797 (2008)), G9a histone methyltransferase inhibitors [e.g., low-molecular inhibitors such as BIX-01294 (Cell Stem Cell, 2: 525-528 (2008)), nucleic acid-based expression inhibitors such as siRNAs and shRNAs against G9a (e.g., G9a siRNA (human) (Santa Cruz Biotechnology) and the like) and the like], L-channel calcium agonists (e.g., Bayk8644) (Cell Stem Cell, 3, 568-574 (2008)), p53 inhibitors (e.g., siRNA, shRNA, dominant negative form, etc. against p53 (Cell Stem Cell, 3, 475-479 (2008)), Nature 460, 1132-1135 (2009)), Wnt Signaling (e.g., soluble Wnt3a) (Cell Stem Cell, 3, 132-135 (2008)), 2i/LIF (2i is an inhibitor of mitogen-active protein kinase signalling and glycogen synthase kinase-3, PloS Biology, 6 (10), 2237-2247 (2008))], and ES cell-specific miRNAs [e.g., miR-302-367 cluster (Mol. Cell. Biol. doi: 10.1128/MCB.00398-08), miR-302 (RNA (2008) 14: 1-10), miR-291-3p, miR-294 and miR-295 (Nat. Biotechnol. 27: 459-461 (2009), 3'-phosphoinositide-dependent kinase-1

(PDK1) activator (e.g., PS48 (Cell Stem Cell, 7: 651-655 (2010)) etc.), GLIS family members (e.g., GLIS1 (Nature, 474: 225-229 (2011)), WO2010/098419 etc.)]. As mentioned above, the nucleic acid-based expression inhibitors may be in the form of expression vectors harboring a DNA that encodes an siRNA or shRNA.

Of the aforementioned constituents of nuclear reprogramming substances, SV40 large T, for example, can also be included in the scope of iPS cell establishment efficiency improvers because it is an auxiliary factor unessential for the nuclear reprogramming of somatic cells. While the mechanism of nuclear reprogramming remains unclear, it does not matter whether auxiliary factors, other than the factors essential for nuclear reprogramming, are deemed nuclear reprogramming substances or iPS cell establishment efficiency improvers. Hence, because the somatic cell nuclear reprogramming process is taken as an overall event resulting from contact of a nuclear reprogramming substance and an iPS cell establishment efficiency improver with a somatic cell, it does not always seems to be essential for those skilled in the art to distinguish between the two.

An iPS cell establishment efficiency improver can be contacted with a somatic cell by a method similar to the method mentioned above about the establishment efficiency improving factor of the present invention for each of (a) when the substance is a proteinous factor and (b) when the substance is a nucleic acid encoding the proteinous factor. On the other hand, when the substance is (c) a low-molecular-weight compound, the substance can be contacted with a somatic cell by dissolving the factor at a suitable concentration in an aqueous or non-aqueous solvent, adding the solution to a medium suitable for the culture of somatic cell isolated from human or other mammal (e.g., minimum essential medium (MEM), Dulbecco's modified Eagle medium (DMEM), RPMI1640 medium, 199 medium, F12 medium (when KSR is not used as an improving factor, it may contain about 5-20% fetal bovine serum) and the like) such that the factor concentration falls within the above-mentioned range, and cultivating the cells for a given period. While the contact period is not particularly limited as long as it is sufficient for achieving the nuclear reprogramming of the somatic cell, for example, they may be left copresent in the medium until a positive colony emerges.

An iPS cell establishment efficiency improver, including the establishment efficiency improving factor of the present invention, may be contacted with a somatic cell simultaneously with a nuclear reprogramming substance, and either one may be contacted in advance, as far as the iPS cell establishment efficiency from a somatic cell improves significantly compared with the efficiency obtained in the absence of the improver. In an embodiment, for example, when the nuclear reprogramming substance is a nucleic acid that encodes a proteinous factor and the iPS cell establishment efficiency improver is a chemical inhibitor, the iPS cell establishment efficiency improver can be added to the medium after the cell is cultured for a given length of time after the gene transfer treatment, because the nuclear reprogramming substance involves a given length of time lag from the gene transfer treatment to the mass-expression of the proteinous factor, whereas the iPS cell establishment efficiency improver is capable of rapidly acting on the cell. In another embodiment, for example, when the nuclear reprogramming substance and iPS cell establishment efficiency improver are both used in the form of a viral vector or plasmid vector, both may be simultaneously transferred into the cell.

(e) Improving the Establishment Efficiency by Culture Conditions

The iPS cell establishment efficiency can further be improved by culturing the cells under hypoxic conditions in the nuclear reprogramming process for somatic cells (see Cell Stem Cell., 5(3): 237-241 (2009); WO2010/013845). As mentioned herein, the term "hypoxic conditions" means that the ambient oxygen concentration as of the time of cell culture is significantly lower than that in the atmosphere. Specifically, conditions involving lower oxygen concentrations than the ambient oxygen concentrations in the 5-10% $CO_2$/95-90% air atmosphere, which is commonly used for ordinary cell culture, can be mentioned; examples include conditions involving an ambient oxygen concentration of 18% or less. Preferably, the ambient oxygen concentration is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The ambient oxygen concentration is preferably 0.1% or more (e.g., 0.2% or more, 0.3% or more, 0.4% or more and the like), 0.5% or more (e.g., 0.6% or more, 0.7% or more, 0.8% or more, 0.95% or more and the like), or 1% or more (e.g., 1.1% or more, 1.2% or more, 1.3% or more, 1.4% or more and the like).

Although any method of creating a hypoxic state in a cellular environment can be used, the easiest way is to culture cells in a $CO_2$ incubator permitting adjustments of oxygen concentration, and this represents a suitable case. $CO_2$ incubators permitting adjustment of oxygen concentration are commercially available from various manufacturers (e.g., $CO_2$ incubators for hypoxic culture manufactured by Thermo scientific, Ikemoto Scientific Technology, Juji Field, Wakenyaku etc.).

The time of starting cell culture under hypoxic conditions is not particularly limited, as far as iPS cell establishment efficiency is not prevented from being improved compared with the normal oxygen concentration (20%). Although the culture may be started before the somatic cell is contacted with the establishment efficiency improving factor of the present invention and the nuclear reprogramming substance, or at the same time as the contact, or after the contact, it is preferable, for example, that the culture under hypoxic conditions be started just after the somatic cell is contacted with the establishment efficiency improving factor of the present invention and the nuclear reprogramming substance, or at a given time interval after the contact [e.g., 1 to 10 (e.g., 2, 3, 4, 5, 6, 7, 8 or 9) days].

The duration of cultivation of cells under hypoxic conditions is not particularly limited, as far as iPS cell establishment efficiency is not prevented from being improved compared with the normal oxygen concentration (20%); examples include, but are not limited to, periods of 3 days or more, 5 days or more, for 7 days or more or 10 days or more, and 50 days or less, 40 days or less, 35 days or less or 30 days or less and the like. Preferred duration of cultivation under hypoxic conditions varies depending on ambient oxygen concentration; those skilled in the art can adjust as appropriate the duration of cultivation according to the oxygen concentration used. In an embodiment of the present invention, if iPS cell candidate colonies are selected with drug resistance as an index, it is preferable that a normal oxygen concentration be restored from hypoxic conditions before starting drug selection.

Furthermore, preferred starting time and preferred duration of cultivation for cell culture under hypoxic conditions also vary depending on the choice of nuclear reprogramming substance used, iPS cell establishment efficiency at normal oxygen concentrations and the like.

(f) Selection and Confirmation of iPS Cell

After being contacted with the establishment efficiency improving factor of the present invention and a nuclear reprogramming substance (and other iPS cell establishment efficiency improver), the cell can, for example, be cultured under conditions suitable for cultivation of ES cells. In the case of mouse cells, generally, the cultivation is carried out with the addition of leukemia inhibitory factor (LIF) as a differentiation suppression factor to an ordinary medium. Meanwhile, in the case of human cells, it is desirable that basic fibroblast growth factor (bFGF) and/or stem cell factor (SCF) be added in place of LIF. However, when the establishment efficiency improving factor of the present invention is contacted with somatic cell, human iPS cell colony of the same level as in the presence of bFGF can be obtained even in the absence of bFGF.

Usually, the cell is cultured in the co-presence of mouse embryonic fibroblasts (MEFs) treated with radiation or an antibiotic to terminate the cell division, as feeder cells. Usually, STO cells and the like are commonly used as MEFs; for induction of an iPS cell, however, the SNL cell [McMahon, A. P. & Bradley, A. Cell 62, 1073-1085 (1990)] and the like are commonly used. Co-culture with the feeder cells may be started before contact with the establishment efficiency improving factor of the present invention and a nuclear reprogramming substance, at the time of the contact, or after the contact (e.g., 1-10 days later).

A candidate colony of iPS cells can be selected in two ways: methods with drug resistance and reporter activity as indicators, and methods based on macroscopic examination of morphology. As an example of the former, a colony positive for drug resistance and/or reporter activity is selected using a recombinant cell wherein a drug resistance gene and/or a reporter gene is targeted to the locus of a gene highly expressed specifically in pluripotent cells (e.g., Fbx15, Nanog, Oct3/4 and the like, preferably Nanog or Oct3/4). Examples of such recombinant cells include MEFs and TTFs derived from a mouse having the βgeo (which encodes a fusion protein of β-galactosidase and neomycin phosphotransferase) gene knocked in to the Fbx15 gene locus [Takahashi & Yamanaka, *Cell*, 126, 663-676 (2006)], and MEFs and TTFs derived from a transgenic mouse having the green fluorescent protein (GFP) gene and the puromycin resistance gene integrated in the Nanog gene locus [Okita et al., *Nature*, 448, 313-317 (2007)]. Meanwhile, methods for selecting a candidate colony by macroscopic examination of morphology include, for example, the method described by Takahashi et al. in *Cell*, 131, 861-872 (2007). Although the methods using reporter cells are convenient and efficient, colony selection by macroscopic examination is desirable from the viewpoint of safety when iPS cells are prepared for therapeutic purposes in humans.

The identity of the cells of the selected colony as iPS cells can be confirmed by positive responses to Nanog (or Oct3/4) reporters (puromycin resistance, GFP positivity and the like), as well as by the visible formation of an ES cell-like colony, as described above; however, to ensure greater accuracy, it is possible to perform tests such as alkaline phosphatase staining, analyzing the expression of various ES-cell-specific genes, and transplanting the selected cells to a mouse and confirming teratoma formation.

When a nucleic acid that encodes Ras protein, Ras target factor or Ras activator is transferred to a somatic cell, the iPS cell obtained is a novel cell distinct from conventionally known iPS cells in that the exogenous nucleic acid is contained. In particular, when the exogenous nucleic acid is introduced into a somatic cell using a retrovirus, lentivirus or the like, the exogenous nucleic acid is usually integrated in the genome of the iPS cell obtained, so that the phenotype of containing the exogenous nucleic acid is stably retained.

(g) Use of iPS Cells

The iPS cells thus established can be used for various purposes. For example, by utilizing a method of differentiation induction reported with respect to ES cells (for example, the method described in JP 2002-291469 as a method for inducing differentiation into nerve stem cells, the method described in JP 2004-121165 as a method for inducing differentiation into pancreatic stem-like cells, the method described in JP 2003-505006 as a method for inducing differentiation into hematopoietic cells and the like. Additionally, the method described in JP 2003-523766 as a differentiation induction method via embryonic body formation and the like can be recited as examples), differentiation into various cells (e.g., myocardial cells, blood cells, nerve cells, vascular endothelial cells, insulin-secreting cells and the like) from iPS cells can be induced. Therefore, inducing iPS cells using a somatic cell collected from a patient or another person of the same or substantially the same HLA type would enable stem cell therapy by autogeneic or allogeneic transplantation, wherein the iPS cells are differentiated into desired cells (that is, cells of an affected organ of the patient, cells that have a therapeutic effect on disease, and the like), which are transplanted to the patient. Furthermore, because functional cells (e.g., hepatocytes) differentiated from iPS cells are thought to better reflect the actual state of the functional cells in vivo than do corresponding existing cell lines, they can also be suitably used for in vitro screening for the effectiveness and toxicity of pharmaceutical candidate compounds and the like.

EXAMPLES

The present invention is hereinafter described in further detail by means of the following examples, to which, however, the invention is not limited.

Example 1

Consideration of Effect of Ras Family on Human iPS Cell Establishment

Whether or not Ras family (Nras, Hras, Kras and Eras) has an effect on iPS cell establishment was examined.

Fibroblasts (HDF) derived from the skin of an adult (a 73-year-old female Caucasian, name of cell line 1503) were allowed to express the mouse ecotropic virus receptor Slc7a1 gene using a lentivirus (pLenti6/UbC-Slc7a1), as described by Takahashi, K. et al. in Cell, 131:861-872 (2007). These cells ($1 \times 10^5$ cells/well, 6-well plate) were transfected with the following genes using a retrovirus, as described by Takahashi, K. et al. in Cell, 131:861-872 (2007), and the number of the resultant iPS cell colonies was compared to that obtained by introduction of 4 genes (Oct3/4, Sox2, Klf4, c-Myc).

1) Human Oct3/4, Sox2, Klf4, c-Myc, Nras
2) Human Oct3/4, Sox2, Klf4, c-Myc, Hras
3) Human Oct3/4, Sox2, Klf4, c-Myc, Kras
4) Human Oct3/4, Sox2, Klf4, c-Myc, Eras
5) Human Oct3/4, Sox2, Klf4, c-Myc, V12
6) Human Oct3/4, Sox2, Klf4, c-Myc, SVLS
7) Human Oct3/4, Sox2, Klf4, c-Myc, SSVA
8) Human Oct3/4, Sox2, Klf4, c-Myc, N17

Here, the "V12" is a constitutively active mutant of HRas wherein the 12th glycine of HRas is substituted by valine. V12 is known to activate any pathways of MAP kinase pathway, PI3 kinase pathway and Ral pathway (RalGEF pathway) which are three signal transduction pathways of Ras.

The "SVLS" is an inactivated mutant incapable of localization in the plasma membrane due to the substitution of 4 amino acids CVLS at the C-terminus of H-Ras by SVLS, and "SSVA" is an inactivated mutant incapable of localization in the plasma membrane due to the substitution of 4 amino acids CSVA at the C-terminus of E-Ras by SSVA.

The "N17" is an inactivated mutant (dominant-negative mutant) wherein the 17th serine of H-Ras is substituted by asparagine.

The cells were collected on day 7 from the viral infection, and replated on feeder cells ($2.5 \times 10^5$ cells/100 mm dish). The feeder cells used were SNL cells treated with mitomycin C to terminate the cell division thereof [McMahon, A. P. & Bradley, A. Cell 62, 1073-1085 (1990)]. From day 10 after infection, the cells were cultured in a primate ES cell culture medium (ReproCELL) supplemented with 4 ng/ml recombinant human bFGF (WAKO). The iPS cell colonies were counted on day 24 from the infection, and the fold change when the number of the colonies obtained by 4 transgene is 1 (Red in Figure) is shown in FIG. 1. FIG. 1 shows the mean values of three experiments. By the addition of Eras to the 4 genes, the number of the human iPS cell colonies increased dramatically. Since Eras is known to activate the PI3 kinase pathway, of the Ras signal transduction pathways, activation of the PI3 kinase pathway was suggested to particularly contribute to the promotion of the iPS cell establishment. When other Ras (Nras, Hras, Kras) were added, the number of human iPS cell colonies also increased, though not as much as by Eras.

Example 2

Consideration of Effect of Ras Signal Transduction Pathway on Human iPS Cell Establishment (1)

Among three pathways of the MAP kinase pathway, PI3 kinase pathway and Ral pathway (RalGEF pathway) which are Ras signal transduction pathways, whether or not the activation of any signal transduction pathways has an effect on iPS cell establishment was examined. The following combinations were used for the experiment which was performed in the same manner as in Example 1.
1) Human Oct3/4, Sox2, Klf4, c-Myc, Nras
2) Human Oct3/4, Sox2, Klf4, c-Myc, Hras
3) Human Oct3/4, Sox2, Klf4, c-Myc, Kras
4) Human Oct3/4, Sox2, Klf4, c-Myc, Eras
5) Human Oct3/4, Sox2, Klf4, c-Myc, V12
6) Human Oct3/4, Sox2, Klf4, c-Myc, V12T35S
7) Human Oct3/4, Sox2, Klf4, c-Myc, V12E37G
8) Human Oct3/4, Sox2, Klf4, c-Myc, V12Y40C Here, "V12T35S" is a mutant wherein the MAP kinase pathway is selectively and constitutively activated by the substitution of the 12th glycine of HRas by valine and the 35th threonine by serine.

The "V12E37G" is a mutant wherein the Ral pathway is selectively and constitutively activated by the substitution of the 12th glycine of HRas by valine and the 37th glutamic acid by glycine.

The "V12Y40C" is a mutant wherein the PI3 kinase pathway is selectively and constitutively activated by the substitution of the 12th glycine of HRas by valine and the 40th tyrosine by cysteine.

Figure 2:
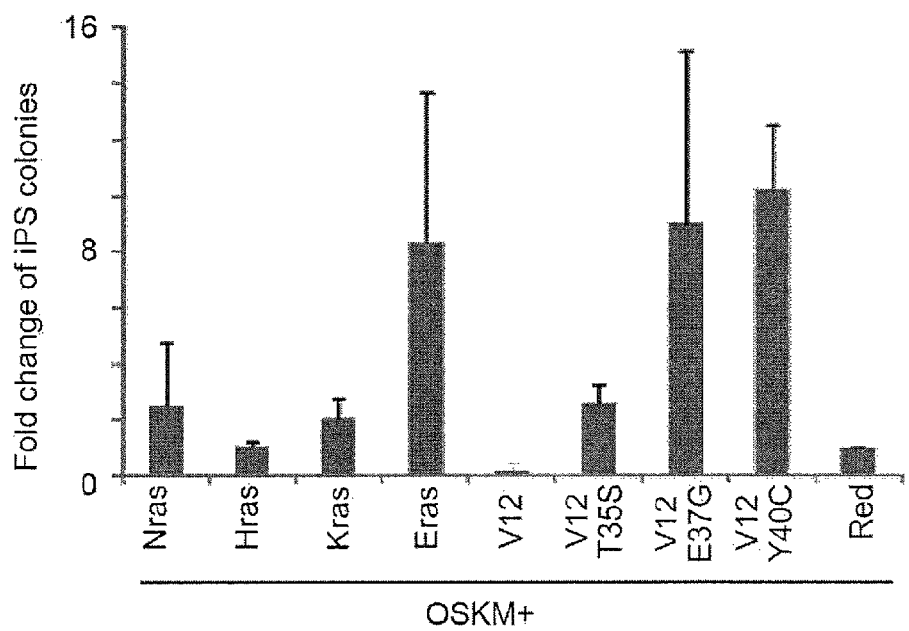
FIG. 2 shows a graph presenting the results of Example 2, wherein the vertical axis shows fold change of the number of iPS colonies when the number of colonies obtained by 4 transgenes of Oct3/4, Sox2, Klf4 and c-Myc is 1 (Red in the Figure), and the horizontal axis shows combinations of Oct3/4, Sox2, Klf4 and c-Myc genes and respective genes shown in the horizontal axis.

The cells were collected on day 7 from the viral infection, and replated on feeder cells ($2.5 \times 10^5$ cells/100 mm dish). From day 10 from the infection, the cells were cultured in a primate ES cell culture medium (ReproCELL) supplemented with 4 ng/ml recombinant human bFGF (WAKO). The iPS cell colonies were counted on day 24 from the infection, and the fold change when the number of the colonies obtained by 4 transgene is 1 (Red in Figure) is shown in FIG. 2. FIG. 2 shows mean values of three experiments. By adding Eras to 4 genes in the same manner as in Example 1, the number of the human iPS cell colonies increased dramatically. In addition, when V12E37G or V12Y40C was added, the number of human iPS cell colonies also increased dramatically. When V12T35S was added, the effect was low. From the above results, activation of the PI3 kinase pathway and Ral pathway was shown to contribute to the promotion of the iPS cell establishment.

Example 3

Consideration of Effect on Different Cells

Using dermal fibroblasts of 6-year-old Japanese female (cell name: TIG120) and dermal fibroblasts of 68-year-old Japanese female (cell name: 1616), an experiment similar to that in the aforementioned Example was performed in the following combinations.
1) Human Oct3/4, Sox2, Klf4, c-Myc, Eras
2) Human Oct3/4, Sox2, Klf4, c-Myc, V12Y40C (simply shown as "Y40C" in FIG. 3)
3) Human Oct3/4, Sox2, Klf4, c-Myc, Myr-PI3K (simply shown as "M-PI3K" in FIG. 3)
4) Human Oct3/4, Sox2, Klf4, c-Myc, PI3K-CaaX (simply shown as "C-PI3K" in FIG. 3)
5) Human Oct3/4, Sox2, Klf4, c-Myc, V12E37G (simply shown as "E37G" in FIG. 3)

Here, "Myr-PI3K (M-PI3K)" is a constitutively active PI3 kinase localized in the membrane by the addition of a myristoylation signal sequence to the N-terminus.

The "PI3K-CaaX (C-PI3K)" is a constitutively active PI3 kinase catalytic subunit localized in the membrane by the addition of a Caax motif sequence to the C-terminus.

Figure 3:
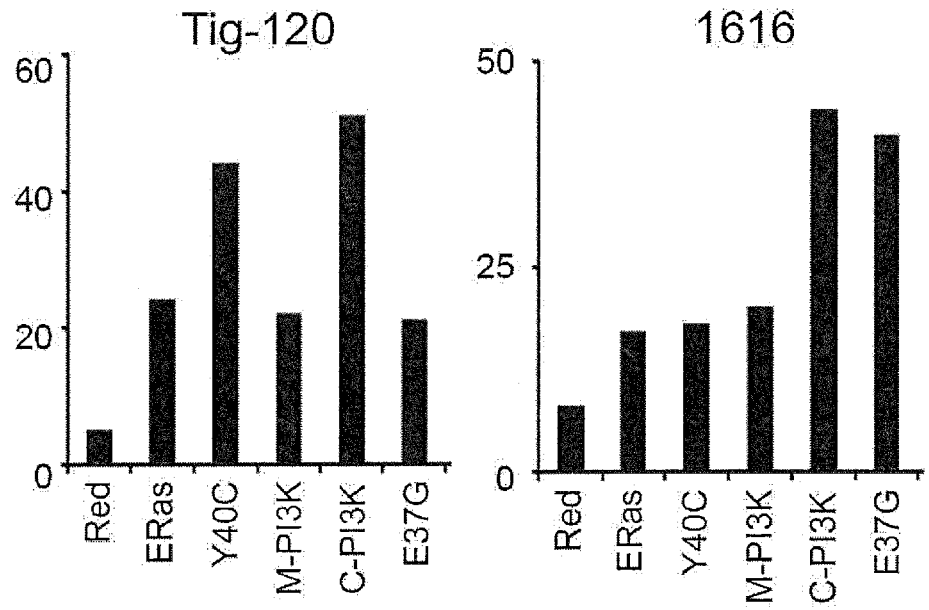
FIG. 3 shows a graph presenting the results of Example 3, wherein the left Figure shows the results using Tig-120 cells, and the right Figure shows the results using 1616 cells. In the Figure, the vertical axis indicates the number of iPS cell colonies, and the horizontal axis shows combinations of Oct3/4, Sox2, Klf4 and c-Myc genes and respective genes shown in the horizontal axis.

The cells were collected on day 7 from the viral infection, and replated on feeder cells ($0.5 \times 10^5$ cells/100 mm dish). From day 10 from the infection, the cells were cultured in a primate ES cell culture medium (ReproCELL) supplemented with 4 ng/ml recombinant human bFGF (WAKO). FIG. 3 shows the number of the iPS cell colonies on day 24 from the infection. FIG. 3 shows mean values of three experiments. By adding Eras, V12Y40C (Y40C) or V12E37G (E37G) to 4 genes in the same manner as in Example 2, the number of the human iPS cell colonies increased. In addition, when a constitutively active form of PI3 kinase was added, the number of colonies increased similarly. From the above results, the activation of the PI3 kinase pathway and Ral pathway was confirmed to contribute to the promotion of iPS cell establishment and to show a similar effect on cells other than HDF1503.

Example 4

Consideration of Effect of Ras Signal Transduction Pathway on Human iPS Cell Establishment (2)

The effect of activation of each Ras signal transduction pathway on iPS cell establishment was examined by an experiment similar to that in the aforementioned Example and using the following combinations.
1) Human Oct3/4, Sox2, Klf4, c-Myc, Nras
2) Human Oct3/4, Sox2, Klf4, c-Myc, Hras
3) Human Oct3/4, Sox2, Klf4, c-Myc, Kras
4) Human Oct3/4, Sox2, Klf4, c-Myc, Eras
5) Human Oct3/4, Sox2, Klf4, c-Myc, V12T35S
6) Human Oct3/4, Sox2, Klf4, c-Myc, V12E37G
7) Human Oct3/4, Sox2, Klf4, c-Myc, Raf-CaaX
8) Human Oct3/4, Sox2, Klf4, c-Myc, RalGDS-CaaX Here, "Raf-CaaX" is a constitutively active form localized in the membrane by the addition of a Caax motif sequence to the C-terminus of MAP kinase kinase kinase (MAPKKK) present in the MAP kinase pathway.

The "RalGDS-Caax" is a constitutively active form localized in the membrane by the addition of a Caax motif sequence to the C-terminus of Ras target protein, which activates Ral which is a G protein belonging to the Ras subfamily.

Figure 4:
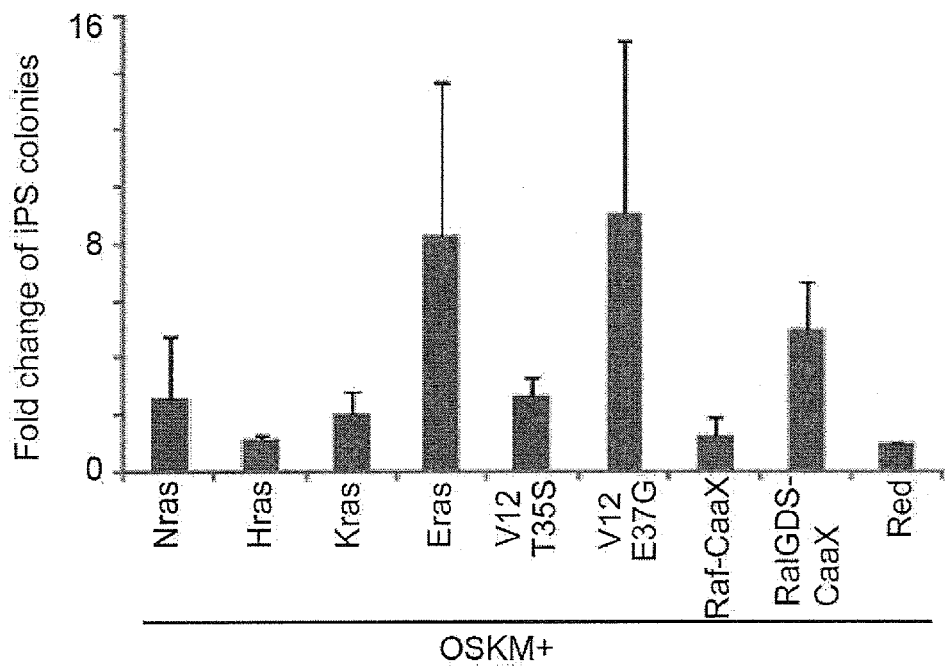
FIG. 4 shows a graph presenting the results of Example 4, wherein the vertical axis shows fold change of the number of iPS colonies when the number of colonies obtained by 4 transgenes of Oct3/4, Sox2, Klf4 and c-Myc is 1 (Red in the Figure), and the horizontal axis shows combinations of Oct3/4, Sox2, Klf4 and c-Myc genes and respective genes shown in the horizontal axis.

The cells were collected on day 7 from the viral infection, and replated on feeder cells ($2.5\times10^5$ cells/100 mm dish). From day 10 from the infection, the cells were cultured in a primate ES cell culture medium (ReproCELL) supplemented with 4 ng/ml recombinant human bFGF (WAKO). The iPS cell colonies were counted on day 24 from the infection, and the fold change when the number of the colonies obtained by 4 transgene is 1 (Red in Figure) is shown in FIG. 4. FIG. 4 shows mean values of three experiments.

By adding V12E37G to 4 genes in the same manner as in Examples 2 and 3, the number of human iPS cell colonies increased dramatically. In addition, since a similar effect was found when a constitutively active form of RalGDS which is a Ral activator was added, activation of the Ral pathway was confirmed to contribute to the promotion of iPS cell establishment. In contrast, when V12T35S and a constitutively active form of Raf were added, the effect was low. Therefore, the MAP kinase pathway was suggested to contribute not much to iPS cell establishment.

Example 5

Consideration of Effect of Ras Signal Transduction Pathway on Human iPS Cell Establishment (3)

Figure 5:
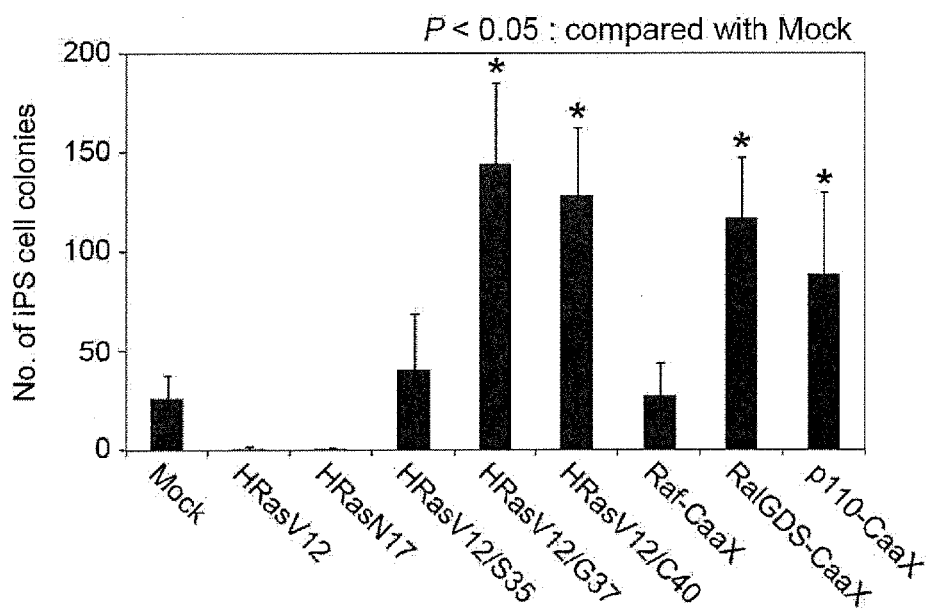
FIG. 5 shows a graph presenting the results of Example 5, wherein the vertical axis indicates the number of iPS cell colonies, and the horizontal axis shows combinations of Oct3/4, Sox2, Klf4 and c-Myc genes and respective genes shown in the horizontal axis.

The effect of activation of each Ras signal transduction pathway on iPS cell establishment was examined in the same manner as in the aforementioned Examples and using the following combinations.
1) Human Oct3/4, Sox2, Klf4, c-Myc, V12 (shown as "HRasV12" in FIG. 5)
2) Human Oct3/4, Sox2, Klf4, c-Myc, N17 (shown as "HRasN17" in FIG. 5)
3) Human Oct3/4, Sox2, Klf4, c-Myc, V12T35S (shown as "HRasV12/S35" in FIG. 5)
4) Human Oct3/4, Sox2, Klf4, c-Myc, V12E37G (shown as "HRasV12/G37" in FIG. 5)
5) Human Oct3/4, Sox2, Klf4, c-Myc, V12Y40C (shown as "HRasV12/C40" in FIG. 5)
6) Human Oct3/4, Sox2, Klf4, c-Myc, Raf-CaaX
7) Human Oct3/4, Sox2, Klf4, c-Myc, RalGDS-CaaX
8) Human Oct3/4, Sox2, Klf4, c-Myc, PI3K-CaaX (shown as "p110-CaaX" in FIG. 5)

The cells were collected on day 7 from the viral infection, and replated on feeder cells ($2.5\times10^5$ cells/100 mm dish). From day 8 from the infection, the cells were cultured in a primate ES cell culture medium (ReproCELL) supplemented with 4 ng/ml recombinant human bFGF (WAKO). FIG. 5 shows the number of the iPS cell colonies on day 24 from the infection. FIG. 5 shows mean values of three experiments. In the same manner as in Examples 1-4, by adding V12E37G, V12Y40C, RalGDS-CaaX or PI3K-CaaX to 4 genes, the number of the human iPS cell colonies increased remarkably. From the above results, the activation of the PI3 kinase pathway and Ral pathway was confirmed to contribute to the promotion of iPS cell establishment. In contrast, the MAP kinase pathway was suggested to contribute not much to iPS cell establishment.

Example 6

Consideration of Relationship of Each Ras Signal Transduction Pathway

Whether the PI3 kinase pathway, Ral pathway and MAP kinase pathway are related to each other or independent pathways for iPS cell establishment was examined.

Figure 6:
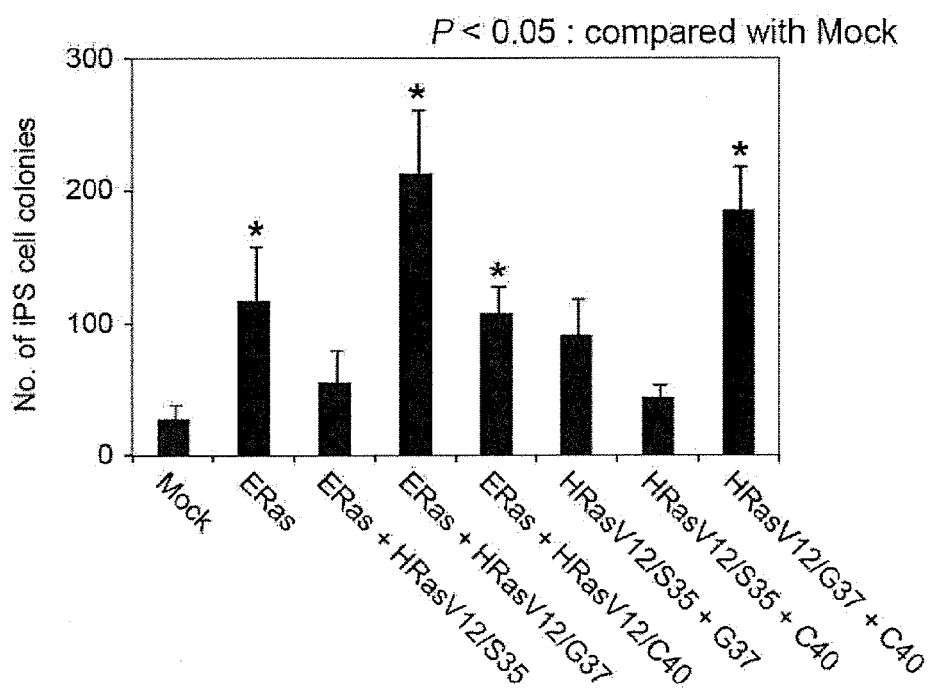
FIG. 6 shows a graph presenting the results of Example 6, wherein the vertical axis indicates the number of iPS cell colonies, and the horizontal axis shows combinations of Oct3/4, Sox2, Klf4 and c-Myc genes and respective genes shown in the horizontal axis.

The experiment was performed in the same manner as in Example 5. The results are shown in FIG. 6. FIG. 6 shows mean values of three experiments. When V12Y40C was added to Eras (ERas+HRasV12/C40 in FIG. 6), an additive effect (enhancement effect) was not found since they are factors that activate the PI3 kinase pathway. In contrast, when V12E37G was added to Eras (ERas+HRasV12/G37 in FIG. 6) and V12Y40C was added to V12E37G (HrasV12/G37+C40 in FIG. 6), an additive effect (enhancement effect) was found, which indicates that the Ral pathway and PI3 kinase pathway are involved in the promotion of iPS cell establishment by different, independent actions.

Example 7

Consideration of Effect in the Absence of bFGF

Figure 7:
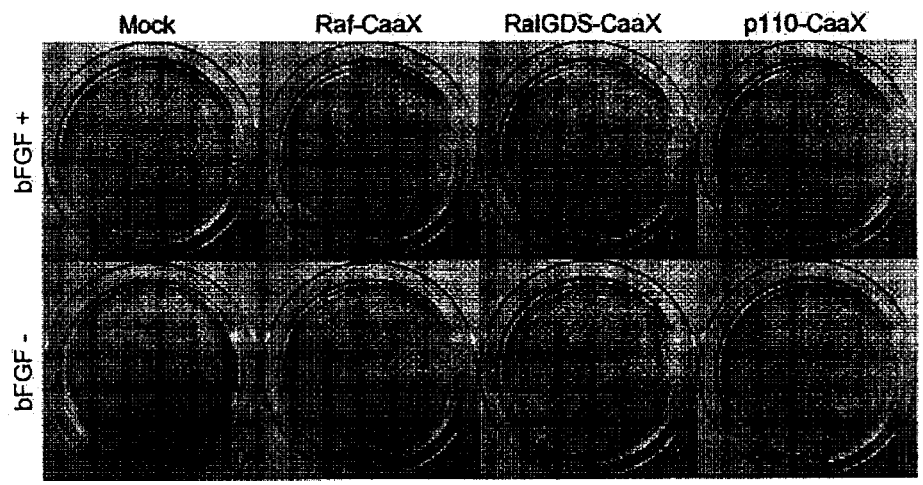
FIG. 7 shows alkaline phosphatase stain images of iPS cell colonies showing the results of Example 7, wherein each value shows the number of the iPS cell colonies.

The effects of Raf-CaaX, RalGDS-CaaX and PI3K-CaaX in the absence of bFGF were examined. The experiment was performed in the same manner as in Examples 5 and 6. The results are shown in FIG. 7. When RalGDS-CaaX was added to 4 genes, the number of the colonies of the same level as in the presence of bFGF was observed even in the absence of bFGF.

Example 8

Consideration of Effect of AKT on Human iPS Cell Establishment

Whether or not AKT as a downstream signal of PI3K has an effect on iPS cell establishment, and whether or not c-MYC or GSK3β influences iPS cell establishment by AKT were examined.

The following genes were introduced into human dermal fibroblasts (HDF: cell name 1616, purchased from Cell applications, Inc.) in the same manner as in the aforementioned Example 1.
1) Human Oct3/4, Sox2, Klf4, Mock
2) Human Oct3/4, Sox2, Klf4, Myr-AKT1
3) Human Oct3/4, Sox2, Klf4, c-MYC shRNA
4) Human Oct3/4, Sox2, Klf4, Myr-AKT1, c-MYC shRNA
5) Human Oct3/4, Sox2, Klf4, Myr-AKT1, GSK3β S9A Here, "Myr-AKT1" is a constitutively active AKT1 localized in the membrane by the addition of a myristoylation signal sequence to the N-terminus.

The "c-MYC shRNA" is shRNA targeting c-MYC, and used here was pRetrosuper Myc shRNA (Plasmid 15662) purchased from Addgene.

The "GSK3β S9A" is a constitutively active mutant which is not degraded by protease, by the substitution of the 9th serine of GSK3β by alanine.

Figure 8A:
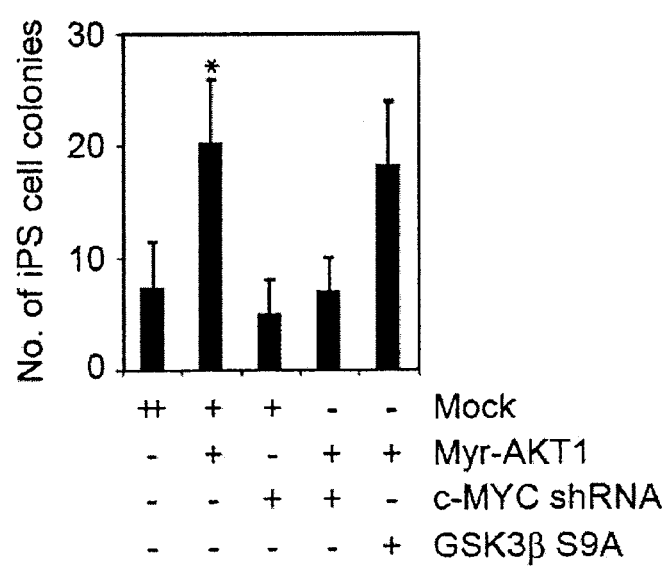
In FIG. 8A, the vertical axis indicates the number of iPS cell colonies. The horizontal axis shows combinations of Oct3/4, Sox2 and Klf4 genes with the 2-fold amounts of and Mock; Mock and Myr-AKT1; Mock and c-MYC shRNA; Myr-AKT1 and c-MYC shRNA; or Myr-AKT1 and GSK3βS9A.

On day 32 from the infection, the number of the iPS cell colonies was counted, and the results are shown in FIG. 8A.

By adding Myr-AKT1, the number of the human iPS cell colonies increased significantly. Since this effect disappeared when shRNA of c-MYC was added, c-MYC was shown to be essential for the promotion of iPS cell establishment by AKT1 activation. On the other hand, since GSK3β S9A produced no influence, phosphorylation of GSK3β was shown to be uninvolved as AKT1 downstream signal.

In addition, the culture condition was changed ($5 \times 10^5$ cells/well), and the following genes were introduced into human dermal fibroblasts (HDF: cell name 1616, purchased from Cell applications, Inc.) in the same manner.
1) Human Oct3/4, Sox2, Klf4, Mock
2) Human Oct3/4, Sox2, Klf4, p110-Caax
3) Human Oct3/4, Sox2, Klf4, p110-KD
4) Human Oct3/4, Sox2, Klf4, Myr-AKT1
5) Human Oct3/4, Sox2, Klf4, AKT1-KD
6) Human Oct3/4, Sox2, Klf4, PTEN shRNA
7) Human Oct3/4, Sox2, Klf4, TCL1

Here, "p110-Caax" is equivalent to the aforementioned "PI3K-CaaX".

The "p110-KD" is inactivated PI3K which is a mutant lacking the kinase domain.

The "AKT1-KD" is inactivated AKT1 which is a mutant lacking the kinase domain.

The "PTEN shRNA" is shRNA against PTEN (phosphatase and tensin homolog) that suppresses the PI3K pathway, and used here was pMK0.1 puro PTEN shRNA (Plasmid 10669) purchased from Addgene.

Figure 8B:
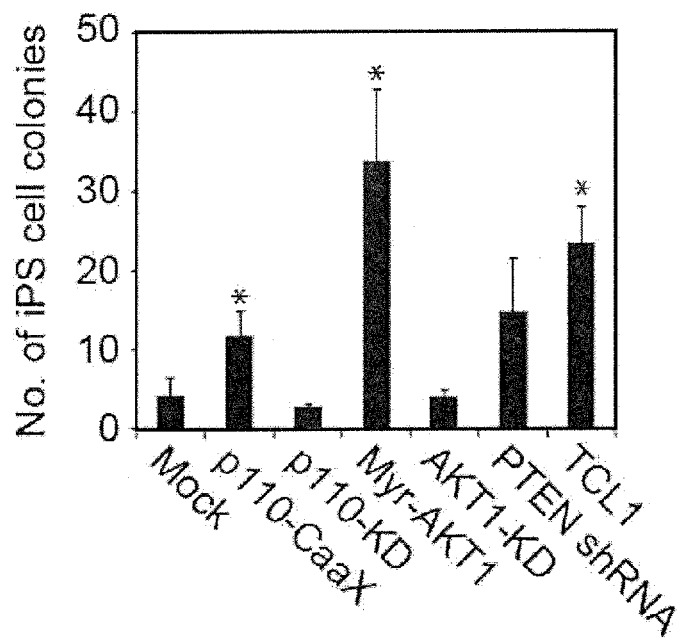
In FIG. 8B, the vertical axis indicates the number of iPS cell colonies, and the horizontal axis shows combinations of Oct3/4, Sox2 and Klf4 genes and respective genes shown in the horizontal axis.

On day 7 from the infection, the number of the iPS cell colonies was counted, and the results are shown in FIG. 8B.

In the same manner as in the earlier experiment, the number of the human iPS cell colonies increased significantly by the addition of Myr-AKT1. Since a similar effect was found by the addition of TCL1 which is an AKT1 activator, the activation of AKT1 was suggested to be involved in the promotion of iPS cell establishment.

Example 9

Consideration of Effect of AKT Related Signal on Human iPS Cell Establishment

The influence of AKT-related signals (PDK1, GSK3(3, Wnt) on the iPS cell establishment efficiency was examined.

In the same manner as in the aforementioned Example 1, the following genes were introduced into dermal fibroblasts (HDF: cell name 1616) in the presence of each low-molecular-weight compound.
1) Human Oct3/4, Sox2, Klf4, PS48
2) Human Oct3/4, Sox2, Klf4, CHIR99021
3) Human Oct3/4, Sox2, Klf4, Wnt3a Here, "PS48" is a drug that selectively binds to a PIF binding pocket site of PDK1 and activates PDK1. In this experiment, 10 μM was added to the medium. It was available from Sigma and used.

The "CHIR99021" is an inhibitor showing high selectivity to GSK3β. In this experiment, 1 μM was added to a medium. It was purchased from Stemgent and used.

The "Wnt3a" was purchased from R&D systems Inc., and 10 ng/ml thereof was added to the medium.

Figure 9:
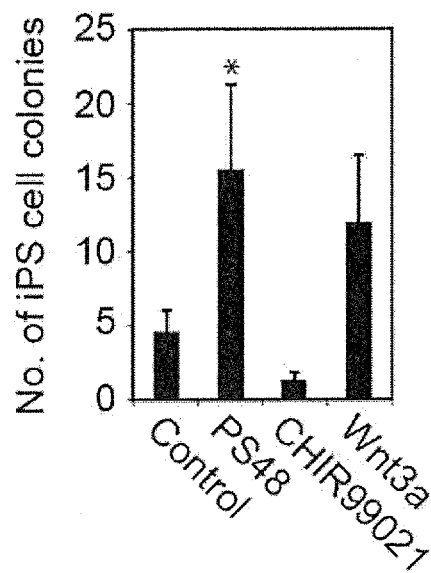
FIG. 9 shows a graph presenting the results of Example 9, wherein the vertical axis indicates the number of iPS cell colonies, and the horizontal axis shows combinations of Oct3/4, Sox2 and Klf4 genes and respective genes shown in the horizontal axis.

On day 32 from the infection, the number of the iPS cell colonies was counted, and the results are shown in FIG. 9.

By adding PS48 and Wnt3a, the number of the human iPS cell colonies increased significantly. On the other hand, when CHIR99021 was added, the number of the iPS cell colonies tended to decrease. From the above, it was shown that PDK1 and Wnt signals at the downstream of PI3K signal are involved in the promotion of iPS cell establishment, but inhibition of GSK3β phosphorylation is not involved in the iPS cell establishment.

Example 10

Consideration of Effect of AKT Family and mTOR Signal on Human iPS Cell Establishment The following genes were introduced into dermal fibroblasts (HDF: cell name 1616) in the same manner as in the aforementioned Example 1.
1) Human Oct3/4, Sox2, Klf4, Mock
2) Human Oct3/4, Sox2, Klf4, p110-Caax
3) Human Oct3/4, Sox2, Klf4, PTEN shRNA
4) Human Oct3/4, Sox2, Klf4, Myr-AKT1
5) Human Oct3/4, Sox2, Klf4, AKT1 K179M
6) Human Oct3/4, Sox2, Klf4, Myr-AKT1#2
7) Human Oct3/4, Sox2, Klf4, Myr-AKT2
8) Human Oct3/4, Sox2, Klf4, Myr-AKT3
9) Human Oct3/4, Sox2, Klf4, Myr-SGK1
10) Human Oct3/4, Sox2, Klf4, SGK1 K127M
11) Human Oct3/4, Sox2, Klf4, Myr-ILK
12) Human Oct3/4, Sox2, Klf4, ILK E359K
13) Human Oct3/4, Sox2, Klf4, Myr-PDK1
14) Human Oct3/4, Sox2, Klf4, GSK3 S9A
15) Human Oct3/4, Sox2, Klf4, Rheb
16) Human Oct3/4, Sox2, Klf4, S6K1 T389E
17) Human Oct3/4, Sox2, Klf4, FKBP12

Here, "p110-Caax" is equivalent to the aforementioned "PI3K-CaaX".

The "PTEN shRNA" is shRNA against PTEN (phosphatase and tensin homolog) that suppresses PI3K pathway, and used here was pMK0.1 puro PTEN shRNA (Plasmid 10669) purchased from Addgene.

The "Myr-AKT1#2" is a constitutively active AKT1 different from Myr-AKT1 in plasmid of a basic skeleton.

The "AKT1 K179M" is an inactive dominant negative AKT1 wherein the kinase region is mutated.

The "Myr-AKT2" is a constitutively active AKT2 localized in the membrane by the addition of a myristoylation signal sequence to the N-terminus.

The "Myr-AKT3" is a constitutively active AKT3 localized in the membrane by the addition of a myristoylation signal sequence to the N-terminus.

The "Myr-SGK1" is a constitutively active SGK1 localized in the membrane by the addition of a myristoylation signal sequence to the N-terminus of SGK1 (Serum/glucocorticoid regulated kinase) which is an important regulator in the mTORC2/SGK1 pathway and a protein kinase in the insulin signal transduction system.

The "SGK1 K127M" is a dominant negative SGK1 wherein the kinase region is mutated by the substitution of the 127th lysine of SGK1 by methionine.

The "Myr-ILK" is a constitutively active ILK localized in the membrane by the addition of a myristoylation signal sequence to the N-terminus of ILK (Integrin Linked Kinase) which is a serine/threonine kinase located in the upstream of the AKT in the PI3K signal. ILK inhibits the PI3K/AKT pathway by binding to PDK in the upstream of AKT.

The "ILK E359K" is a dominant negative ILK wherein the kinase region is mutated by the substitution of the 359th glutamic acid of ILK by lysine.

The "Myr-PDK1" is a constitutively active PDK1 localized in the membrane by the addition of a myristoylation signal sequence to the N-terminus of PDK1 included in the PDK subfamily.

The "S6K1 T389E" is a constitutively active S6K1 mutant by the substitution of the 389th threonine of S6K1 by glutamic acid.

Figure 10:
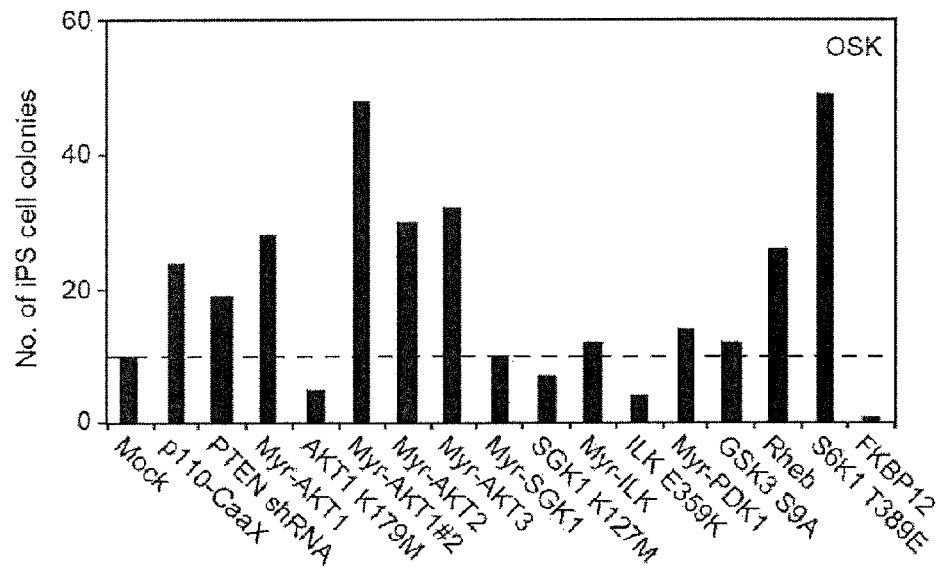
FIG. 10 shows a graph presenting the results of Example 10, wherein the vertical axis indicates the number of iPS cell colonies, and the horizontal axis shows combinations of Oct3/4, Sox2 and Klf4 genes and respective genes shown in the horizontal axis.

On day 32 from the infection, the number of the iPS cell colonies was counted, and the results are shown in FIG. 10.

In the same manner as in Example 3, the number of the iPS cell colonies increased by the addition of p110-Caax. Similarly, the number of the iPS cell colonies increased with PTEN shRNA, which shows the important of PI3K for the promotion of iPS cell establishment. As in Example 8, the number of the iPS cell colonies increased with Myr-AKT1, and similar results were also obtained with AKT2 and AKT3 in the AKT family.

In addition, the number of the human iPS cell colonies increased dramatically by the addition of Rheb, S6K1 T389E. The Rheb is a factor that activates mTOR, and S6K1 is a downstream factor of mTOR, and therefore, the activation of the mTOR signal pathway was suggested to contribute to the promotion of iPS cell establishment.

Example 11

Figure 11A:
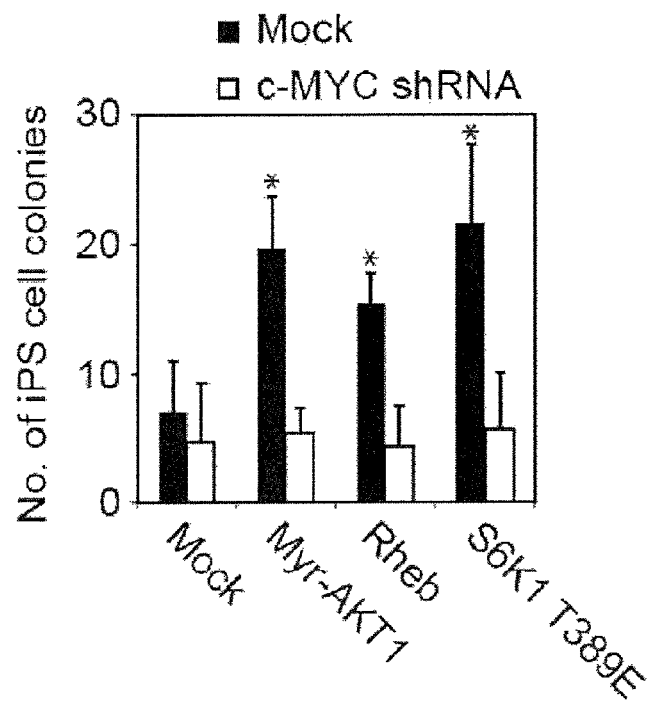
In FIG. 11A, the vertical axis indicates the number of the iPS cell colonies, and the horizontal axis shows combinations of Oct3/4, Sox2 and Klf4 genes and respective genes shown in the horizontal axis, in the presence or absence of c-Myc shRNA.

Consideration of c-MYC on Human iPS Cell Establishment by mTOR Signal Related Gene The following genes were introduced into dermal fibroblasts (HDF: cell name 1616) in the same manner as in the aforementioned Example 1.
1) Human Oct3/4, Sox2, Klf4, Mock
2) Human Oct3/4, Sox2, Klf4, Mock, c-MYC shRNA
3) Human Oct3/4, Sox2, Klf4, Myr-AKT1
4) Human Oct3/4, Sox2, Klf4, Myr-AKT1, c-MYC shRNA
5) Human Oct3/4, Sox2, Klf4, Rheb
6) Human Oct3/4, Sox2, Klf4, Rheb, c-MYC shRNA
7) Human Oct3/4, Sox2, Klf4, S6K1 T389E
8) Human Oct3/4, Sox2, Klf4, S6K1 T389E, c-MYC shRNA On day 32 from the infection, the number of the iPS cell colonies was counted, and the results are shown in FIG. 11A. In all cases, the effect of promotion of the iPS cell establishment disappeared by the addition of c-MYC shRNA, which shows that c-MYC is essential for the promotion of iPS cell establishment by these genes.

Furthermore, Mock, Myr-AKT1, Rheb, S6K1 T389E and p53 shRNA were introduced into dermal fibroblasts (HDF: cell name 1616). On day 7 from the introduction, the intracellular protein was recovered by a conventional method, and the expression levels of c-MYC, p-AKT, AKT, p-S6K1, S6K1, p-TSC2 and TSC2 were confirmed by Western blotting.

Here, "p53 shRNA" is shRNA against p53 and the sequence described in Hong H, et al., Nature. 460: 1132-1135 (2009) was used.

Figure 11B:
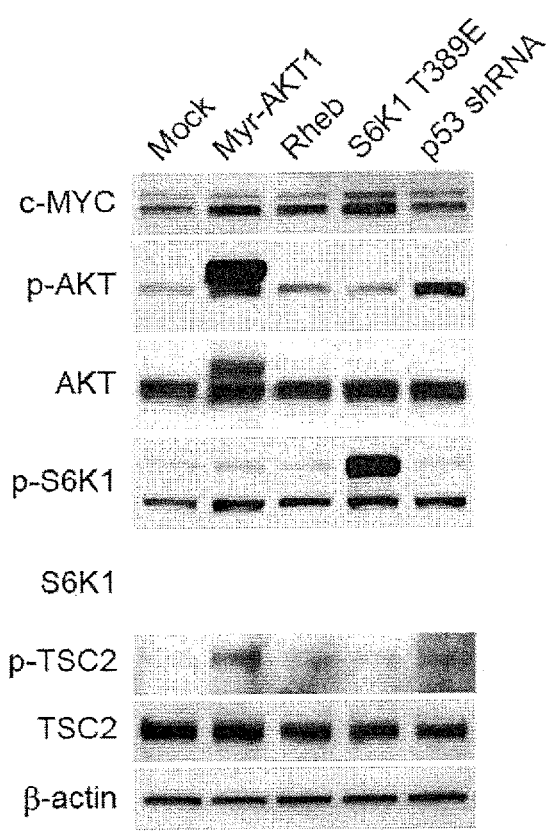
FIG. 11B shows the measurement results by Western blotting of the intracellular expression of the proteins of c-Myc, p-AKT (phosphorylated AKT), AKT, p-S6K1 (phosphorylated S6K1), S6K1, p-TSC2 (phosphorylated TSC2) and TSC2, when Mock, Myr-AKT1, Rheb, S6K1 T389E or p53 shRNA were each introduced into the human dermal fibroblast.

The results are shown in FIG. 11B.

Increase of the expression level of c-MYC by the introduction of Myr-AKT1, Rheb and S6K1 T389E was confirmed. From this, the mechanism of promotion of iPS cell establishment by Myr-AKT1, Rheb and S6K1 T389E via increased expression of c-MYC was suggested.

In addition, introduction of p53 shRNA increased phosphorylated AKT. Since Hong H et al. show promotion of iPS cell establishment by the inhibition of p53, the inhibition of p53 was suggested to promote iPS cell establishment via AKT phosphorylation.

Example 12

Consideration of Effect of AKT1 on Promotion of Human iPS Cell Establishment by Inhibition of p53 and Introduction of GLIS1

Figure 12A:
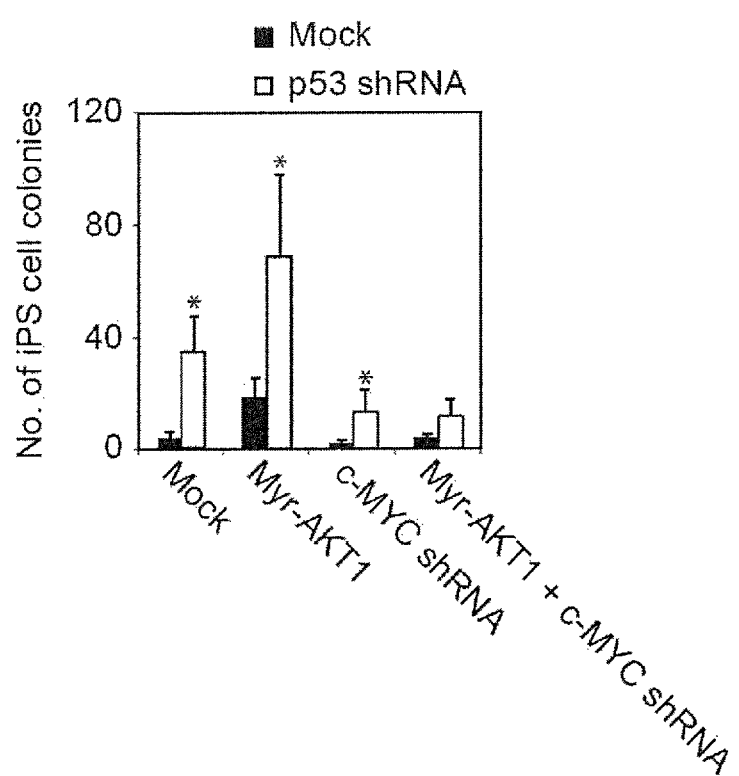
FIG. 12A shows the results of introduction into human dermal fibroblast, wherein the vertical axis indicates the number of iPS cell colonies and the horizontal axis shows combinations of Oct3/4, Sox2 and Klf4 genes and respective genes shown in the horizontal axis, in the presence or absence of p53 shRNA.

The following genes were introduced into human dermal fibroblasts (HDF: cell name 1616) in the same manner as in the aforementioned Example 1.
1) Human Oct3/4, Sox2, Klf4, Mock
2) Human Oct3/4, Sox2, Klf4, Mock, p53 shRNA
3) Human Oct3/4, Sox2, Klf4, Myr-AKT1
4) Human Oct3/4, Sox2, Klf4, Myr-AKT1, p53 shRNA
5) Human Oct3/4, Sox2, Klf4, c-MYC shRNA
6) Human Oct3/4, Sox2, Klf4, c-MYC shRNA, p53 shRNA
7) Human Oct3/4, Sox2, Klf4, Myr-AKT1, c-MYC shRNA
8) Human Oct3/4, Sox2, Klf4, Myr-AKT1, c-MYC shRNA, p53 shRNA On day 32 from the infection, the number of the iPS cell colonies was counted, and the results are shown in FIG. 12A.

By simultaneous addition of Myr-AKT1 and p53 shRNA, increase of the number of iPS cell colonies was observed. Therefore, introduction of p53 shRNA and AKT1 was shown to have a synergistic effect on the promotion of iPS cell establishment. In addition, since the number of iPS cell colonies decreased by c-MYC shRNA in all cases, these effects were suggested to be actions via c-MYC.

Furthermore, the following genes were introduced into human dermal fibroblasts (HDF: cell name 1616).
1) Human Oct3/4, Sox2, Klf4, Mock
2) Human Oct3/4, Sox2, Klf4, Mock, GLIS1
3) Human Oct3/4, Sox2, Klf4, Myr-AKT1
4) Human Oct3/4, Sox2, Klf4, Myr-AKT1, GLIS1
5) Human Oct3/4, Sox2, Klf4, c-MYC shRNA
6) Human Oct3/4, Sox2, Klf4, c-MYC shRNA, GLIS1
7) Human Oct3/4, Sox2, Klf4, Myr-AKT1, c-MYC shRNA
8) Human Oct3/4, Sox2, Klf4, Myr-AKT1, c-MYC shRNA, GLIS1

Figure 12B:
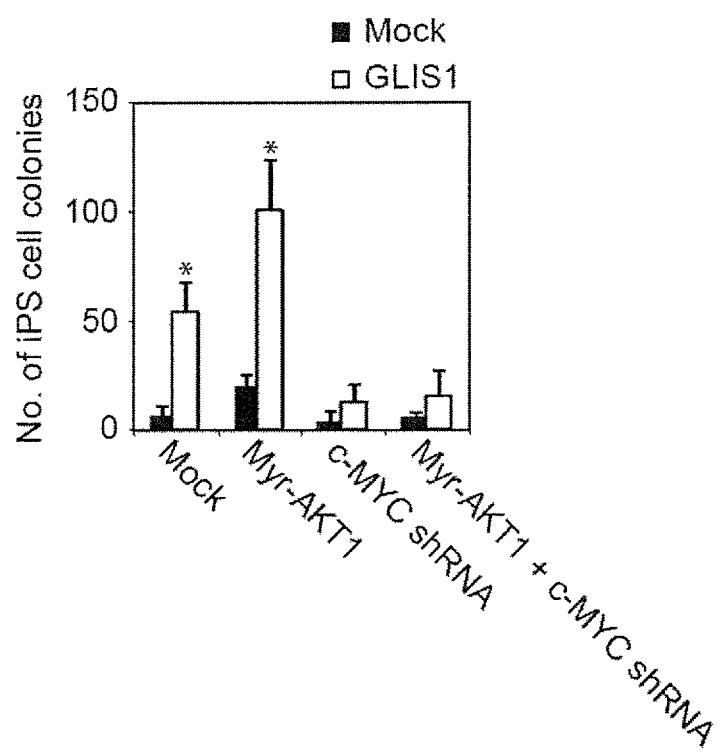
FIG. 12B shows the results of introduction into human dermal fibroblast, wherein the vertical axis indicates the number of iPS cell colonies and the horizontal axis shows combinations of Oct3/4, Sox2 and Klf4 genes and respective genes shown in the horizontal axis, in the presence or absence of GLIS1.

On day 32 from the infection, the number of the iPS cell colonies was counted, and the results are shown in FIG. 12B.

By simultaneous addition of Myr-AKT1 and GLIS1, increase of the number of iPS cell colonies was observed. Therefore, introduction of GLIS1 and AKT1 was shown to have a synergistic effect on the promotion of iPS cell establishment. In addition, since the number of iPS cell colonies decreased by c-MYC shRNA in all cases, these effects were suggested to be actions via c-MYC.

Furthermore, to examine similar effects in other cell lines, the following genes were introduced into human dental pulp cells (DP: cell name DP31).
1) Human Oct3/4, Sox2, Klf4, Mock, Mock
2) Human Oct3/4, Sox2, Klf4, Mock, p53 shRNA
3) Human Oct3/4, Sox2, Klf4, Mock, GLIS1
4) Human Oct3/4, Sox2, Klf4, Myr-AKT1, Mock
5) Human Oct3/4, Sox2, Klf4, Myr-AKT1, p53 shRNA
6) Human Oct3/4, Sox2, Klf4, Myr-AKT1, GLIS1
7) Human Oct3/4, Sox2, Klf4, c-MYC shRNA, Mock
8) Human Oct3/4, Sox2, Klf4, c-MYC shRNA, p53 shRNA 9) Human Oct3/4, Sox2, Klf4, c-MYC shRNA, GLIS1
10) Human Oct3/4, Sox2, Klf4, Myr-AKT1, c-MYC shRNA, Mock
11) Human Oct3/4, Sox2, Klf4, Myr-AKT1, c-MYC shRNA, p53 shRNA
12) Human Oct3/4, Sox2, Klf4, Myr-AKT1, c-MYC shRNA, GLIS1

Figure 12C:
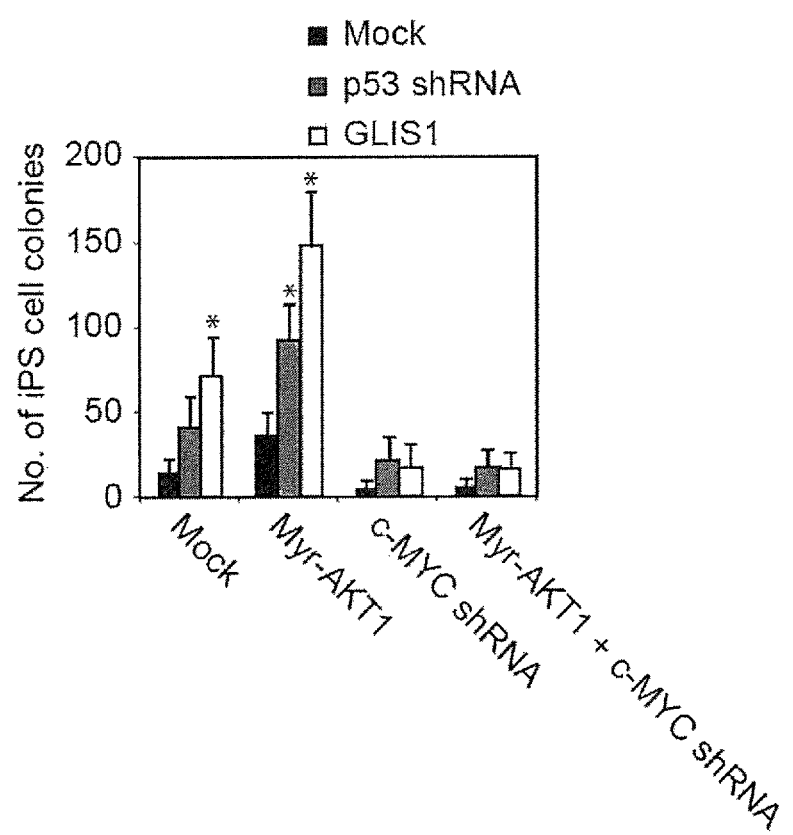
FIG. 12C shows the results of introduction into human dental pulp cell, wherein the vertical axis indicates the number of the iPS cell colonies and the horizontal axis shows combinations of Oct3/4, Sox2 and Klf4 genes and respective genes shown in the horizontal axis, in the presence or absence of p53 shRNA, as well as combinations of Oct3/4, Sox2 and Klf4 genes and respective genes shown in the horizontal axis, in the presence or absence of GLIS1.

On day 32 from the infection, the number of the iPS cell colonies was counted, and the results are shown in FIG. 12C.

Similar to the above-mentioned results, the number of the iPS cell colonies increased by simultaneous addition of Myr-AKT1 and p53 shRNA or Myr-AKT1 and GLIS1.

From this, it was shown that, regardless of the somatic cell type, introduction of AKT1 and inhibition of p53, or the introduction of AKT1 and GLIS1 have a synergistic effect on the promotion of iPS cell establishment.

The contents described in any publication cited herein, including patents and patent applications, are hereby incorporated in their entireties by reference, to the extent that they have been disclosed herein.

This application is based on U.S. provisional patent application No. 61/419,320, the contents of which are encompassed in full herein.

---

The invention claimed is:

1. A method of producing induced pluripotent stem cells, comprising contacting a somatic cell with a nuclear reprogramming substance(s) and a nucleic acid vector(s) encoding one or more AKT family members, thereby producing functionally pluripotent stem cells,
wherein the nuclear reprogramming substance(s) comprises a nucleic acid vector encoding Oct3/4 and optionally comprises a nucleic acid vector(s) encoding one or more substances selected from the group consisting of Sox2, Klf4, c-Myc, Lin28 and Nanog.

2. The method according to claim 1, wherein the AKT family members are constitutively active forms.

3. The method according to claim 1, wherein the AKT family members are selected from the group consisting of AKT1, AKT2 and AKT3.

4. The method according to claim 2, wherein the AKT family members constitutively activate signal transduction pathway of mTOR pathway.

5. The method according to claim 1, further comprising contacting one or more factors selected from the group consisting of p53 inhibitor, GLIS family members, and nucleic acids that encode the same with the somatic cell.

6. The method according to claim 1, wherein the nuclear reprogramming substances comprise a nucleic acid vector(s) encoding Oct3/4, Klf4 and Sox2.

7. The method according to claim 1, wherein the nuclear reprogramming substances comprise a nucleic acid vector(s) encoding Oct3/4, Klf4, Sox2, as well as c-Myc or L-Myc and/or Nanog and/or Lin28 or Lin28B.

8. A method of improving the efficiency of establishment of a reprogrammed cell, comprising contacting a somatic cell with (a) a nuclear reprogramming substance(s) and (b) a nucleic acid vector(s) encoding one or more AKT family members, thereby improving the efficiency of establishment of reprogrammed cells as compared to the establishment of reprogrammed cells established without contacting the somatic cell with (b),
- wherein the nuclear reprogramming substance(s) comprises a nucleic acid vector encoding Oct3/4 and optionally comprises a nucleic acid vector(s) encoding one or more substances selected from the group consisting of Sox2, Klf4, c-Myc, Lin28 and Nanog, and
- wherein the reprogrammed cell is in a more undifferentiated state than the somatic cell so as to form an ES-like colony.

9. The method according to claim 8, wherein the AKT family members are constitutively active forms.

10. The method according to claim 8, wherein the AKT family members are selected from the group consisting of AKT1, AKT2 and AKT3.

11. The method according to claim 9, wherein the AKT family members constitutively activate signal transduction pathway of mTOR pathway.

12. The method according to claim 8, further comprising contacting one or more factors selected from the group consisting of p53 inhibitor, GLIS family members, and nucleic acids that encode the same with the somatic cell.

13. The method according to claim 8, wherein the nuclear reprogramming substances comprise a nucleic acid vector(s) encoding Oct3/4, Klf4 and Sox2.

14. The method according to claim 8, wherein the nuclear reprogramming substances comprise a nucleic acid vector(s) encoding Oct3/4, Klf4, Sox2, as well as c-Myc or L-Myc and/or Nanog and/or Lin28 or Lin28B.

\* \* \* \* \*